US011427543B2

(12) United States Patent
Garkavtsev et al.

(10) Patent No.: US 11,427,543 B2
(45) Date of Patent: Aug. 30, 2022

(54) COMPOUNDS FOR TARGETING CANCER STEM CELLS

(71) Applicant: The General Hospital Corporation, Boston, MA (US)

(72) Inventors: Igor Garkavtsev, Cambridge, MA (US); Rakesh K. Jain, Wellesley, MA (US)

(73) Assignee: The General Hospital Corporation, Boston, MA (US)

( * ) Notice: Subject to any disclaimer, the term of this patent is extended or adjusted under 35 U.S.C. 154(b) by 815 days.

(21) Appl. No.: 16/318,846

(22) PCT Filed: Jul. 18, 2017

(86) PCT No.: PCT/US2017/042630
§ 371 (c)(1),
(2) Date: Jan. 18, 2019

(87) PCT Pub. No.: WO2018/017589
PCT Pub. Date: Jan. 25, 2018

(65) Prior Publication Data
US 2021/0238140 A1   Aug. 5, 2021

Related U.S. Application Data

(60) Provisional application No. 62/483,587, filed on Apr. 10, 2017, provisional application No. 62/364,215, filed on Jul. 19, 2016.

(51) Int. Cl.
| C07C 241/00 | (2006.01) |
| A61K 31/343 | (2006.01) |
| A61P 35/00 | (2006.01) |
| C07D 213/82 | (2006.01) |
| C07C 251/80 | (2006.01) |
| C07D 213/53 | (2006.01) |

(52) U.S. Cl.
CPC ............ C07D 213/82 (2013.01); A61P 35/00 (2018.01); C07C 251/80 (2013.01); C07D 213/53 (2013.01)

(58) Field of Classification Search
CPC ...... C07C 241/00; A61K 31/343; A61P 35/00
See application file for complete search history.

(56) References Cited

U.S. PATENT DOCUMENTS 6,166,257 A  12/2000 Mathey et al.
6,610,875 B1  8/2003 Lemaire et al.

FOREIGN PATENT DOCUMENTS

| CN | 103880707 | 6/2014 |
| WO | WO 2006/136008 | 12/2006 |
| WO | WO 2012/027548 | * 3/2012 |
| WO | WO 2013/025805 | 2/2013 |

OTHER PUBLICATIONS

Al-Hajj et al, "Prospective identification of tumorigenic breast cancer cells," Proceedings of the National Academy of Sciences in the United States of America, 2003, 100:3983-3988.
Berge et al, "Pharmaceutical Salts," Journal of Pharmaceutical Science, 1977, 66:2, 19 pages.
Bernstein et al, "A Bivalent Chromatin Structure Marks Key Developmental Genes in Embryonic Stem Cells," Cell, 2006, 125:315-326.
Chaffer et al, "Poised Chromatin at the ZEB1 Promoter Enables Breast Cancer Cell Plasticity and Enhances Tumorigenicity," Cell, 2013, 154:61-74.
Chan et al, "Identification, molecular characterization, clinical prognosis, and therapeutic targeting of human bladder tumor-initiating cells," Proceedings of the National Academy of Sciences in the United States of America, 2009, 106:14016-14021.
Chen et al, "Identification and Characterization of Novel Inhibitors of Mammalian Aspartyl Aminopeptidase," Molecular Pharmacology, 2014, 86:231-242.
Choudhary et al, "Dynamic Acylhydrazone Metal Ion Complex libraries: A Mixed+ligand Approach to Increased Selectivity in Extraction," Angewandte Chemie International Edition, 2002, 41:4096-4098.
Garkavtsev et al, "The candidate tumour suppressor protein ING4 regulates brain tumour growth and angiogenesis," Nature, 2004, 428:328-332.
Gilani et al, "The importance of HER2 signaling in the tumor-initiating cell population in aromatase inhibitor-resistant breast cancer," Breast Cancer Research and Treatment, 2012, 135:681-692.
Ginestier et al, "ALDH1 Is a Marker of Normal and Malignant Human Mammary Stem Cells and a Predictor of Poor Clinical Outcome," Cell Stem Cell, 2007, 1:555-567.
Hambardzumyan et al, "Radiation resistance and stem-like cells in brain tumors," Cancer Cell, 2006, 10:454-456.
Hung et al, "ING4 Mediates Crosstalk between Histone H3 K4 Trimethylation and H3 Acetylation to Attenuate Cellular Transformation," Molecular Cell, 2009, 33:248-256.
Li et al, "Intrinsic Resistance of Tumorigenic Breast Cancer Cells to Chemotherapy," Journal of the National Cancer Institute, 2008, 100:672-679.
Mani et al, "The Epithelial-Mesenchymal Transition Generates Cells with Properties of Stem Cells," Cell, 2008, 133:704-715.
Marjanovic et al, "Cell plasticity and heterogeneity in cancer," Clinical Chemistry, 2013, 59:168-179.
Morel et al, "Generation of Breast Cancer Stem Cells through Epithelial-Mesenchymal Transition," PloS one, 2008, 3:e2888, 7 pages.
Pahl, "Activators and target genes of Rel/NF-kB transcription factors," Oncogene, 1999, 18(49):6853-6866.

(Continued)

*Primary Examiner* — Bruck Kifle
(74) *Attorney, Agent, or Firm* — Fish & Richardson P.C.

(57) ABSTRACT

This invention relates to antagonists of G3BP2, G3BP1, and ZEB1. Pharmaceutical compositions comprising G3BP2 inhibitors, methods of inhibiting G3BP2, G3BP1, and ZEB1, methods of treating cancer and inflammation, and methods of identifying an inhibitor of cancer stems cells are also provided.

9 Claims, 32 Drawing Sheets

Specification includes a Sequence Listing.

(56) References Cited

OTHER PUBLICATIONS

Patrawala et al, "Highly purified CD44 þ prostate cancer cells from xenograft human tumors are enriched in tumorigenic and metastatic progenitor cells," Oncogene, 2006, 25:1696-1708.

PCT International Preliminary Report on Patentability in International Appln. No. PCT/US17/42630, dated Jan. 31, 2019, 8 pages.

PCT International Search Report and Written Opinion in International Appln. No. PCT/US17/42630, dated Dec. 20, 2017, 11 pages.

Pubmed Compound Summary for CID 20843946, "CID 20843946," U.S. National library of Medicine, Dec. 5, 2007 (Dec. 5, 2007). p. 1-9, (https:/lpubchem.ncbi.nlrn.nih.gov/compound/20843946).

Pubmed Compound Summary for CID 5073834, "AC1NNNJX," U.S. National Library of Medicine, Sep. 18, 2005 (Sep. 18, 2005), p. 1-11, (https:/lpubchem.ncbi.nlm.nih.gov/compound/5073834).

Roose et al, "Solid stress generated by spheroid growth estimated using a linear poroelasticity model," Microvasc Res, 2003, 66(3):204-12.

Shafee et al, "Cancer Stem Cells Contribute to Cisplatin Resistance in Brca1/p53—Mediated Mouse Mammary Tumors," Cancer Research, 2008, 68:3243-3250.

Unoki et al, "Novel splice variants of ING4 and their possible roles in the regulation of cell growth and motility," The Journal of Biological Chemistry, 2006, 281:34677-34686.

Buu-Hoi et al., "Isonicotinylhydrazones et nicotinylhydrazones dérivées de cétones heterocycliques" *Bulletin De La Societe Chimique De France*, Jan. 1961, 1377-1379.

Database Registry [Online] Chemical Abstracts Service, Columbus, Ohio, US; Jul. 28, 2006 (Jul. 28, 2006), XP002795774, retrieved from STN Database accession No. 896697-98-6.

Database Registry [Online] Chemical Abstracts Service, Columbus, Ohio, US; Apr. 12, 2002 (Apr. 12, 2002), XP002795775, retrieved from STN Database accession No. 405153-06-2.

Database Registry [Online] Chemical Abstracts Service, Columbus, Ohio, US; Feb. 22, 2002 (Feb. 22, 2002), XP002795776, retrieved from STN Database accession No. 394694-06-5.

Database Registry [Online] Chemical Abstracts Service, Columbus, Ohio, US; Apr. 9, 2003 (Apr. 9. 2003), XP002795778, retrieved from STN Database accession No. 502431-34-7.

Database Registry [Online] Chemical Abstracts Service, Columbus, Ohio, US; Apr. 9, 2001 (Apr. 9, 2001), XP002795779, retrieved from STN Database accession No. 330561-90-5.

Database Registry [Online] Chemical Abstracts Service, Columbus, Ohio, US; Jan. 19, 2001 (Jan. 19, 2001), XP002795780, retrieved from STN Database accession No. 315209-79-1.

Database Registry [Online] Chemical Abstracts Service, Columbus, Ohio, US; Jul. 1, 2003 (Jul. 1, 2003),, XP002795777, retrieved from STN Database accession No. 540529-04-2.

EP Supplementary Search Report in European Appln. No. 17831702.0, dated Dec. 18, 2019.

Isagawa et al, "Syntheses of Methoxyacetophenone and Anisylacetone-N(pyridinecarbonyl) hydrazones," Nippon Kagaku Zasshi—Journal of the Chemical Society of Japan, *Pure Chemistry Section*, Jan. 1969, 90(1):73-77.

Li et al., "2-Nitro-N'-[1-(pyridin-2-yl)ethylidene]benzohydrazide," *Acta Crystallographica Section E Structure Reports Online*, Dec. 2011, 67(12):o3353-o3353.

Maurya et al., "Catalytic oxidation of internal and terminal alkenes by oxidoperoxidomolybdenum(VI) and dioxidomolybdenum(VI) complexes," *Inorganica Chimica Acta*, Feb. 2015, 429:138-147.

Mondal et al., "Monoculear and binuclear Cu(II) complexes of some tridentate aroyl hydrazones. X-ray crystal structures of a mononuclear and a binuclear complex," *Inorganica Chimica Acta*, Dec. 2012, 398:98-105.

Pilo et al., "Effect of coordination to antimony (III) on the antifungal activity of 2-acetylpyridine-and 2-benzolypyridine-derived hydrazones," *Polyhedron*, May 2015, 97:30-38.

Suganthy et al., "Synthesis, structural characterization and catalytic transfer hydrogenation of ruthenium(II) carbonyl complexes bearing N,N,O pincer type benzoylhydrazone ligands" *Polyhedron*, Dec. 2004, 88:57-62.

Xu et al., "Synthesis, characterization and anticancer activities of two lanthanide(III) complexes with a nicotinohydrazone ligand," *Journal of Molecular Structure*, Dec. 2015, 1102:86-90.

\* cited by examiner

BT474

ZEB1

β-actin

MDA-MB 453

ZEB1

β-actin

```
MATAAETSAS EPEAESKAGP KADGEEDEVK AARTRRKVLS RAVAAATYKT MGPAWDQQEE GVSESDGDEY AMASSAESSP GEYEWEYDEE EEKNQLEIER
LEEQLSINVY DYNCHVDLIR LLRLEGELTK VRMARQKMSE IFPLTEELWL EWLHDEISMA QDGLDREHVY ICPNIWLEYG QYSVGGIGQK
GGLEKVRSVF ERALSSVGLH MTKGLALWEA YREFESAIVE AARLEKVHSL FRRQLAIPLY DMEATFAEYE EWSEDPIPES VIQNYNKALQ QLEKYKPYEE
ALLQAEAPRL AEYQAYIDFE MKIGDPARIQ LIFERALVEN CLVPDLWIRY SQYLDRQLKV KDLVLSVHNR AIRNCPWTVA LWSRYLLAME RHGVDHQVIS
VTFEKALNAG FIQATDYVEI WQAYLDYLRR RVDFKQDSSK ELEELRAAFT RALEYLKQEV EERFNESGDP SCVIMQNWAR IEARLCNNMQ KARELWDSIM
TRGNAKYANM WLEYYNLERA HGDTQHCRKA LHRAVQCTSD YPEHVCEVLL TMERTEGSLE DWDIAVQKTE TRLARVNEQR MKAAEKEAAL VQQEEEKAEQ
RKRARAEKKA LKKKKKIRGP EKRGADEDDE KEWGDDDEEEQ PSKRRRVENS IPAAGETQNV EVAAGPAGKC QKEKAASLKR DMPKVLHDSS
KDSITVFVSN LPYSMQEPDT KLRPLFEACG EVVQIRPIFS NRGDFRGYCY VEFKEEKSAL QALEMDRKSV EGRPMFVSPC VDKSKNPDFK VFRYSTSLEK
HKLFISGLPF SCTKEELEEI CKAHGTVKDL RLVTNRAGKP KGLAYVEYEN ESQASQAVMK MDGMTIKENI IKVAISNPPQ RKVPEKPETR KAPGGPMLLP
QTYGARGKGR TQLSLLPRAL QRPSAAAPQA ENGPAAAPAV AAPAATEAPK MSNADFAKLF LRK
```

SEQ ID NO: 7

FIG. 7A

MDA-MB-231 cells

COMPOUNDS FOR TARGETING CANCER STEM CELLS

CROSS-REFERENCE TO RELATED APPLICATIONS

This application is a § 371 National Stage Application of PCT/US2017/042630, filed Jul. 18, 2017, which claims the benefit of U.S. Provisional Application Ser. No. 62/364,215, filed Jul. 19, 2016, and 62/483,587, filed Apr. 10, 2017, the disclosure of each of which is incorporated herein by reference in its entirety.

FEDERALLY SPONSORED RESEARCH OR DEVELOPMENT

This invention was made with Government support under Grant No. 1R21CA169616 awarded by the National Institutes of Health and W81XWH-10-1-0016 awarded by the Department of Defense. The Government has certain rights in the invention.

SEQUENCE LISTING

The instant application contains a Sequence Listing which has been submitted electronically in ASCII format and is hereby incorporated by reference in its entirety. Said ASCII copy, created on Sep. 11, 2019, is named 29539-0143US1_SL.txt and is 10,679 bytes in size.

TECHNICAL FIELD

This invention relates to the therapeutic treatment of cancer stem cells, and more particularly to compounds useful as antagonists of G3BP2, G3BP1, and ZEB1.

BACKGROUND

Solid tumors are collections of cancer cells and host stromal cells, with each population being highly heterogeneous. The CSC model accounts for this phenomenon by positing that only a fraction of cancer cells, termed CSCs, can give rise to other cancer cells. In turn, these non-CSC progeny form the bulk of a breast tumor but do not create new cancer cells themselves. CSCs may be relatively resistant to front-line therapies such as radiation and chemotherapy (see e.g., Hambardzumyan et al., *Cancer Cell*, 2006, 10, 454-456; Li et al., *Journal of the National Cancer Institute*, 2008, 100, 672-679; Shafee et al., *Cancer Research*, 2008, 68, 3243-3250; and Gilani et al., *Breast Cancer Research and Treatment*, 2012, 135, 681-692), and by definition they contribute to relapse and metastatic spread.

SUMMARY

The present application provides, inter alia, a compound of Formula I:

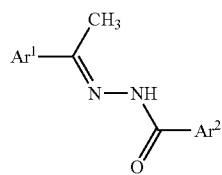

or a pharmaceutically acceptable salt thereof, wherein:

$Ar^1$ is selected from the group consisting of 2-pyridyl, 3-pyridyl, and phenyl, each of which may be optionally substituted by 1, 2, 3, or 4 independently selected $R^1$ groups; and $Ar^2$ is selected from the group consisting of 2-pyridyl, 3-pyridyl, and phenyl, each of which may be optionally substituted by 1, 2, 3, or 4 independently selected $R^2$ groups;

wherein at least one of $Ar^1$ and $Ar^2$ is 2-pyridyl or 3-pyridyl;

each R is independently selected from the group consisting of halo, $NO_2$, $OR^{a1}$, $C_{1-6}$ alkyl, $C_{2-6}$ alkenyl, and $C_{2-6}$ alkynyl;

each $R^2$ is independently selected from the group consisting of halo, $NO_2$, $OR^{a2}$, $C_{1-6}$ alkyl, $C_{2-6}$ alkenyl, and $C_{2-6}$ alkynyl; and each $R^{a1}$ is independently selected from the group consisting of H and $C_{1-4}$ alkyl;

each $R^{a2}$ is independently selected from the group consisting of H and $C_{1-4}$ alkyl; and wherein the compound is not a compound selected from the group consisting of:

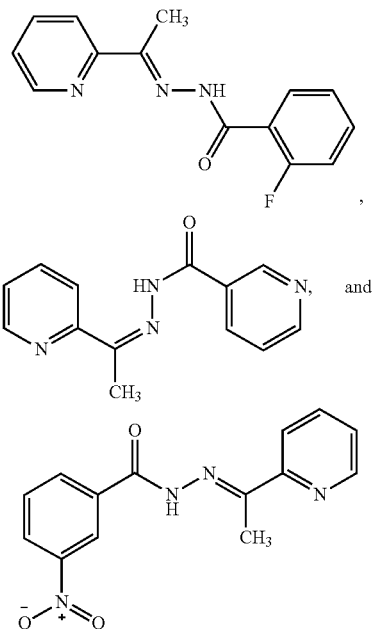

In some embodiments, $Ar^1$ is 2-pyridyl, optionally substituted by 1, 2, 3, or 4 independently selected $R^1$ groups. In some embodiments, $Ar^1$ is 3-pyridyl, optionally substituted by 1, 2, 3, or 4 independently selected $R^1$ groups. In some embodiments, $Ar^1$ is phenyl, optionally substituted by 1, 2, 3, or 4 independently selected $R^1$ groups.

In some embodiments, $Ar^2$ is 2-pyridyl, optionally substituted by 1, 2, 3, or 4 independently selected $R^2$ groups. In some embodiments, $Ar^2$ is 3-pyridyl, optionally substituted by 1, 2, 3, or 4 independently selected $R^2$ groups. In some embodiments, $Ar^2$ is phenyl, optionally substituted by 1, 2, 3, or 4 independently selected $R^2$ groups.

In some embodiments, each $R^1$ is independently selected from the group consisting of halo, $NO_2$, $OR^{a1}$, and $C_{1-6}$ alkyl. In some embodiments, each $R^1$ is independently selected from the group consisting of chloro, fluoro, $NO_2$, OH, methoxy, and methyl.

In some embodiments, each R² is independently selected from the group consisting of halo, NO₂, OR^{a1}, and C_{1-6} alkyl. In some embodiments, each R² is independently selected from the group consisting of chloro, fluoro, NO₂, OH, methoxy, and methyl.

In some embodiments:

Ar¹ is 2-pyridyl, optionally substituted by 1, 2, 3, or 4 independently selected R¹ groups;

Ar² is phenyl, optionally substituted by 1, 2, 3, or 4 independently selected R² groups;

each R¹ is independently selected from the group consisting of halo, NO₂, OR^{a1}, and C_{1-6} alkyl;

each R² is independently selected from the group consisting of halo, NO₂, OR^{a2}, and C_{1-6}alkyl;

each R^{a1} is independently selected from the group consisting of H and C_{1-4} alkyl; and each R^{a2} is independently selected from the group consisting of H and C_{1-4} alkyl.

In some embodiments:

Ar¹ is 2-pyridyl, optionally substituted by 1 or 2 independently selected R¹ groups;

Ar² is phenyl, optionally substituted by 1 or 2 independently selected R² groups;

each R¹ is independently selected from the group consisting of halo, NO₂, OR^{a1}, and C_{1-6} alkyl;

each R² is independently selected from the group consisting of halo, NO₂, OR^{a2}, and C_{1-6} alkyl;

each R^{a1} is independently selected from the group consisting of H and C_{1-4} alkyl; and each R^{a2} is independently selected from the group consisting of H and C_{1-4} alkyl.

In some embodiments:

Ar¹ is 2-pyridyl, optionally substituted by 1 or 2 independently selected R¹ groups;

Ar² is phenyl, optionally substituted by 1 or 2 independently selected R² groups;

each R¹ is independently selected from the group consisting of chloro, fluoro, NO₂, OH, methoxy, and methyl;

each R² is independently selected from the group consisting of chloro, fluoro, NO₂, OH, methoxy, and methyl;

each R^{a1} is independently selected from the group consisting of H and methyl; and each R^{a2} is independently selected from the group consisting of H and methyl.

In some embodiments, the compound of Formula I is a compound of Formula Ia:

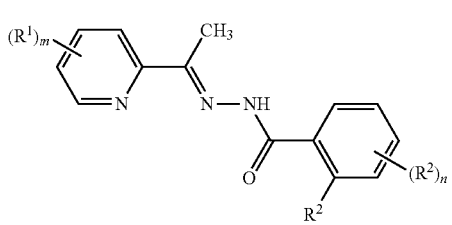

or a pharmaceutically acceptable salt thereof, wherein:

m is 0, 1, 2, 3, or 4; and n is 0, 1, 2, 3, or 4.

In some embodiments, the compound of Formula I is a compound of Formula Ib:

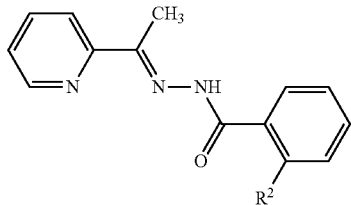

or a pharmaceutically acceptable salt thereof.

In some embodiments, the compound of Formula I is a compound of Formula Ic:

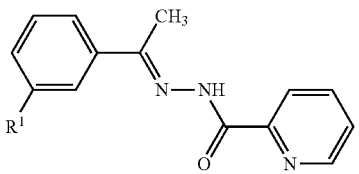

or a pharmaceutically acceptable salt thereof.

The present application further provides a pharmaceutical composition comprising a compound of Formula I, or a pharmaceutically acceptable salt thereof, and a pharmaceutically acceptable carrier.

The present application further provides a method of treating a cancer selected from the group consisting of breast cancer, cancer of the head and neck, thyroid cancer, and colorectal cancer, comprising administering to a patient in need thereof a therapeutically effective amount of a compound of Formula I, or a pharmaceutically acceptable salt thereof.

The present application further provides a method of reducing metastasis of a cancer in a patient, wherein the cancer is selected from the group consisting of breast cancer, cancer of the head and neck, thyroid cancer, and colorectal cancer, the method comprising administering to a patient in need thereof a therapeutically effective amount of a compound of Formula I, or a pharmaceutically acceptable salt thereof.

In some embodiments, the cancer is associated with overexpression of G3BP2. In some embodiments, the cancer is associated with overexpression of ZEB1. In some embodiments, the cancer is associated with overexpression of G3BP2 and overexpression of ZEB1. In some embodiments, the cancer is associated with overexpression of G3BP1. In some embodiments, the cancer is associated with overexpression of G3BP1 and overexpression of G3BP2. In some embodiments, the cancer is associated with overexpression of G3BP1, overexpression of G3BP2, and overexpression of ZEB1.

The present application further provides a method of treating a cancer in a patient, the method comprising:

i) identifying the patient as having a cancer associated with overexpression of G3BP2; and ii) administering to the patient a therapeutically effective amount a compound of Formula I, or a pharmaceutically acceptable salt thereof.

The present application further provides a method of treating a cancer in a patient, the method comprising:
  i) identifying the patient as having a cancer associated with overexpression of ZEB1; and
  ii) administering to the patient a therapeutically effective amount a compound of Formula I, or a pharmaceutically acceptable salt thereof.

The present application further provides a method of treating a cancer in a patient, the method comprising:
  i) identifying the patient as having a cancer associated with overexpression of G3BP2 and overexpression of ZEB1; and
  ii) administering to the patient a therapeutically effective amount a compound of Formula I, or a pharmaceutically acceptable salt thereof.

The present application further provides a method of treating a cancer in a patient, the method comprising:
  i) identifying the patient as having a cancer associated with overexpression of G3BP1; and
  ii) administering to the patient a therapeutically effective amount a compound of Formula I, or a pharmaceutically acceptable salt thereof.

The present application further provides a method of treating a cancer in a patient, the method comprising:
  i) identifying the patient as having a cancer associated with overexpression of G3BP1 and overexpression of G3BP2; and
  ii) administering to the patient a therapeutically effective amount a compound of Formula I, or a pharmaceutically acceptable salt thereof.

The present application further provides a method of treating a cancer in a patient, the method comprising:
  i) identifying the patient as having a cancer associated with overexpression of G3BP1, overexpression of G3BP2, and overexpression of ZEB1; and
  ii) administering to the patient a therapeutically effective amount a compound of Formula I, or a pharmaceutically acceptable salt thereof.

In some embodiments, the cancer is selected from the group consisting of breast cancer, cancer of the head and neck, thyroid cancer, and colorectal cancer. In some embodiments, the cancer is breast cancer.

The present application further provides a method of inhibiting G3BP2 in a cell, comprising contacting the cell with an effective amount of a compound of Formula I, or a pharmaceutically acceptable salt thereof.

The present application further provides a method of inhibiting ZEB1 in a cell, comprising contacting the cell with an effective amount of a compound of Formula I, or a pharmaceutically acceptable salt thereof.

The present application further provides a method of inhibiting G3BP2 and ZEB1 in a cell, comprising contacting the cell with an effective amount of a compound of Formula I, or a pharmaceutically acceptable salt thereof.

The present application further provides a method of inhibiting G3BP1 in a cell, comprising contacting the cell with an effective amount of a compound of Formula I, or a pharmaceutically acceptable salt thereof.

The present application further provides a method of inhibiting G3BP1 and G3BP2 in a cell, comprising contacting the cell with an effective amount of a compound of Formula I, or a pharmaceutically acceptable salt thereof.

The present application further provides a method of inhibiting G3BPL. G3BP2, and ZEB1 in a cell, comprising contacting the cell with an effective amount of a compound of Formula I, or a pharmaceutically acceptable salt thereof.

The present application further provides a method of inhibiting growth of a cancer stem cell, comprising contacting the cancer stem cell with an effective amount of a compound of Formula I, or a pharmaceutically acceptable salt thereof.

In some embodiments, the cancer stem cell is selected from the group consisting of a breast cancer stem cell, a cancer of the head and neck stem cell, a thyroid cancer stem cell, and a colorectal cancer stem cell. In some embodiments, the cancer stem cell is a breast cancer stem cell. In some embodiments, the cancer stem cell is associated with overexpression of G3BP2. In some embodiments, the cancer stem cell is associated with overexpression of ZEB1. In some embodiments, the cancer stem cell is associated with overexpression of G3BP2 and overexpression of ZEB1. In some embodiments, the cancer stem cell is associated with overexpression of G3BP1. In some embodiments, the cancer stem cell is associated with overexpression of G3BP1 and overexpression of G3BP2. In some embodiments, the cancer stem cell is associated with overexpression of G3BP1, overexpression of G3BP2, and overexpression of ZEB1. In some embodiments, the cancer stem cell is resistant to treatment with a chemotherapeutic agent.

The present application further provides a method of treating inflammation, comprising administering to a patient in need thereof a therapeutically effective amount of a compound of Formula I, or a pharmaceutically acceptable salt thereof. In some embodiments, the inflammation is associated with one or more NF-κB target genes. In some embodiments, the inflammation is associated with a gene selected from the group consisting of IL1a, IL6, IL6, and TNFα.

The present application further provides a method of treating a cancer selected from the group consisting of breast cancer, cancer of the head and neck, thyroid cancer, and colorectal cancer, comprising administering to a patient in need thereof a therapeutically effective amount of a compound selected from the group consisting of:

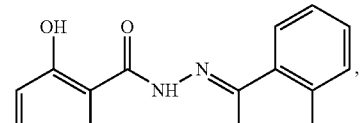

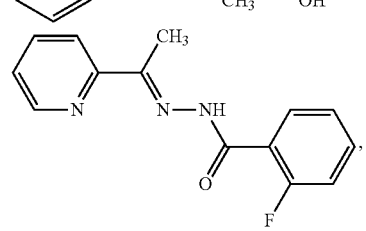

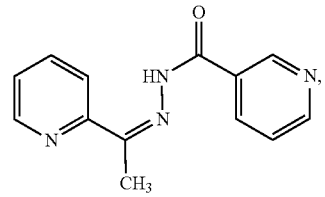

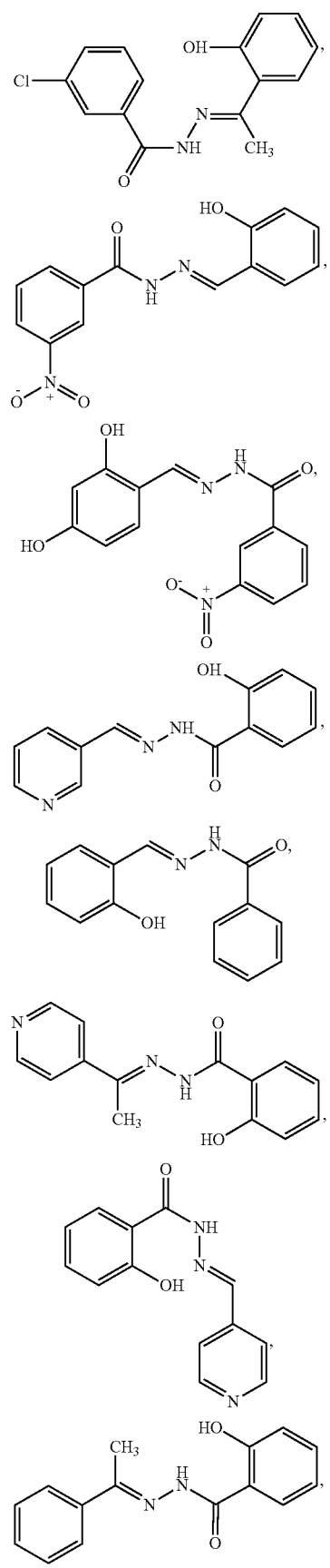
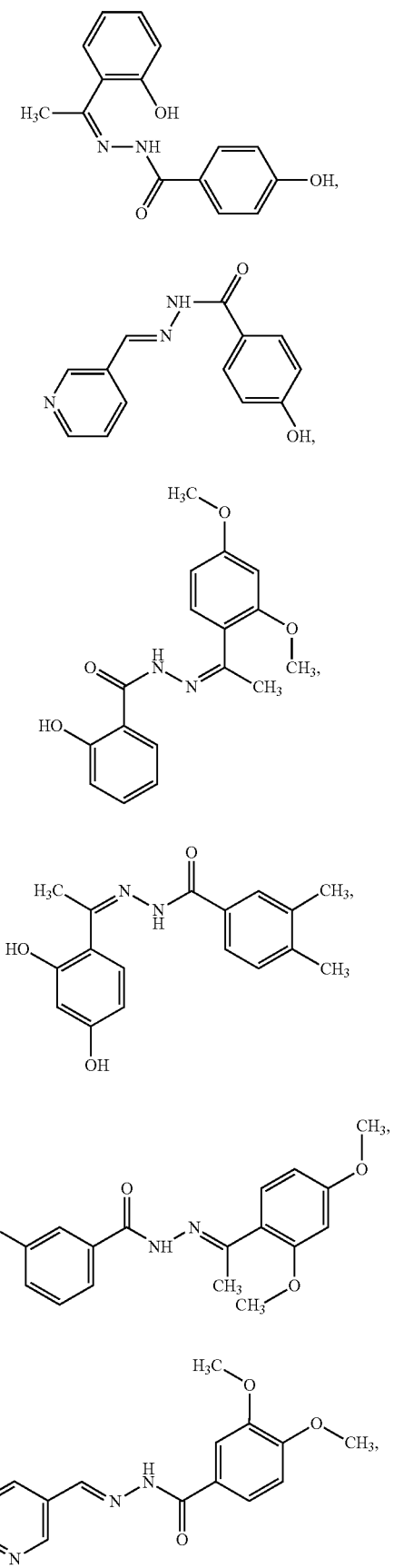

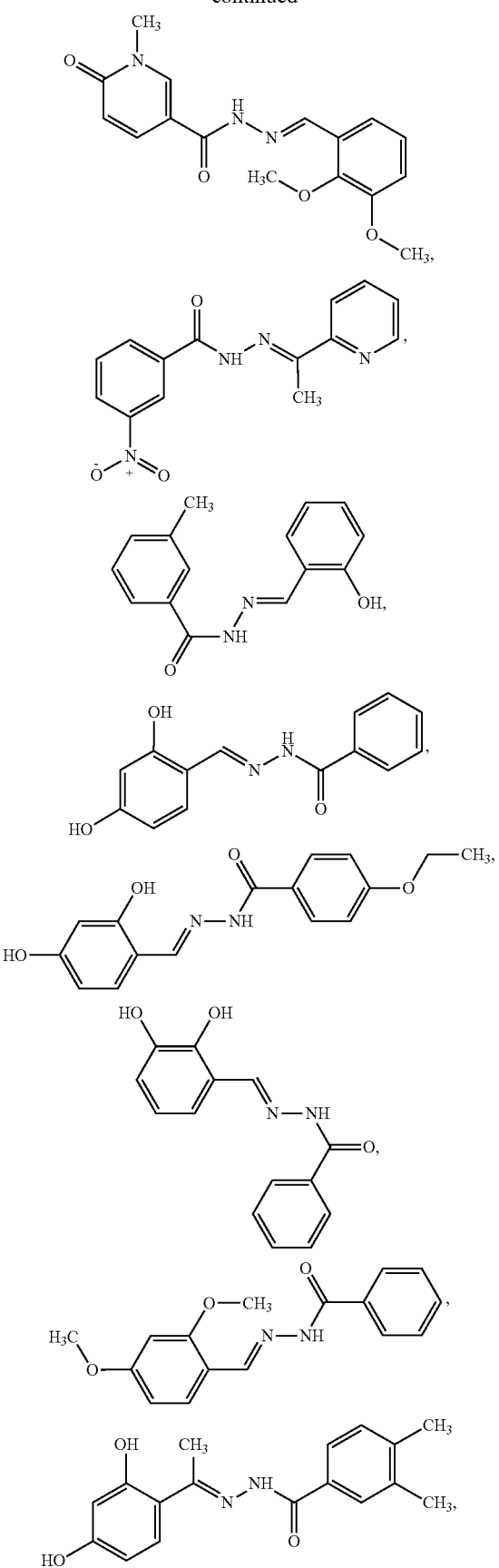

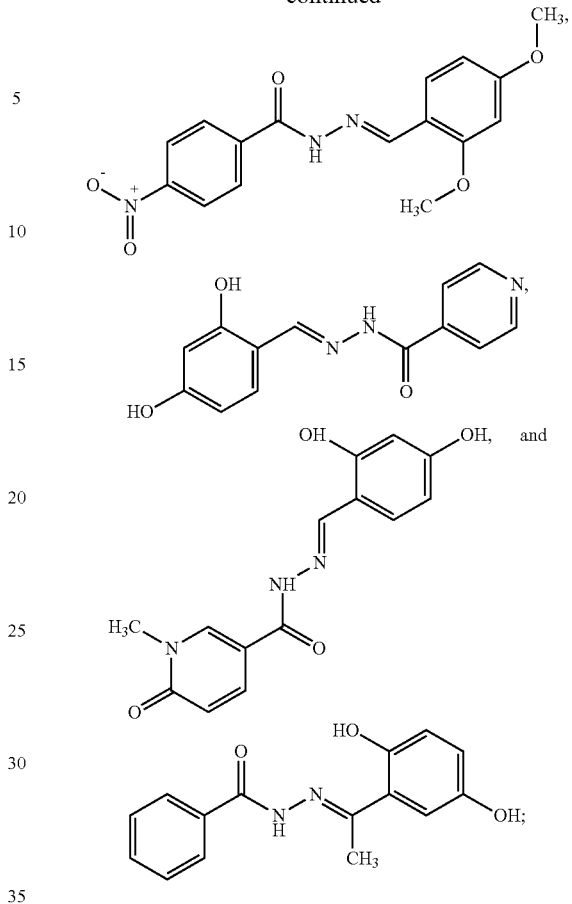

or a pharmaceutically acceptable salt thereof (these compounds are also provided in Table 1 below).

The present application further provides a method of reducing metastasis of a cancer in a patient, wherein the cancer is selected from the group consisting of breast cancer, cancer of the head and neck, thyroid cancer, and colorectal cancer, the method comprising administering to a patient in need thereof a therapeutically effective amount of a compound selected from Table 1, or a pharmaceutically acceptable salt thereof.

In some embodiments, the cancer is associated with overexpression of G3BP2. In some embodiments, the cancer is associated with overexpression of ZEB1. In some embodiments, the cancer is associated with overexpression of G3BP2 and overexpression of ZEB1. In some embodiments, the cancer is associated with overexpression of G3BP1. In some embodiments, the cancer is associated with overexpression of G3BP1 and overexpression of G3BP2. In some embodiments, the cancer is associated with overexpression of G3BP1, overexpression of G3BP2, and overexpression of ZEB1.

The present application further provides a method of treating a cancer in a patient, the method comprising:
i) identifying the patient as having a cancer associated with overexpression of G3BP2; and
ii) administering to the patient a therapeutically effective amount of a compound selected from Table 1, or a pharmaceutically acceptable salt thereof.

The present application further provides a method of treating a cancer in a patient, the method comprising:

i) identifying the patient as having a cancer associated with overexpression of ZEB1; and ii) administering to the patient a therapeutically effective amount of a compound selected from Table 1, or a pharmaceutically acceptable salt thereof.

The present application further provides a method of treating a cancer in a patient, the method comprising:

i) identifying the patient as having a cancer associated with overexpression of G3BP2 and overexpression of ZEB1; and ii) administering to the patient a therapeutically effective amount of a compound selected from Table 1, or a pharmaceutically acceptable salt thereof.

The present application further provides a method of treating a cancer in a patient, the method comprising:

i) identifying the patient as having a cancer associated with overexpression of G3BP1; and ii) administering to the patient a therapeutically effective amount of a compound selected from Table 1, or a pharmaceutically acceptable salt thereof.

The present application further provides a method of treating a cancer in a patient, the method comprising:

i) identifying the patient as having a cancer associated with overexpression of G3BP1 and overexpression of G3BP2; and ii) administering to the patient a therapeutically effective amount of a compound selected from Table 1, or a pharmaceutically acceptable salt thereof.

The present application further provides a method of treating a cancer in a patient, the method comprising:

i) identifying the patient as having a cancer associated with overexpression of G3BP1, overexpression of G3BP2, and overexpression of ZEB1; and ii) administering to the patient a therapeutically effective amount of a compound selected from Table 1, or a pharmaceutically acceptable salt thereof.

In some embodiments, the cancer is selected from the group consisting of breast cancer, cancer of the head and neck, thyroid cancer, and colorectal cancer. In some embodiments, the cancer is breast cancer.

The present application further provides a method of inhibiting G3BP2 in a cell, comprising contacting the cell with an effective amount of a compound selected from Table 1, or a pharmaceutically acceptable salt thereof.

The present application further provides a method of inhibiting ZEB1 in a cell, comprising contacting the cell with an effective amount of a compound selected from Table 1, or a pharmaceutically acceptable salt thereof.

The present application further provides a method of inhibiting G3BP2 and ZEB1 in a cell, comprising contacting the cell with an effective amount of a compound selected from Table 1, or a pharmaceutically acceptable salt thereof.

The present application further provides a method of inhibiting G3BP1 in a cell, comprising contacting the cell with an effective amount of a compound selected from Table 1, or a pharmaceutically acceptable salt thereof.

The present application further provides a method of inhibiting G3BP1 and G3BP2 in a cell, comprising contacting the cell with an effective amount of a compound selected from Table 1, or a pharmaceutically acceptable salt thereof.

The present application further provides a method of inhibiting G3BP1, G3BP2, and ZEB1 in a cell, comprising contacting the cell with an effective amount of a compound selected from Table 1, or a pharmaceutically acceptable salt thereof.

The present application further provides a method of inhibiting growth of a cancer stem cell, comprising contacting the cancer stem cell with an effective amount of a compound selected from Table 1, or a pharmaceutically acceptable salt thereof.

In some embodiments, the cancer stem cell is selected from the group consisting of a breast cancer stem cell, a cancer of the head and neck stem cell, a thyroid cancer stem cell, and a colorectal cancer stem cell. In some embodiments, the cancer stem cell is a breast cancer stem cell. In some embodiments, the cancer stem cell is associated with overexpression of G3BP2. In some embodiments, the cancer stem cell is associated with overexpression of ZEB1. In some embodiments, the cancer stem cell is associated with overexpression of G3BP2 and overexpression of ZEB1. In some embodiments, the cancer stem cell is associated with overexpression of G3BP1. In some embodiments, the cancer stem cell is associated with overexpression of G3BP1 and overexpression of G3BP2. In some embodiments, the cancer stem cell is associated with overexpression of G3BP1, overexpression of G3BP2, and overexpression of ZEB1. In some embodiments, the cancer stem cell is resistant to treatment with a chemotherapeutic agent.

The present application further provides a method of treating inflammation, comprising administering to a patient in need thereof a therapeutically effective amount of a compound selected from Table 1, or a pharmaceutically acceptable salt thereof.

In some embodiments, the inflammation is associated with one or more NF-κB target genes. In some embodiments, the inflammation is associated with a gene selected from the group consisting of IL1a, IL6, IL6, and TNFα.

In some embodiments, the compound is selected from the group consisting of:

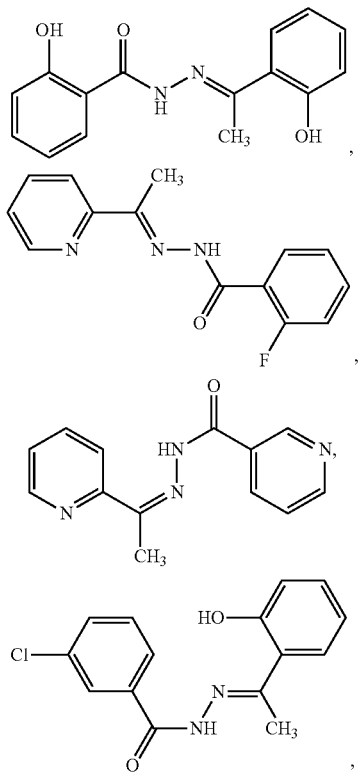

,

-continued

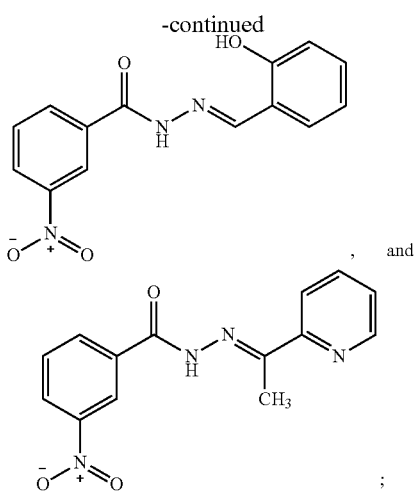

, and or a pharmaceutically acceptable salt thereof.

In some embodiments, the compound is selected from the group consisting of:

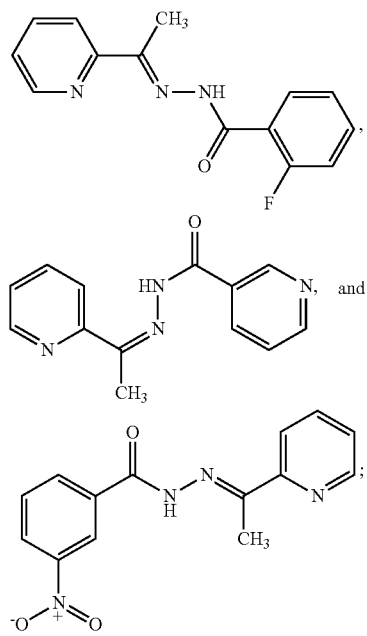

or a pharmaceutically acceptable salt thereof.

The present application further provides a method of identifying an inhibitor of a cancer stem cell, comprising:

i) contacting a cancer stem cell with a test compound and a non-lethal dose of a chemotherapeutic agent;

ii) contacting a non-cancerous cell with a test compound; and iii) measuring the viability of the cancer stem cell and the viability of the non-cancerous cell;

wherein the test compound is identified as an inhibitor of a cancer stem cell if the viability of the cancer stem cell is reduced by at least 90% after contacting with the test compound and the chemotherapeutic agent compared to the viability of the cancer stem cell prior to contacting with the test compound and the chemotherapeutic agent.

In some embodiments, the viability of the non-cancerous cell is substantially unaffected compared to the viability of the non-cancerous cell prior to contacting with the test compound and the chemotherapeutic agent.

In some embodiments, the method further comprises identifying an intracellular protein that binds to the test compound, the method comprising:

i) forming a conjugate of the test compound and a nanoparticle;

ii) contacting the conjugate with the intracellular protein;

iii) contacting the intracellular protein with a non-conjugated nanoparticle; and iv) analyzing the binding of the intracellular protein to the conjugate and the binding of the intracellular protein to the non-conjugated nanoparticle;

wherein the intracellular protein is identified as bound to the test compound if the intracellular protein substantially binds to the conjugate and does not substantially bind to the non-conjugated nanoparticle.

In some embodiments, the analyzing comprises separating a bound intracellular protein from an unbound intracellular protein using electrophoresis. In some embodiments, the method further comprises analyzing the bound intracellular protein by mass spectrometry.

In some embodiments, the chemotherapeutic agent is a taxane. In some embodiments, the taxane is paclitaxel.

In some embodiments, the cancer stem cell is associated with overexpression of G3BP2. In some embodiments, the cancer stem cell is associated with overexpression of ZEB1. In some embodiments, the cancer stem cell is associated overexpression of G3BP2 and overexpression of ZEB1. In some embodiments, the cancer stem cell is associated with overexpression of G3BP1. In some embodiments, the cancer stem cell is associated with overexpression of G3BP1 and overexpression of G3BP2. In some embodiments, the cancer stem cell is associated with overexpression of G3BP1, overexpression of G3BP2, and overexpression of ZEB1. In some embodiments, the cancer stem cell is resistant to treatment with a chemotherapeutic agent.

The details of one or more embodiments of the invention are set forth in the accompanying drawings and the description below. Other features, objects, and advantages of the invention will be apparent from the description and drawings, and from the claims. All publications, patent applications, patents, sequences, database entries, and other references mentioned herein are incorporated by reference in their entirety. In case of conflict, the present specification, including definitions, will control.

DESCRIPTION OF DRAWINGS

FIG. 7A shows SART3 protein pull down with G3BP2 recombinant protein using magnetic beads. Mass spectrometry analysis revealed G3BP2-SART3 interaction in HEK-293T cell lysates (total peptide matched by sequence: 7, unique peptide matched: 7).

DETAILED DESCRIPTION

Figure 1A:
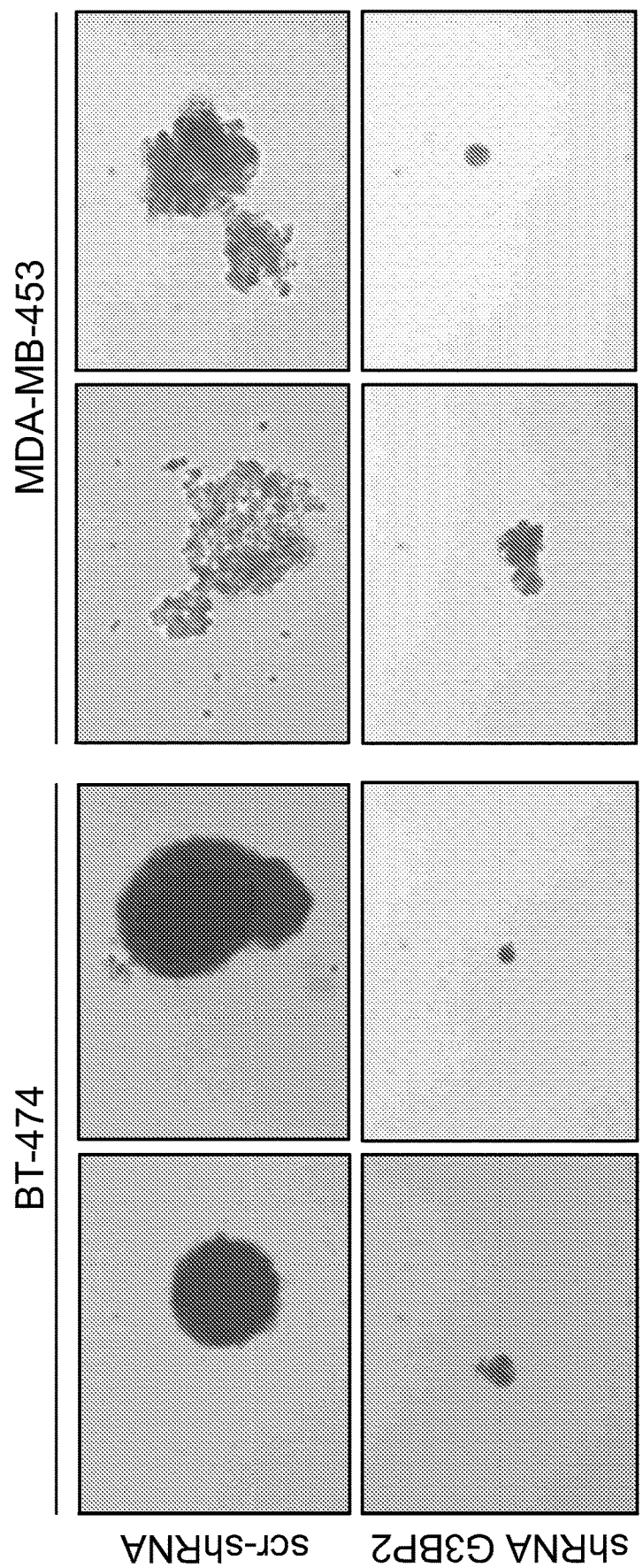
FIG. 1A shows that knock down of G3BP2 inhibits mammosphere formation in cell lines BT-474 and MDA-MB-453.

The assumption that tumors are hierarchically organized, with tumorigenic cancer stem cells (CSCs) occupying the apex of the hierarchy and their non-tumorigenic non-CSC progeny occupying subordinate positions, has led to the hypothesis that CSC are the most critical therapeutic targets within breast tumors. Despite the observation of this hierarchical organization for many solid tumors (see e.g., Patrawala et al., *Oncogene,* 2006, 25, 1696-1708; Al-Hajj et al., *Proceedings of the National Academy of Sciences in the United States of America,* 2003, 100, 3983-3988; and Chan et al., *Proceedings of the National Academy of Sciences in the United States of America,* 2009, 106, 14016-14021), it is believed that a CSC may represent a plastic phenotype (see e.g., Marjanovic et al., *Clinical Chemistry,* 2013, 59, 168-179). In some breast tumors, the CSC phenotype may be closely linked to cells undergoing an epithelial-to-mesenchymal transition (EMT) (see e.g., Mani et al., *Cell,* 2008, 133, 705-715 and Morel et al., *PloS one,* 2008, 3, e2888). This may have clinical implications, in that non-CSCs and CSCs alike may be equally important therapeutic targets. However, little is known about the molecular mechanisms that govern the ability of non-CSCs to transition to the CSC state and back, and understanding the molecular triggers that underlie this plasticity may provide insights for therapeutically targeting the CSC state.

It is appreciated that certain features of the present application which are, for clarity, described in the context of separate embodiments can also be provided in combination in a single embodiment. Conversely, various features of the present application which are, for brevity, described in the context of a single embodiment can also be provided separately or in any suitable subcombination.

Compounds and Pharmaceutical Compositions

The present application provides, inter alia, a compound of Formula I:

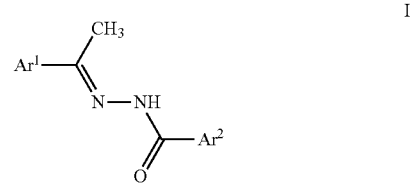

or a pharmaceutically acceptable salt thereof, wherein:

$Ar^1$ is selected from the group consisting of 2-pyridyl, 3-pyridyl, and phenyl, each of which may be optionally substituted by 1, 2, 3, or 4 independently selected $R^1$ groups; and $Ar^2$ is selected from the group consisting of 2-pyridyl, 3-pyridyl, and phenyl, each of which may be optionally substituted by 1, 2, 3, or 4 independently selected $R^2$ groups;

wherein at least one of $Ar^1$ and $Ar^2$ is 2-pyridyl or 3-pyridyl;

each $R^1$ is independently selected from the group consisting of halo, $NO_2$, $OR^{a1}$, $C_{1-6}$ alkyl, $C_{2-6}$ alkenyl, and $C_{2-6}$ alkynyl;

each $R^2$ is independently selected from the group consisting of halo, $NO_2$, $OR^{a2}$, $C_{1-6}$ alkyl, $C_{2-6}$ alkenyl, and $C_{2-6}$ alkynyl; and each $R^{a1}$ is independently selected from the group consisting of H and $C_{1-4}$ alkyl; and each $R^{a2}$ is independently selected from the group consisting of H and $C_{1-4}$ alkyl.

In some embodiments, the compound is not a compound selected from the group consisting of:

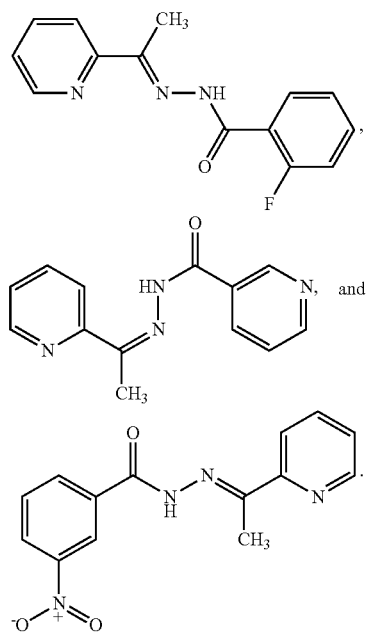

In some embodiments, Ar¹ is 2-pyridyl, optionally substituted by 1, 2, 3, or 4 independently selected R¹ groups. In some embodiments, Ar¹ is 3-pyridyl, optionally substituted by 1, 2, 3, or 4 independently selected R¹ groups. In some embodiments, Ar² is phenyl, optionally substituted by 1, 2, 3, or 4 independently selected R¹ groups.

In some embodiments, Ar² is 2-pyridyl, optionally substituted by 1, 2, 3, or 4 independently selected R² groups. In some embodiments, Ar² is 3-pyridyl, optionally substituted by 1, 2, 3, or 4 independently selected R² groups. In some embodiments, Ar² is phenyl, optionally substituted by 1, 2, 3, or 4 independently selected R² groups.

In some embodiments, each R¹ is independently selected from the group consisting of halo, $NO_2$, $OR^{a1}$, and $C_{1-6}$ alkyl. In some embodiments, each R¹ is independently selected from the group consisting of chloro, fluoro, $NO_2$, OH, methoxy, and methyl.

In some embodiments, each R² is independently selected from the group consisting of halo, $NO_2$, $OR^{a1}$, and $C_{1-6}$ alkyl. In some embodiments, each R² is independently selected from the group consisting of chloro, fluoro, $NO_2$, OH, methoxy, and methyl.

In some embodiments:

Ar¹ is 2-pyridyl, optionally substituted by 1, 2, 3, or 4 independently selected R¹ groups;

Ar² is phenyl, optionally substituted by 1, 2, 3, or 4 independently selected R² groups;

each R¹ is independently selected from the group consisting of halo, $NO_2$, $OR^a$, and $C_{1-6}$ alkyl;

each R² is independently selected from the group consisting of halo, $NO_2$, $OR^{a2}$, and $C_{1-6}$ alkyl;

each $R^{a1}$ is independently selected from the group consisting of H and $C_{1-4}$ alkyl; and each $R^{a2}$ is independently selected from the group consisting of H and $C_{1-4}$ alkyl.

In some embodiments:

Ar¹ is 2-pyridyl, optionally substituted by 1 or 2 independently selected R¹ groups;

Ar² is phenyl, optionally substituted by 1 or 2 independently selected R² groups;

each R¹ is independently selected from the group consisting of halo, $NO_2$, $OR^{a1}$, and $C_{1-6}$ alkyl;

each R² is independently selected from the group consisting of halo, $NO_2$, $OR^{a2}$, and $C_{1-6}$ alkyl;

each $R^{a1}$ is independently selected from the group consisting of H and $C_{1-4}$ alkyl; and each R¹ is independently selected from the group consisting of H and $C_{1-4}$ alkyl.

In some embodiments:

Ar¹ is 2-pyridyl, optionally substituted by 1 or 2 independently selected R¹ groups;

Ar² is phenyl, optionally substituted by 1 or 2 independently selected R² groups;

each R¹ is independently selected from the group consisting of chloro, fluoro, $NO_2$, OH, methoxy, and methyl;

each R² is independently selected from the group consisting of chloro, fluoro, $NO_2$, OH, methoxy, and methyl;

each $R^{a1}$ is independently selected from the group consisting of H and methyl; and each $R^{a2}$ is independently selected from the group consisting of H and methyl.

In some embodiments, the compound of Formula I is a compound of Formula Ia:

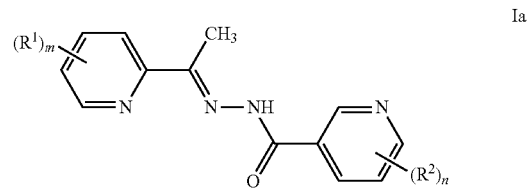

or a pharmaceutically acceptable salt thereof, wherein:

m is 0, 1, 2, 3, or 4; and n is 0, 1, 2, 3, or 4.

In some embodiments, the compound of Formula I is a compound of Formula Ib:

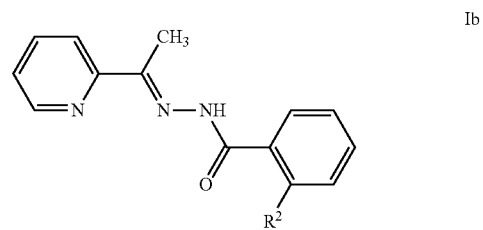

or a pharmaceutically acceptable salt thereof.

In some embodiments, the compound of Formula I is a compound of Formula Ic:

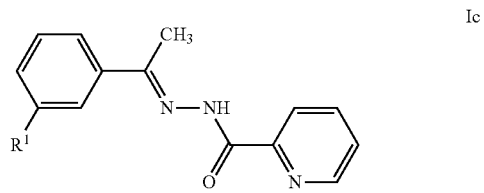

or a pharmaceutically acceptable salt thereof.

Reactions for preparing the compounds provided herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3rd Ed., Wiley & Sons, Inc., New York (1999).

Reactions can be monitored according to any suitable method known in the art. For example, product formation can be monitored by spectroscopic means, such as nuclear magnetic resonance spectroscopy (e.g., ¹H or ¹³C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms. In some embodiments, the alkyl group is a methyl group.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, "halo" refers to fluoro, chloro, bromo, or iodo. In some embodiments, the halo is selected from the group consisting of fluoro, chloro, and bromo. In some embodiments, the halo is fluoro or chloro.

At certain places, the definitions or embodiments refer to specific rings (e.g., a phenyl ring or a pyridine ring). Unless otherwise indicated, these rings can be attached to any ring member provided that the valency of the atom is not exceeded. For example, a phenyl ring may be attached at any position of the ring, whereas a 3-pyridyl ring (i.e., a 3-pyridine ring) is attached at the 3-position.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g., hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pyroglutamic acid, gulonic acid, pentanoic acid, hexanoic acid, heptanoic acid, octanoic acid, nonanoic acid, and decanoic acid. Also included are organic diacids such as malonic, fumaric and maleic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds provided herein, or pharmaceutically acceptable salts thereof, are substantially isolated. As used herein, the term "substantially isolated" refers to a compound that is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 96%, at least about 97%, at least about 98%, or at least about 99% by weight of the compounds provided herein, or pharmaceutically acceptable salt thereof. Methods for isolating compounds and their salts are routine in the art.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like.

The pharmaceutically acceptable salts provided herein include the conventional non-toxic salts of the parent compound formed, for example, from non-toxic inorganic or organic acids. The pharmaceutically acceptable salts provided herein can be synthesized from the parent compound which contains a basic or acidic moiety by conventional chemical methods. Generally, such salts can be prepared, for example, by reacting the free acid or base forms of these compounds with a stoichiometric amount of the appropriate base or acid in water or in an organic solvent, or in a mixture of the two. Non-aqueous media which include, but are not limited to, ether, ethyl acetate, alcohols (e.g., methanol, ethanol, isopropanol, or butanol), or acetonitrile (MeCN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977). Conventional methods for preparing salt forms are described, for example, in *Handbook of Pharmaceutical Salts: Properties, Selection, and Use*, Wiley-VCH, 2002.

The present application further provides a pharmaceutical composition comprising a compound of Formula I, or a pharmaceutically acceptable salt thereof, and at least one pharmaceutically acceptable carrier. The present application further provides a pharmaceutical composition comprising a compound provided in Table 1, or a pharmaceutically acceptable salt thereof, and at least one pharmaceutically acceptable carrier. When employed as pharmaceuticals, the compounds provided herein, or pharmaceutically acceptable salts thereof, can be administered in the form of pharmaceutical compositions; thus, the methods described herein can include administering pharmaceutical compositions provided herein.

These compositions can be prepared as described herein or elsewhere, and can be administered by a variety of routes, depending upon whether local or systemic treatment is desired and upon the area to be treated. Administration may be, for example, oral or parenteral. Parenteral administration may include, but is not limited to intravenous, intraarterial, subcutaneous, intraperitoneal, intramuscular injection or infusion; or intracranial, (e.g., intrathecal, intraocular, or intraventricular) administration. Parenteral administration can be in the form of a single bolus dose, or may be, for example, by a continuous perfusion pump. Conventional pharmaceutical carriers, aqueous, powder or oily bases, thickeners and the like may be necessary or desirable.

In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

Some examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or any combination thereof.

The active compounds or salts (e.g., a compound of Formula I, or a pharmaceutically acceptable salt thereof, a compound provided in Table 1, or a pharmaceutically acceptable salt thereof) can be effective over a wide dosage range and are generally administered in a pharmaceutically effective amount. It will be understood, however, that the amount of the compound or salt actually administered and the schedule of administration will usually be determined by a physician, according to the relevant circumstances, including the condition to be treated, the chosen route of administration, the actual compound administered, the age, weight, and response of the individual subject, the severity of the subject's symptoms, and the like.

Methods of Treatment

The present application further provides methods of treating cancer or inflammation in a patient in need thereof. As used herein, the term "patient" refers to any animal, including mammals, for example, mice, rats, other rodents, rabbits, dogs, cats, swine, cattle, sheep, horses, primates, and humans. In some embodiments, the patient is a human. In some embodiments, the method comprises administering to the patient a therapeutically effective amount of a compound of Formula I, or a pharmaceutically acceptable salt thereof; or a compound provided in Table 1, or a pharmaceutically acceptable salt thereof.

TABLE 1

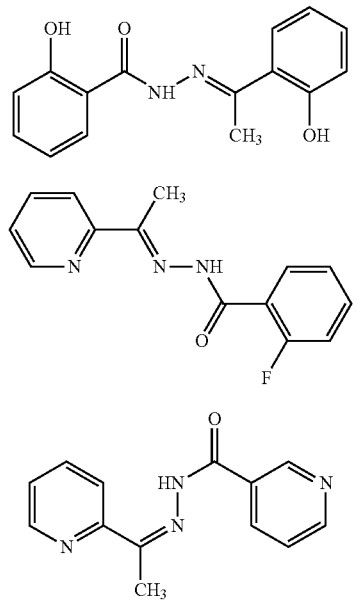

TABLE 1-continued
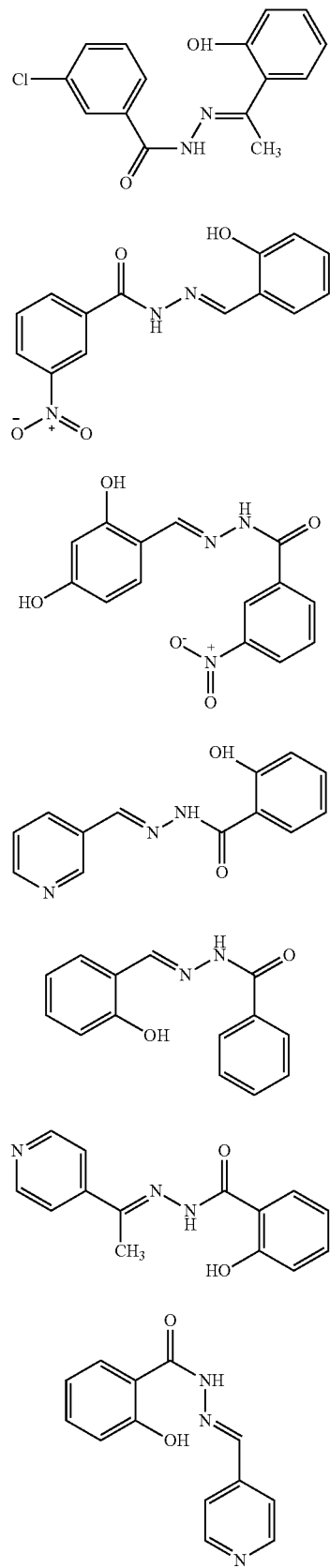
TABLE 1-continued
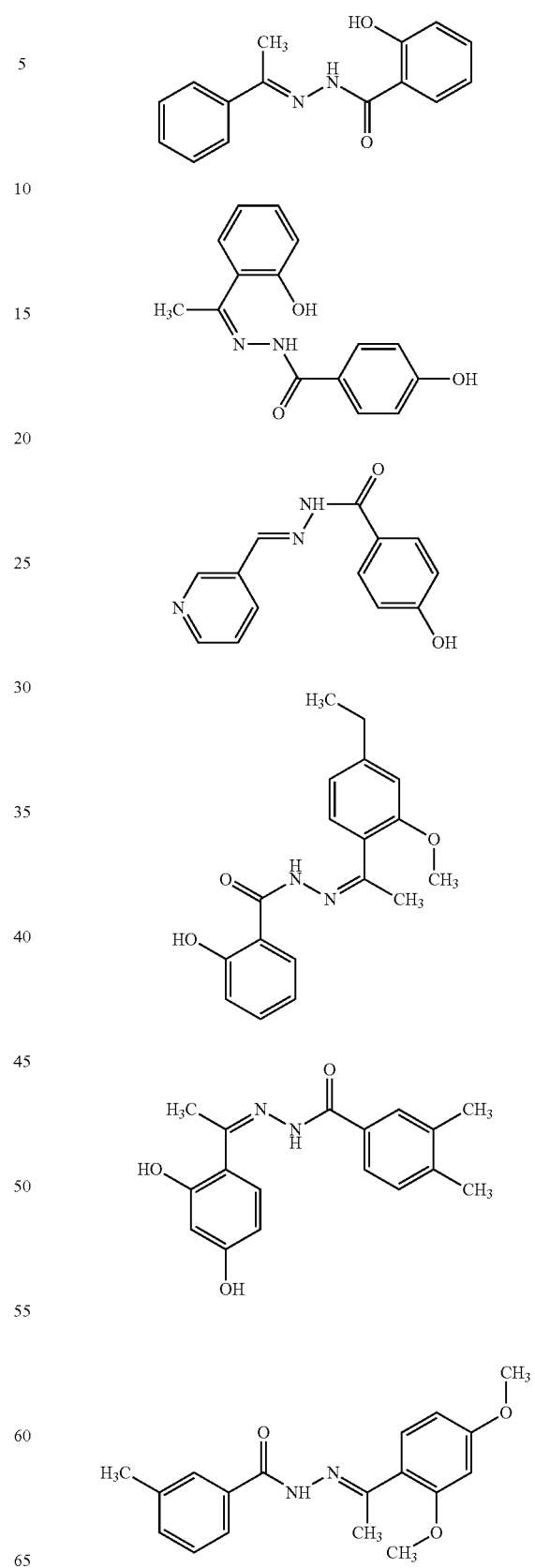

TABLE 1-continued

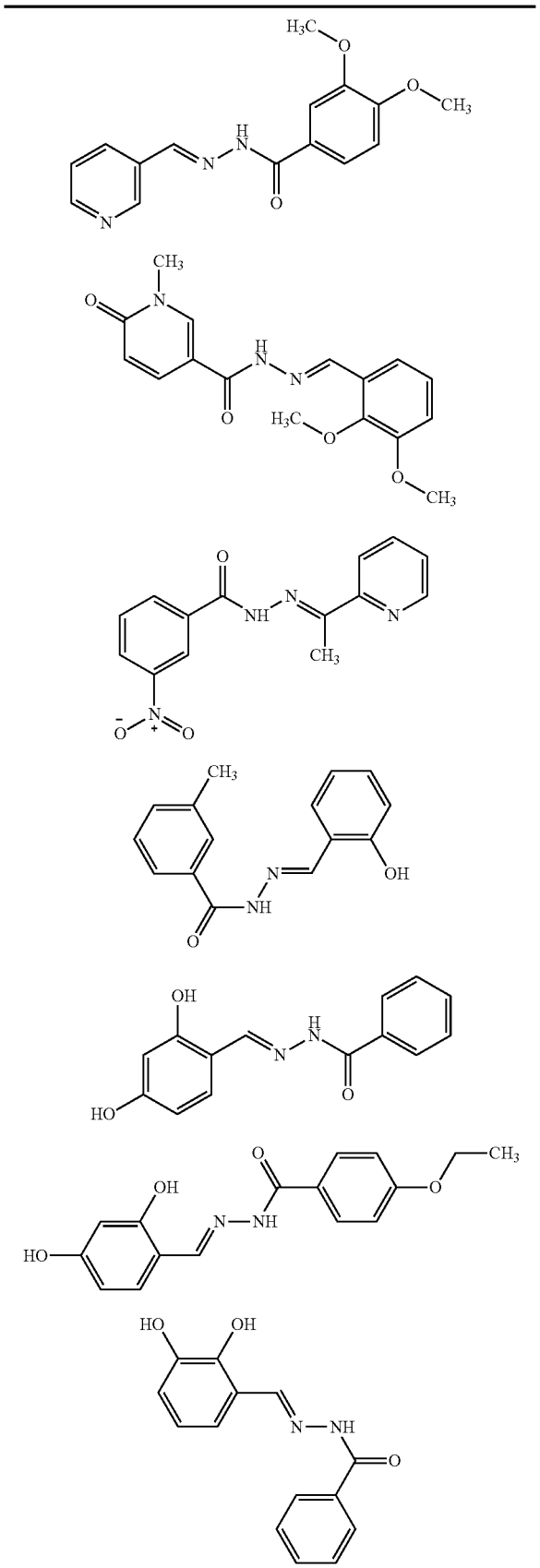

TABLE 1-continued

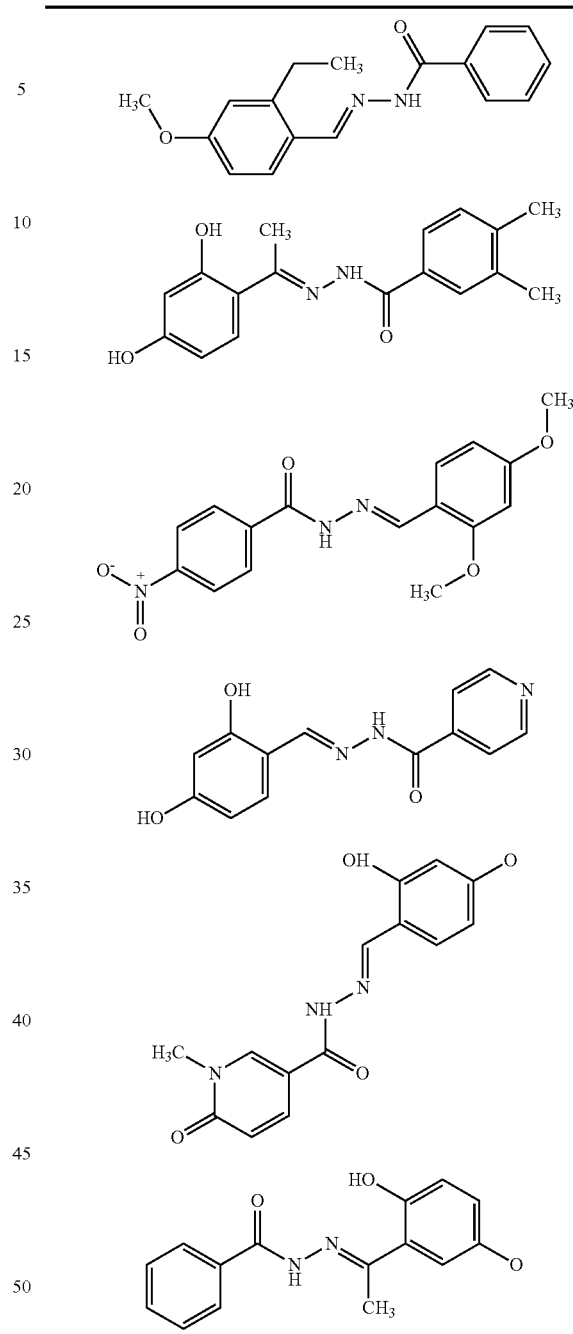

In some embodiments, the method comprises administering to the patient a therapeutically effective amount of a compound of Formula I, or a pharmaceutically acceptable salt thereof. In some embodiments, the method comprises administering to the patient a therapeutically effective amount of a compound provided in Table 1, or a pharmaceutically acceptable salt thereof.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or reducing or alleviating one or more symptoms of the disease.

In some embodiments, the present application provides a method of treating a cancer selected from the group consisting of breast cancer, glioblastoma, cancer of the head and neck, thyroid cancer, and colorectal cancer, comprising administering to a patient in need thereof a therapeutically effective amount of a compound of Formula I, or a pharmaceutically acceptable salt thereof; or a compound provided in Table 1, or a pharmaceutically acceptable salt thereof.

In some embodiments, the present application provides a method of treating a cancer selected from the group consisting of breast cancer, cancer of the head and neck, thyroid cancer, and colorectal cancer, comprising administering to a patient in need thereof a therapeutically effective amount of a compound of Formula I, or a pharmaceutically acceptable salt thereof; or a compound provided in Table 1, or a pharmaceutically acceptable salt thereof.

In some embodiments, the cancer is breast cancer. In some embodiments, the breast cancer is selected from the group consisting of non-invasive breast cancer, invasive breast cancer, recurrent breast cancer, and metastatic breast cancer. In some embodiments, the breast cancer is selected from the group consisting of ductal carcinoma in situ, invasive ductal carcinoma, triple negative breast cancer, inflammatory breast cancer, metastatic breast cancer, medullary carcinoma, tubular carcinoma, mucinous carcinoma, Paget disease of the breast or nipple, and HER2 positive breast cancer.

In some embodiments, the cancer is glioblastoma. In some embodiments, the cancer is breast cancer or glioblastoma.

The present application further provides a method of reducing metastasis of a cancer in a patient, wherein the cancer is selected from the group consisting of breast cancer, cancer of the head and neck, thyroid cancer, and colorectal cancer, the method comprising administering to a patient in need thereof a therapeutically effective amount of a compound of Formula I, or a pharmaceutically acceptable salt thereof; or a compound provided in Table 1, or a pharmaceutically acceptable salt thereof.

In some embodiments, the cancer is associated with overexpression of G3BP2. In some embodiments, the cancer is associated with overexpression of ZEB1. In some embodiments, the cancer is associated with overexpression of G3BP1. In some embodiments, the cancer is associated with overexpression of SART3. In some embodiments, the cancer is associated with overexpression of NANOG. In some embodiments, the cancer is associated with overexpression of OCT4. In some embodiments, the cancer is associated with overexpression of PD-L1. In some embodiments, the cancer is associated with overexpression of G3BP2 and overexpression of ZEB1. In some embodiments, the cancer is associated with overexpression of G3BP2, overexpression of ZEB1, and overexpression of G3BP1. In some embodiments, the cancer is associated with overexpression of G3BP2 and overexpression of ZEB1, overexpression of G3BP1, overexpression of SART3, overexpression of NANOG, overexpression of OCT4, or any combination thereof.

In some embodiments, the cancer is a breast cancer associated with overexpression of G3BP2. In some embodiments, the cancer is a breast cancer associated with overexpression of ZEB1. In some embodiments, the cancer is a breast cancer associated with overexpression of G3BP1. In some embodiments, the cancer is a breast cancer associated with overexpression of SART3. In some embodiments, the cancer is a breast cancer associated with overexpression of NANOG. In some embodiments, the cancer is a breast cancer associated with overexpression of OCT4. In some embodiments, the cancer is a breast cancer associated with overexpression of G3BP2 and overexpression of ZEB1. In some embodiments, the cancer is a breast cancer associated with overexpression of G3BP2, overexpression of ZEB1, and overexpression of G3BP1. In some embodiments, the cancer is a breast cancer associated with overexpression of G3BP2 and overexpression of ZEB1, overexpression of G3BP1, overexpression of SART3, overexpression of NANOG, overexpression of OCT4, or any combination thereof.

The present application further provides a method of treating a cancer in a patient, the method comprising:
i) identifying the patient as having a cancer associated with overexpression of G3BP2; and
ii) administering to the patient a therapeutically effective amount of a compound of Formula I, or a pharmaceutically acceptable salt thereof, or a compound provided in Table 1, or a pharmaceutically acceptable salt thereof.

The present application further provides a method of treating a cancer in a patient, the method comprising:
i) identifying the patient as having a cancer associated with overexpression of ZEB1; and
ii) administering to the patient a therapeutically effective amount of a compound of Formula I, or a pharmaceutically acceptable salt thereof, or a compound provided in Table 1, or a pharmaceutically acceptable salt thereof.

The present application further provides a method of treating a cancer in a patient, the method comprising:
i) identifying the patient as having a cancer associated with overexpression of G3BP1; and
ii) administering to the patient a therapeutically effective amount of a compound of Formula I, or a pharmaceutically acceptable salt thereof, or a compound provided in Table 1, or a pharmaceutically acceptable salt thereof.

The present application further provides a method of treating a cancer in a patient, the method comprising:
i) identifying the patient as having a cancer associated with overexpression of G3BP2 and overexpression of ZEB1; and
ii) administering to the patient a therapeutically effective amount of a compound of Formula I, or a pharmaceutically acceptable salt thereof; or a compound provided in Table 1, or a pharmaceutically acceptable salt thereof.

The present application further provides a method of treating a cancer in a patient, the method comprising:
i) identifying the patient as having a cancer associated with overexpression of G3BP2, overexpression of ZEB1, and overexpression of G3BP1; and
ii) administering to the patient a therapeutically effective amount of a compound of Formula I, or a pharmaceutically acceptable salt thereof, or a compound provided in Table 1, or a pharmaceutically acceptable salt thereof.

The present application further provides a method of treating a cancer in a patient, the method comprising:

i) identifying the patient as having a cancer associated with overexpression of SART3; and ii) administering to the patient a therapeutically effective amount of a compound of Formula I, or a pharmaceutically acceptable salt thereof; or a compound provided in Table 1, or a pharmaceutically acceptable salt thereof.

The present application further provides a method of treating a cancer in a patient, the method comprising:

i) identifying the patient as having a cancer associated with overexpression of NANOG; and ii) administering to the patient a therapeutically effective amount of a compound of Formula I, or a pharmaceutically acceptable salt thereof, or a compound provided in Table 1, or a pharmaceutically acceptable salt thereof.

The present application further provides a method of treating a cancer in a patient, the method comprising:

i) identifying the patient as having a cancer associated with overexpression of OCT4; and ii) administering to the patient a therapeutically effective amount of a compound of Formula I, or a pharmaceutically acceptable salt thereof, or a compound provided in Table 1, or a pharmaceutically acceptable salt thereof.

The present application further provides a method of treating a cancer in a patient, the method comprising:

i) identifying the patient as having a cancer associated with overexpression of G3BP2 and overexpression of ZEB1, overexpression of G3BP1, overexpression of SART3, overexpression of NANOG, overexpression of OCT4, or any combination thereof; and ii) administering to the patient a therapeutically effective amount of a compound of Formula I, or a pharmaceutically acceptable salt thereof; or a compound provided in Table 1, or a pharmaceutically acceptable salt thereof.

In some embodiments, the cancer is selected from the group consisting of breast cancer, cancer of the head and neck, thyroid cancer, and colorectal cancer. In some embodiments, the cancer is breast cancer. In some embodiments, the breast cancer is selected from the group consisting of non-invasive breast cancer, invasive breast cancer, recurrent breast cancer, and metastatic breast cancer. In some embodiments, the breast cancer is selected from the group consisting of ductal carcinoma in situ, invasive ductal carcinoma, triple negative breast cancer, inflammatory breast cancer, metastatic breast cancer, medullary carcinoma, tubular carcinoma, mucinous carcinoma, and Paget disease of the breast or nipple.

The present application further provides a method of inhibiting G3BP2 in a cell, comprising contacting the cell with an effective amount of a compound Formula I, or a pharmaceutically acceptable salt thereof; or a compound provided in Table 1, or a pharmaceutically acceptable salt thereof.

The present application further provides a method of inhibiting ZEB1 in a cell, comprising contacting the cell with an effective amount of a compound of Formula I, or a pharmaceutically acceptable salt thereof; or a compound provided in Table 1, or a pharmaceutically acceptable salt thereof.

The present application further provides a method of inhibiting G3BP1 in a cell, comprising contacting the cell with an effective amount of a compound Formula I, or a pharmaceutically acceptable salt thereof; or a compound provided in Table 1, or a pharmaceutically acceptable salt thereof.

The present application further provides a method of inhibiting G3BP2 and ZEB1 in a cell, comprising contacting the cell with an effective amount of a compound of Formula I, or a pharmaceutically acceptable salt thereof; or a compound provided in Table 1, or a pharmaceutically acceptable salt thereof. The present application further provides a method of inhibiting G3BP2, ZEB1, and G3BP1 in a cell, comprising contacting the cell with an effective amount of a compound of Formula I, or a pharmaceutically acceptable salt thereof, or a compound provided in Table 1, or a pharmaceutically acceptable salt thereof.

The present application further provides a method of inhibiting G3BP1 in a cell, comprising contacting the cell with an effective amount of a compound Formula I, or a pharmaceutically acceptable salt thereof; or a compound provided in Table 1, or a pharmaceutically acceptable salt thereof.

The present application further provides a method of inhibiting G3BP2, ZEB1, and G3BP1 in a cell, comprising contacting the cell with an effective amount of a compound Formula I, or a pharmaceutically acceptable salt thereof, or a compound provided in Table 1, or a pharmaceutically acceptable salt thereof.

The present application further provides a method of inhibiting SART3 in a cell, comprising contacting the cell with an effective amount of a compound Formula I, or a pharmaceutically acceptable salt thereof, or a compound provided in Table 1, or a pharmaceutically acceptable salt thereof.

The present application further provides a method of inhibiting NANOG in a cell, comprising contacting the cell with an effective amount of a compound Formula I, or a pharmaceutically acceptable salt thereof, or a compound provided in Table 1, or a pharmaceutically acceptable salt thereof.

The present application further provides a method of inhibiting OCT4 in a cell, comprising contacting the cell with an effective amount of a compound Formula I, or a pharmaceutically acceptable salt thereof, or a compound provided in Table 1, or a pharmaceutically acceptable salt thereof.

The present application further provides a method of inhibiting G3BP2, ZEB1, G3BP1, SART3, NANOG, OCT4, or any combination thereof, in a cell, comprising contacting the cell with an effective amount of a compound Formula I, or a pharmaceutically acceptable salt thereof, or a compound provided in Table 1, or a pharmaceutically acceptable salt thereof.

The present application further provides a method of inhibiting PD-L1 in a cell, comprising contacting the cell with an effective amount of a compound Formula I, or a pharmaceutically acceptable salt thereof, or a compound provided in Table 1, or a pharmaceutically acceptable salt thereof.

The present application further provides a method of inhibiting growth of a cancer stem cell, comprising contacting the cancer stem cell with an effective amount of a compound of Formula I, or a pharmaceutically acceptable salt thereof, or a compound provided in Table 1, or a pharmaceutically acceptable salt thereof. In some embodiments, the method comprises inhibiting growth of a cancer stem cell in a patient in need thereof.

In some embodiments, the cancer stem cell is selected from the group consisting of a breast cancer stem cell, a cancer of the head and neck stem cell, a thyroid cancer stem cell, and a colorectal cancer stem cell. In some embodiments, the cancer stem cell is a breast cancer stem cell. In some embodiments, the cancer stem cell is associated with overexpression of G3BP2. In some embodiments, the cancer stem cell is associated with overexpression of ZEB1. In some embodiments, the cancer stem cell is associated with overexpression of G3BP1. In some embodiments, the cancer stem cell is associated with overexpression of SART3. In some embodiments, the cancer stem cell is associated with overexpression of NANOG. In some embodiments, the cancer stem cell is associated with overexpression of OCT4. In some embodiments, the cancer stem cell is associated with overexpression of G3BP2 and overexpression of ZEB1. In some embodiments, the cancer stem cell is associated with overexpression of G3BP2, overexpression of ZEB1, and overexpression of G3BP1. In some embodiments, the cancer stem cell is associated with overexpression of G3BP2 and overexpression of ZEB1, overexpression of G3BP1, overexpression of SART3, overexpression of NANOG, overexpression of OCT4, or any combination thereof. In some embodiments, the cancer stem cell is resistant to treatment with an additional therapeutic agent or a radiation therapy. In some embodiments, the additional therapeutic agent is a chemotherapeutic agent. In some embodiments, the cancer stem cell is resistant to treatment with a chemotherapeutic agent and a radiation therapy.

The present application further provides a method of treating inflammation, comprising administering to a patient in need thereof a therapeutically effective amount of a compound of Formula I, or a pharmaceutically acceptable salt thereof, or a compound provided in Table 1, or a pharmaceutically acceptable salt thereof. In some embodiments, the inflammation is selected from the group consisting of inflammation of the eye, inflammation of the skin, inflammation of an organ (e.g., brain, liver, pancreas, heart, lung, stomach, spleen, and the like), inflammation of the respiratory tract, inflammation of the digestive tract, muscular inflammation, inflammation of the lymphatic system, and the like. In some embodiments, the inflammation is associated with a cancer. In some embodiments, the inflammation is associated a cancer selected from the group consisting of breast cancer, cancer of the head and neck, thyroid cancer, and colorectal cancer. In some embodiments, the inflammation is associated with breast cancer. In some embodiments, the inflammation is associated with one or more NF-κB target genes, for example, one or more NF-κB target genes provided in Pahl, *Oncogene*, 1999, 18(49), 6853-6866. In some embodiments, the inflammation is associated with a gene selected from the group consisting of IL1a, IL6, IL6, and TNFα

Assay Methods

The present application further provides a method of identifying an inhibitor of a cancer stem cell. In some embodiments, the method comprises:
  i) contacting a cancer stem cell with a test compound and a non-lethal dose of a chemotherapeutic agent; and
  ii) measuring the viability of the cancer stem cell;
  wherein the test compound is identified as an inhibitor of a cancer stem cell if the viability of the cancer stem cell is reduced by at least 90% after contacting with the test compound and the chemotherapeutic agent compared to the viability of the cancer stem cell prior to contacting with the test compound and the chemotherapeutic agent.

In some embodiments, the method further comprises:
  i) contacting a non-cancerous cell with a test compound; and
  ii) measuring the viability of the non-cancerous cell.

In some embodiments, the method comprises:
  i) contacting a cancer stem cell with a test compound and a non-lethal dose of a chemotherapeutic agent;
  ii) contacting a non-cancerous cell with a test compound; and
  iii) measuring the viability of the cancer stem cell and the viability of the non-cancerous cell;
  wherein the test compound is identified as an inhibitor of a cancer stem cell if the viability of the cancer stem cell is reduced by at least 90% after contacting with the test compound and the chemotherapeutic agent compared to the viability of the cancer stem cell prior to contacting with the test compound and the chemotherapeutic agent.

In some embodiments, the chemotherapeutic agent is selected from the group consisting of a taxane, doxorubicin, and cisplatin. In some embodiments, the chemotherapeutic agent is a taxane. In some embodiments, the taxane is paclitaxel.

In some embodiments, the viability of the cancer stem cell is measured using an MTT assay.

In some embodiments, the test compound is non-toxic to the non-cancerous cell (e.g., the non-cancerous cell survives the contacting with the test compound). In some embodiments, the test compound is non-toxic to the non-cancerous cell upon contacting the test compound with the non-cancerous cell from about 12 to about 72 hours. In some embodiments, the test compound is non-toxic to the non-cancerous cell upon contacting the test compound with the non-cancerous cell for about 24 hours. In some embodiments, the test compound is non-toxic to the non-cancerous cell upon contacting the test compound with the non-cancerous cell for about 48 hours.

In some embodiments, the viability of the non-cancerous cell is unaffected by the test compound. In some embodiments, the viability of the non-cancerous cell is substantially unaffected compared to the viability of the non-cancerous cell prior to contacting with the test compound. In some embodiments, the viability of the non-cancerous cell is unaffected compared to the viability of the non-cancerous cell prior to contacting with the test compound over a period of 24 hours. In some embodiments, the viability of the non-cancerous cell is substantially unaffected compared to the viability of the non-cancerous cell prior to contacting with the test compound over a period of 24 hours. In some embodiments, the viability of the non-cancerous cell is unaffected compared to the viability of the non-cancerous cell prior to contacting with the test compound over a period of 24 hours. In some embodiments, the viability of the non-cancerous cell is substantially unaffected compared to the viability of the non-cancerous cell prior to contacting with the test compound over a period of 48 hours. In some embodiments, the non-cancerous cell is a normal human umbilical vein endothelial cell (HUVEC).

As used herein, the term "substantially unaffected" refers to a non-cancerous cell having from about 80% to about 100% viability after contact with the test compound compared to the viability of the non-cancerous cell prior to contacting with the test compound. For example, a non-cancerous cell is substantially unaffected if, after contact with the test compound, the cell viability is about 80% to about 100%, about 80% to about 99%, about 80% to about 98%, about 80% to about 97%, about 80% to about 96%, about 80% to about 95%, about 80% to about 90%, about 80% to about 85%, about 85% to about 100%, about 85% to about 99%, about 85% to about 98%, about 85% to about 97%, about 85% to about 96%, about 85% to about 95%, about 85% to about 90%, about 85% to about 85%, about 90% to about 100%, about 90% to about 99%, about 90% to about 98%, about 90% to about 97%, about 90% to about 96%, about 90% to about 95%, about 95% to about 100%, about 95% to about 99%, about 95% to about 98%, about 95% to about 97%, about 95% to about 96%, about 96% to about 100%, about 96% to about 99%, about 96% to about 98%, about 96% to about 97%, about 97% to about 100%, about 97% to about 99%, about 97% to about 98%, about 98% to about 100%, about 98% to about 99%, or about 99% to about 100% viability compared to the viability of the non-cancerous cell prior to contacting with the test compound.

In some embodiments, the method of identifying an inhibitor of a cancer stem cell further comprises identifying an intracellular protein that binds to the test compound. In some embodiments, the method comprises:
  i) forming a conjugate of the test compound and a nanoparticle;
  ii) contacting the conjugate with the intracellular protein;
  iii) contacting the intracellular protein with a non-conjugated nanoparticle; and
  iv) analyzing the binding of the intracellular protein to the conjugate and the binding of the intracellular protein to the non-conjugated nanoparticle;
  wherein the intracellular protein is identified as bound to the test compound if the intracellular protein substantially binds to the conjugate and does not substantially bind to the non-conjugated nanoparticle.

In some embodiments, the nanoparticle comprises a metallic nanoparticle. In some embodiments, the nanoparticle comprises a carboxyl-substituted nanoparticle. In some embodiments, the nanoparticle comprises a magnetic carboxyl-substituted nanoparticle.

As used herein, the term "conjugate" refers to a test compound that has been adsorbed onto the surface of a nanoparticle, a test compound that has been chemically bonded (e.g., by formation of an ionic bond or a covalent bond) to the nanoparticle, or a combination thereof. In some embodiments, the conjugate is formed by preparing a mixture of the test compound and nanoparticle, followed by immunoprecipitation of the conjugate.

In some embodiments, the analyzing comprises separating a bound intracellular protein from an unbound intracellular protein using electrophoresis. In some embodiments, the analyzing further comprises analyzing the bound intracellular protein by mass spectrometry.

In some embodiments, the cancer stem cell is associated with overexpression of G3BP2. In some embodiments, the cancer stem cell is associated with overexpression of ZEB1. In some embodiments, the cancer stem cell is associated with overexpression of G3BP1. In some embodiments, the cancer stem cell is associated overexpression of G3BP2 and overexpression of ZEB1. In some embodiments, the cancer stem cell is associated overexpression of G3BP2, overexpression of ZEB1, and overexpression of G3BP1. In some embodiments, the cancer stem cell is associated with overexpression of G3BP2 and overexpression of ZEB1, overexpression of G3BP1, overexpression of SART3, overexpression of NANOG, overexpression of OCT4, or any combination thereof. In some embodiments, the cancer stem cell is associated with overexpression of PD-L1.

In some embodiments, the cancer stem cell is selected from the group consisting of a breast cancer stem cell, a glioblastoma cancer stem cell, a cancer of the head and neck stem cell, a thyroid cancer stem cell, and a colorectal cancer stem cell. In some embodiments, the cancer stem cell is selected from the group consisting of a breast cancer stem cell, a cancer of the head and neck stem cell, a thyroid cancer stem cell, and a colorectal cancer stem cell. In some embodiments, the cancer stem cell is a breast cancer stem cell. In some embodiments, the cancer stem cell is a glioblastoma stem cell. In some embodiments, the cancer stem cell is a breast cancer stem cell or a glioblastoma stem cell. In some embodiments, the cancer stem cell is resistant to treatment with an additional therapeutic agent or a radiation therapy. In some embodiments, the additional therapeutic agent is a chemotherapeutic agent. In some embodiments, the cancer stem cell is resistant to treatment with a chemotherapeutic agent and a radiation therapy.

Combination Therapies

In some embodiments, the methods provided herein further comprise administering an additional therapeutic agent or a radiation therapy. Example therapeutic agents include, but are not limited to, steroids, anesthetics (e.g. for use in combination with a surgical procedure), immunosuppressants, anti-inflammatory agents, and chemotherapeutic agents. In some embodiments, a compound provided herein (i.e., a compound of Formula I, or a pharmaceutically acceptable salt thereof; or a compound provided in Table 1, or a pharmaceutically acceptable salt thereof) is administered in combination with an additional therapeutic agent or a radiation therapy during a surgical procedure.

In some embodiments, the additional therapeutic agent is administered simultaneously with a compound provided herein. In some embodiments, the additional therapeutic agent is administered after administration of a compound provided herein. In some embodiments, the additional therapeutic agent is administered prior to administration of a compound provided herein.

In some embodiments, the additional therapeutic agent is selected from the group consisting of a steroid, an anesthetic, an immunosuppressant, an anti-inflammatory agent, and a chemotherapeutic agent.

Example steroids include, but are not limited to, corticosteroids such as cortisone, dexamethasone, hydrocortisone, methylprednisolone, prednisolone, and prednisone.

Example anesthetics include, but are not limited to local anesthetics such as lidocaine, procain, and ropivacaine.

Example immunosuppressants include, but are not limited to, azathioprine, chlorambucil, cyclophosphamide, cyclosporine, daclizumab, infliximab, methotrexate, and tacrolimus.

Example anti-inflammatory agents include, but are not limited to, aspirin, choline salicylates, celecoxib, diclofenac potassium, diclofenac sodium, diclofenac sodium with misoprostol, diflunisal, etodolac, fenoprofen, flurbiprofen, ibuprofen, ketoprofen, meclofenamate sodium, mefenamic acid, nabumetone, naproxen, naproxen sodium, oxaprozin, piroxican, rofecoxib, salsalate, sodium salicylate, sulindac, tolmetin sodium, and valdecoxib.

Example chemotherapeutics include, but are not limited to, taxanes (e.g., docetaxel, paclitaxel), platinum agents (e.g., cisplatin, carboplatin), anti-mitotic agents (e.g., vinorelbine), capecitabine, doxorubicin, gemcitabine, mitoxantrone, ixabepilone, eribulin, and the like.

In some embodiments, the methods provided herein further comprise administration of a compound selected from the group consisting of cisplatin, etoposide, irinotecan, topotecan, paclitaxel, docetaxel, tamoxifen, 5-fluorouracil, methotrexate, temozolomide, cyclophosphamide, gefitinib, erlotinib hydrochloride, imatinib mesylate, cytarabine, gemcitabine, uracil mustard, chlormethine, ifosfamide, chlorambucil, pipobroman, triethylenemelamine, busulfan, carmustine, lomustine, streptozocin, dacarbazine, floxuridine, 6-mercaptopurine, 6-thioguanine, fludarabine phosphate, oxaliplatin, pentostatin, vinblastine, vincristine, vindesine, bleomycin, dactinomycin, daunorubicin, epirubicin, idarubicin, deoxycoformycin, mitomycin-C, L-asparaginase, teniposide, testolactone, estramustine, carboplatin, hydroxyurea, amsacrine, procarbazine, mitotane, mitoxantrone, vinorelbine, anastrazole, letrozole, capecitabine, raloxifene, xeloda, vinorelbine, cetuximab, N,N'N'-triethylenethiophosphoramide, altretamine, trastuzumab, fulvestrant, and exemestane.

In the field of medical oncology it is normal practice to use a combination of different forms of treatment to treat each patient with cancer. In medical oncology the other component(s) of such conjoint treatment or therapy in addition to compositions provided herein may be, for example, surgery, radiotherapy, and chemotherapeutic agents, such as kinase inhibitors, signal transduction inhibitors and/or monoclonal antibodies. Compounds provided herein therefore may also be useful as adjuvants to cancer treatment, that is, they can be used in combination with one or more additional therapies or therapeutic agents, for example a chemotherapeutic agent that works by the same or by a different mechanism of action.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.
General Methods A mammosphere assay was performed with MammoCult™ Medium. An extreme limiting dilution assay was performed by implanting cells in the mammary fat pad of NOD-SCID mice. Flowcytometry for CD44$^+$/CD24$^-$ or ALDEFLUOR$^+$ populations was performed to determine changes in these populations after silencing G3BP2. Chromatin immunoprecipitation was used followed by ChIP-qPCR to examine the chromatin state at the ZEB1 promoter in cells with different expression levels of G3BP2.

Immunoprecipitation was performed using Protein A Sepharose beads (GE Healthcare Lifesciences). Beads were washed, conjugated to the immunoprecipitating antibody for 2 hours, and immunoprecipitated overnight at 4° C. Western blots were performed using a standard protocol; using 4-10% gradient gel and Tris-glycine transfer buffer.

For immunofluorescence microscopy procedures, cells were fixed with 4% formaldehyde, washed with ice-cold PBS, blocked with 5% normal horse serum in PBS and stained with primary antibody (anti-CD24 (1:50 dilution), or anti-ING4 (1:100)), and washed and stained with secondary antibodies for confocal microscopy (1:1,000) (Jackson Immunoresearch). Cells were mounted with 4'-6-diamidino-2-phenylindole-containing mounting media (Vectashield) for confocal microscopy and imaged using an Olympus Fluoview FV 1000 confocal microscope.

Flowcytometry was used for detection of ALDEFLUOR$^+$ and CD44$^+$/CD24$^-$ populations. The ALDEFLUOR assay (Stemcell Technologies) was performed according to manufacturers protocol.

Anti-G3BP2 (abcam), anti-Tri-Methyl-histon H3 (Lys4) (Cell Signaling), anti-CD24 (Santa Cruz Biotechnology), anti-ING4 (LSBio); anti-ZEB1 (Novus biological), antiβ-actin and anti-α-Tubulin (Sigma Life Science) antibodies were used for the Examples provided herein.

The following shRNAs for G3BP2 were used in the Examples provided herein:

sh1,
(SEQ ID NO: 8)
CGGGAGTTTGTGAGGCAATAT;

sh2:
(SEQ ID NO: 9)
GACTCTGACAACCGTAGAATA cloned in pLKO_TRC005 lentiviral vector. The same vector was used for ING4 shRNA with (SEQ ID NO: 10)
CCGGGAACCCACCTATTGCCT cDNA was cloned in a retroviral pBABE vector.

All animal procedures were performed following the guidelines of Public Health Service Policy on Humane Care of Laboratory Animals and approved by the Institutional Animal Care and Use Committee. Mice were bred and housed in the Edwin L. Steele Laboratory Animal Core (Massachusetts General Hospital).

Example 1. Chemical Approach for Dissection of the Tumor Plasticity Program

Compounds that targeted modified MDA-MB-231 cells in combination with paclitaxel (0.2 µM for 48 hours) were used. 60,000 initial compounds were screened and 256 compounds were selected for the second screening step. To eliminate toxic compounds, non-malignant cells were treated with the test compounds, and 117 non-toxic compounds were selected for further analysis. Cell viability assays (MTT) of modified MDA-MB-231 cancer cells with five different concentrations (0.12 mol/L, 0.37 mol/L, 1.11 mol/L, 3.33 mol/L and 10 mol/L) was then performed, as discussed in the following examples.

Example 2. Protein Binding Assay

Figure 5:
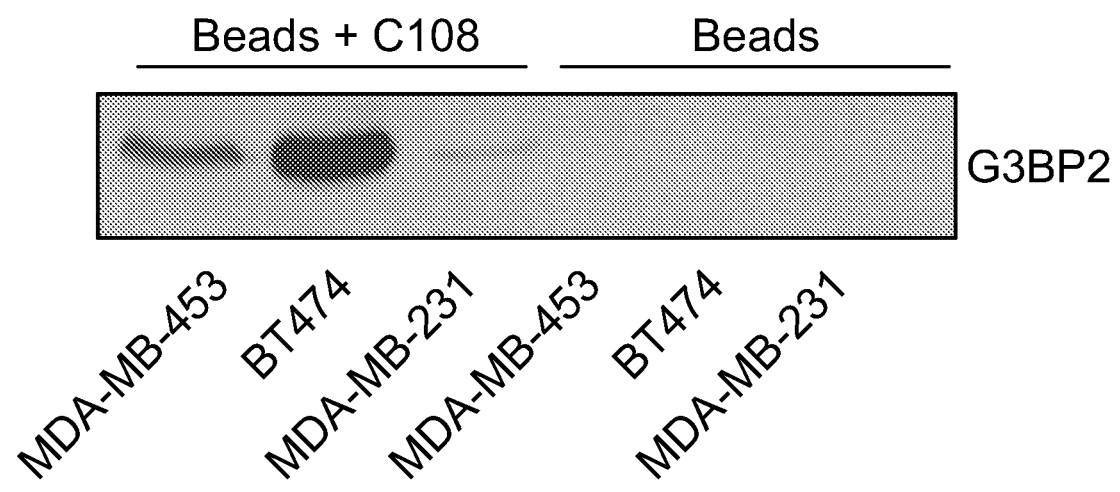
FIG. 5 shows a representative Western blot analysis of protein lysates from three breast cancer cell lines incubated overnight with 2-hydroxy-N'-[1-(2-hydroxyphenyl)ethylidene]benzohydrazide (i.e., C108) conjugated TURBO-BEADS® and non-conjugated TURBOBEADS® beads. Western blot analysis was performed with G3BP2 antibodies. Small molecule 2-hydroxy-N'-[1-(2-hydroxyphenyl)ethylidene]benzohydrazide was conjugated to TURBO-BEADS® carboxy nanoparticles (TURBOBEADS®). TURBOBEADS® alone were used as a negative control.

To determine which genes would bind to a test compound, TURBOBEADS® carboxy nanoparticles (TURBOBEADS®) were conjugated to 2-hydroxy-N'-[1-(2-hydroxyphenyl)ethylidene]benzohydrazide for 20 mi as per manufacturer's protocol, followed by overnight immunoprecipitation at 4° C. Proteins from metastatic cancer cells were pulled-down with using the test compound-nanoparticle conjugates and using unconjugated nanoparticles as a control. Purified proteins were separated on an 8% agarose gel, as shown in FIG. 5, and bands that were bound to the test compound but not control were cut out from the gel and analyzed by mass spectrometry Mass spectrometry analysis revealed 42 proteins that bind to the test compound, which are shown in Table 2.

TABLE 2

Proteins from Pull Down Experiment with 2-hydroxy-N'-[1-(2-hydroxyphenyl)ethylidene]benzohydrazide

| # | Protein |
|---|---------|
| 1 | SNW1 SNW domain-containing protein 1 |
| 2 | USP22 ubiquitin specific peptidase 3-like |
| 3 | CSNK2A1 protein |
| 4 | IGF2BP1 Insulin-like growth factor 2 mRNA-binding protein 1 |

TABLE 2-continued

Proteins from Pull Down Experiment with 2-hydroxy-N'-[1-(2-hydroxyphenyl)ethylidene]benzohydrazide

| # | Protein |
|---|---------|
| 5 | PPP2R1B Isoform 1 of Serine/threonine-protein phosphatase 2A 65 kDa regulatory subunit A beta isoforms |
| 6 | PTPN9 protein tyrosine phosphatase, non-receptor type 9 |
| 7 | CRKL Crk-like protein |
| 8 | TBRG4 cDNA FLJ56153 |
| 9 | GNL3 Isoform 2 of Guanine nucleotide-binding protein-like 3 |
| 10 | PLK1 Serine/threonine-protein kinase PLK1 |
| 11 | SHOC2 Leucine-rich repeat protein SHOC-2 |
| 12 | CDKN2AIP CDKN2A interacting protein |
| 13 | METAP2 Methionine aminopeptidase 2 |
| 14 | MTDH Protein LYRIC |
| 15 | ARCN1 Coatomer subunit delta variant 2 |
| 16 | GRK6 Isoform GRK6A of G protein-coupled receptor kinase 6 |
| 17 | UCHL5 Isoform 2 of Ubiquitin carboxyl-terminal hydrolase isozyme L5 |
| 18 | IKIP Isoform 1 of Inhibitor of nuclear factor kappa-B kinase-interacting protein |
| 19 | HDGF Hepatoma-derived growth factor |
| 20 | OSGEP Probable O-sialoglycoprotein endopeptidase |
| 21 | MAP2K6 Isoform 1 of Dual specificity mitogen-activated protein kinase kinase 6 |
| 22 | NACC1 Nucleus accumbens-associated protein 1 |
| 23 | MAPK1 Mitogen-activated protein kinase 1 |
| 24 | RANGAP1 Ran GTPase-activating protein 1 |
| 25 | G3BP2 Ras GTPase-activating protein-binding protein 2 |
| 26 | G3BP1 Ras GTPase-activating protein-binding protein 1 |
| 27 | PPP1Ca |
| 28 | MAP3K7IP1 Mitogen-activated protein kinase kinase kinase 7-interacting protein 1 |
| 29 | PIP5K1A |
| 30 | PPP2R1A |
| 31 | API5 Isoform 2 of Apoptosis inhibitor 5 |
| 32 | MPP7 MAGUK p55 subfamily member 7 kinase |
| 33 | ORC2L Origin recognition complex subunit 2 |
| 34 | RIC8A resistance to inhibitors of cholinesterase 8 homolog A |
| 35 | RBBP5 cDNA FLJ59722, highly similar to Retinoblastoma-binding protein 5 |
| 36 | GTF3C5 Isoform 2 of General transcription factor 3C polypeptide 5 |
| 37 | SNRNP40 cDNA FLJ56825, highly similar to WD repeat protein 57 |
| 38 | ARMCX3 Armadillo repeat-containing X-linked protein 3 |
| 39 | THOC6 Isoform 3 of THO complex subunit 6 homolog |
| 40 | PIH1D1 PIH1 domain-containing protein 1 |
| 41 | UFD1L Isoform Short of Ubiquitin fusion degradation protein 1 homolog |
| 42 | PSTPIP2 Isoform 1 of Proline-serine-threonine phosphatase-interacting protein 2 |
| 43 | IGF2BP2 Insulin-like growth factor 2 mRNA-binding protein 2 |
| 44 | RGS19 gene |

Example 3. MTT Assay shRNA-expressing lentivirus was obtained for each pull-down protein and used to infect modified MDA-MB-231 cells. MTT assays were performed with shRNA stable cell lines and treated with non-lethal doses of paclitaxel. Only shRNA G3BP12 made cells sensitive to treatment with paclitaxel. To confirm that the test compound (2-hydroxy-N'-[1-(2-hydroxyphenyl)ethylidene]benzohydrazide) bound to G3B3P2, an immunoprecipitation with magnetic nanoparticles bound to 2-hydroxy-N'-[1-(2-hydroxyphenyl)ethylidene]benzohydrazide and nanoparticles alone (control) was carried out. Western blotting revealed that G3BP2 binds to 2-hydroxy-N'-[1-(2-hydroxyphenyl)ethylidene]benzohydrazide.

Example 4. Mammosphere Assay

For the mammosphere assay, MammoCult™ Medium (Human) For Culture of Mammospheres (Stemcell Technologies) was used. Cells were seeded at a density of 1000 cells per well in ultralow attachment 6-well plates containing MammoCult media supplemented with 10% (v/v) Mammocult proliferation supplement, 4 µg/mL % heparin and 0.48 µg/mL hydrocortisone. This assay was performed according to manufacturer's instructions.

Figure 1B:
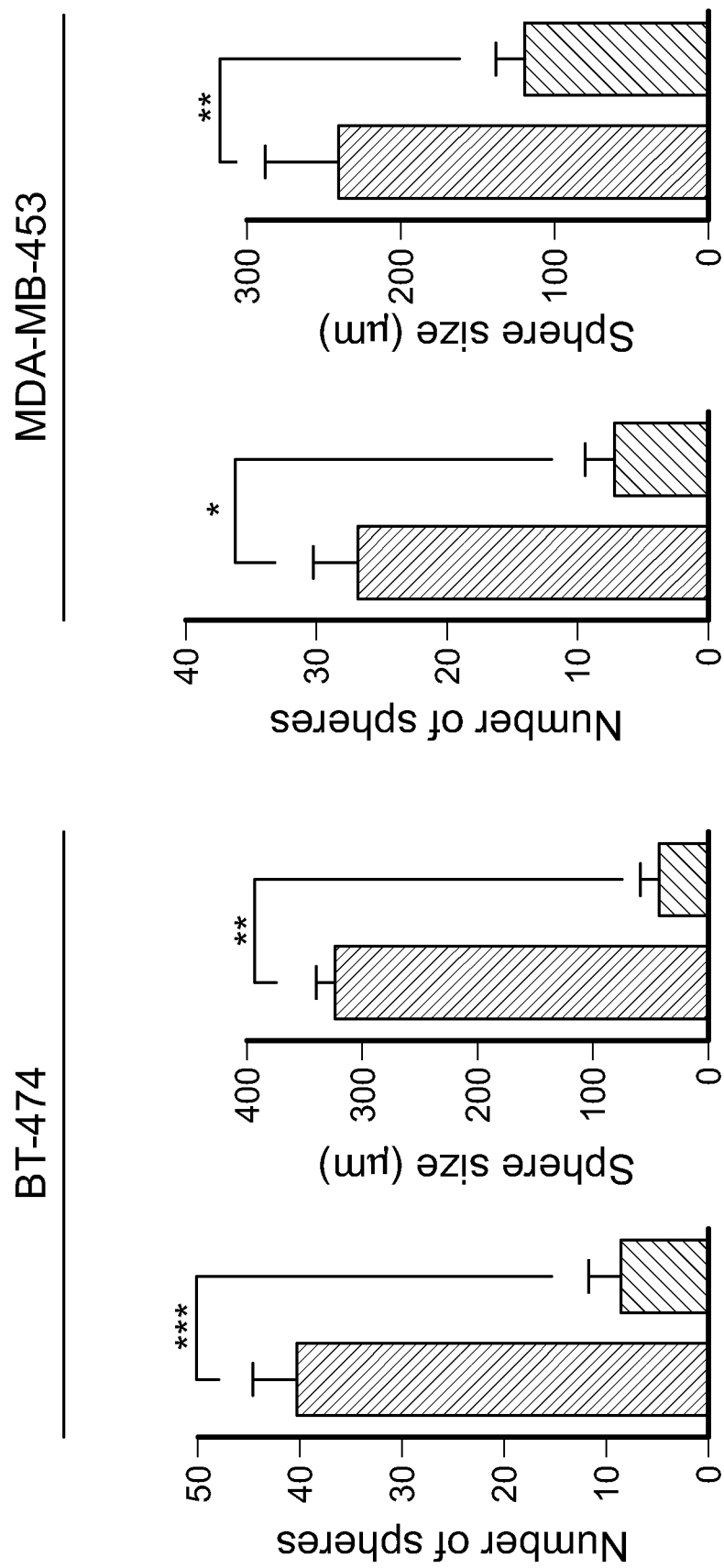
FIG. 1B shows the tumorigenic efficiency of control cancer stem cells (left bars) and cancer stem cells with G3BP2 knock down (right bars). The data was determined based on number of spheres that emerge from single cells. (error bars represent SEM; t test n=3, *P<0.05, P<0.005, *P<0.0005).

G3BP2 diminution by shRNA in the breast cancer cell lines BT-474 and MDA-MB-453 was functionally significant, resulting in drastically decreased mammosphere numbers; the spheres that did form were smaller as well, as shown in FIG. 1A-1B). The data indicate that suppression of G3BP2 hinders mammosphere formation.

Example 5. Extreme Limiting Dilution Assay

A dilution range of 50, 500 and 5000 (BT-474) or 1,000; 10,000 and 100,000 (MDA-MB-453) tumor cells were implanted into the left third mammary fat pad of female NOD-SCID mice aged 6-8 weeks. Tumor outgrowth was evaluated 12 weeks after implantation. The web-based tool ELDA, available on the Walter and Eliza Hall Institute of Medical Research web site, was used for statistical analysis.

Figure 1C:
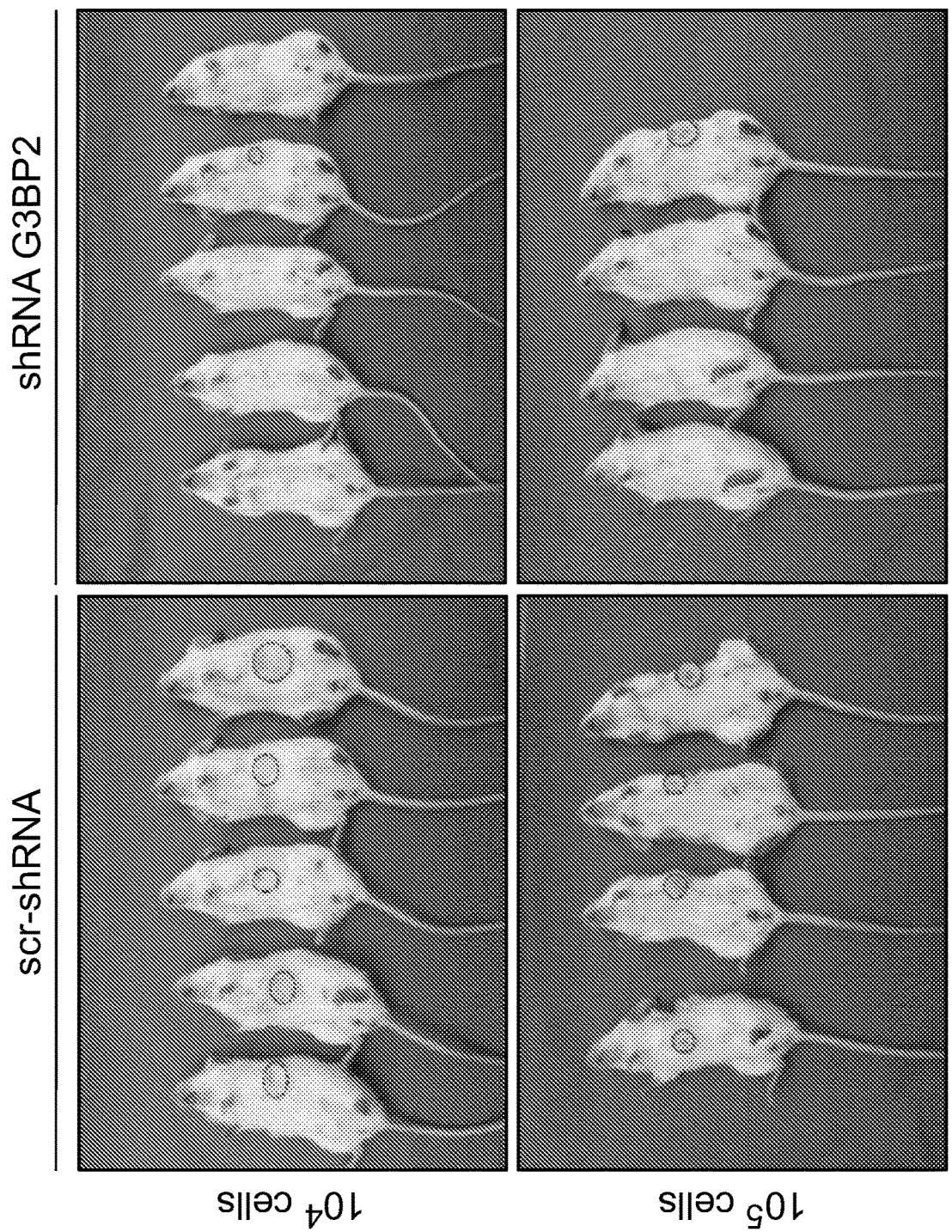
FIG. 1C shows results of an extreme limiting dilution assay (ELDA) for tumor-forming frequency of G3BP2 shRNA MDA-MB-453 cells and scr-control shRNA MDA-MB-453 cells in NOD-SCID mice.
Figure 6:
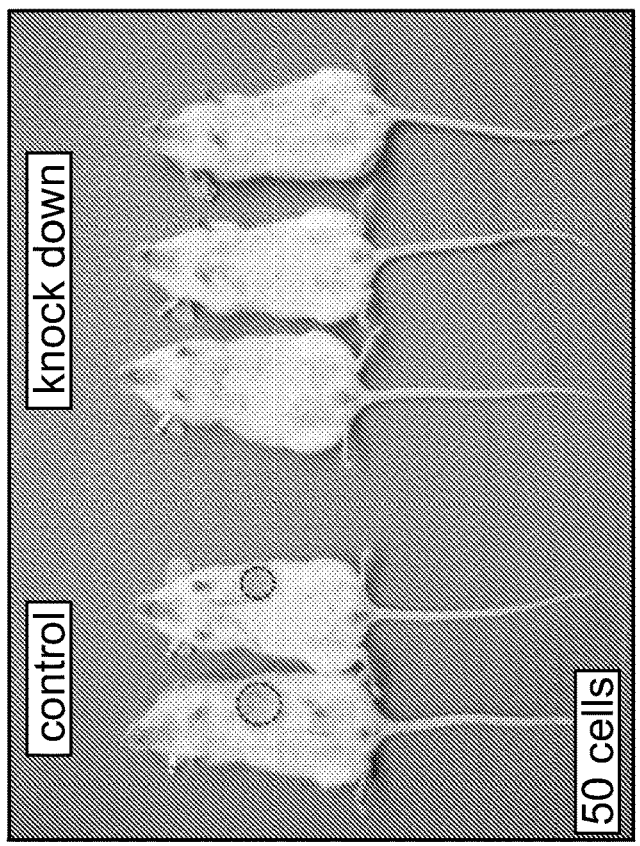
FIG. 6 shows a representative extreme limiting dilution assay performed with G3BP2 shRNA and scr-control shRNA BT474 cells in NOD-SCID mice. 50 and 500 cells were implanted in the mammary fat pad and were allowed to grow out to tumors for 90 days. The group having 50 cells implanted shows 0/3 in the G3BP2 repressed group a tumor outgrowth of 2/2 in the control group. In the group having 500 cells implanted, 3/7 in the G3BP2 knock down group compared to 6/6 control mice developed tumors.
Figure 6:
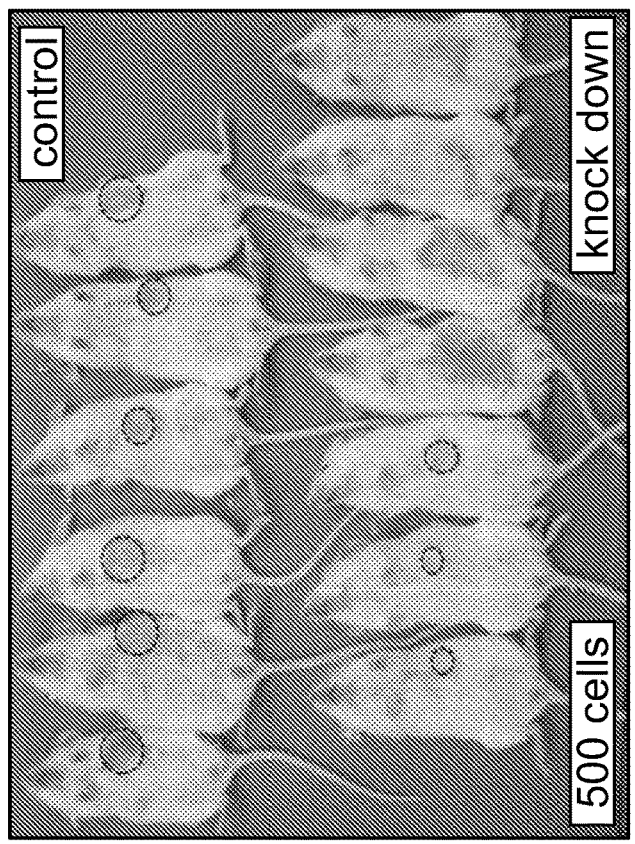

The pronounced effect of G3BP2 knockdown on self-renewal was preserved in vivo, as evidenced by the fact that MDA-MB-453 (see e.g. FIG. 1C) and BT-474 (see e.g. FIG. 6) cells with lower G3BP2 levels required substantially higher cell numbers to be injected into the mammary fat pad of NOD/SCID mice, while control cells were capable of forming tumors, as shown in Table 3. The data shown in FIG. 3C indicates that silencing G3BP2 in cancer cells changes the ability of the cells to form de novo tumors and changes their self-renewal capability.

TABLE 3

Tumor-initiating frequency of stable control and G3BP2 silenced cell lines BT-474 and MDA-MB-453 in NOD/SCID mice

| Cells | Cell Dose | | | | | | Tumour-Initiating Frequency | p Value |
|---|---|---|---|---|---|---|---|---|
| | $10^5$ | $10^4$ | $10^3$ | 5000 | 500 | 50 | (95% Interval) | |
| BT-474 scr-shRNA | | | | 5/6 | 6/6 | 2/2 | 1/794 (1/269-1/2,344) | |
| BT-474 shRNA G3BP2 | | | | 4/7 | 3/7 | 0/3 | 1/2,719 (1/1,197-1/6,177) | 0.0177 |
| MDA-MB-453 scr-shRNA | 4/4 | 5/5 | 0/7 | | | | 1/4,769 (1/1,873-1/12,142) | |
| MDA-MB-453 shRNA G3BP2 | 1/4 | 1/5 | 0/7 | | | | 1/198,893 (1/46,671-1/847,608) | 6.01e−06 |

Together, these findings indicate that G3BP2 is essential for the maintenance of a sub-population of cells that possess CSC properties both in vitro and in vivo.

Example 6. ALDEFLUOR Assay

The ALDEFLUOR assay was applied to identify the ALDEFLUOR⁺ population exhibiting high aldehyde dehydrogenase (ALDH) enzymatic activity in BT474 cells with G3BP3 overexpression (pBaBe-G3BP2) and pBaBe as a control. A single-cell suspension was incubated with ALDE-FLUOR substrate with and without DEAB (the specific inhibitor of ALDH) to establish the baseline fluorescence of these cells and to define the ALDEFLUOR$^+$ region. In all experiments, cells were first gated on P1-negative cells (i.e., viable cells). Approximately 33% of the overexpressed G3BP2 cells were ALDEFLUOR$^+$, compared to 11% of the control cells. In MDA-MB-231 cells, the ALDEFLUOR$^+$ population changed from 0.2% to (pBabe) 1.4% (pBabe G3BP2).

Figure 2A:
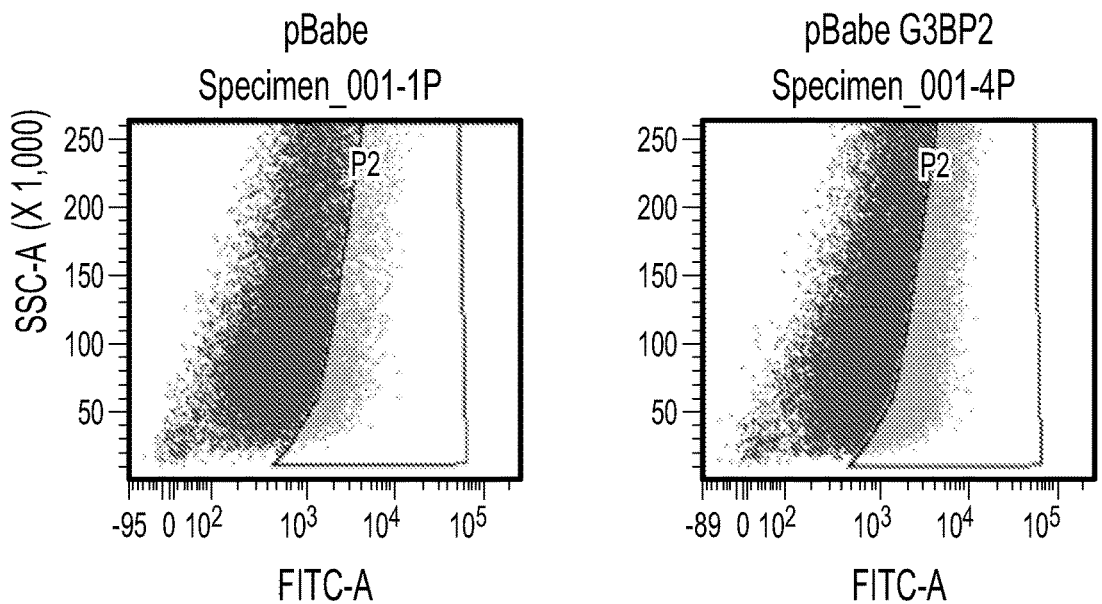
FIG. 2A shows that G3BP2 increases the Aldefluor positive population in breast cancer cells.
Figure 2B:
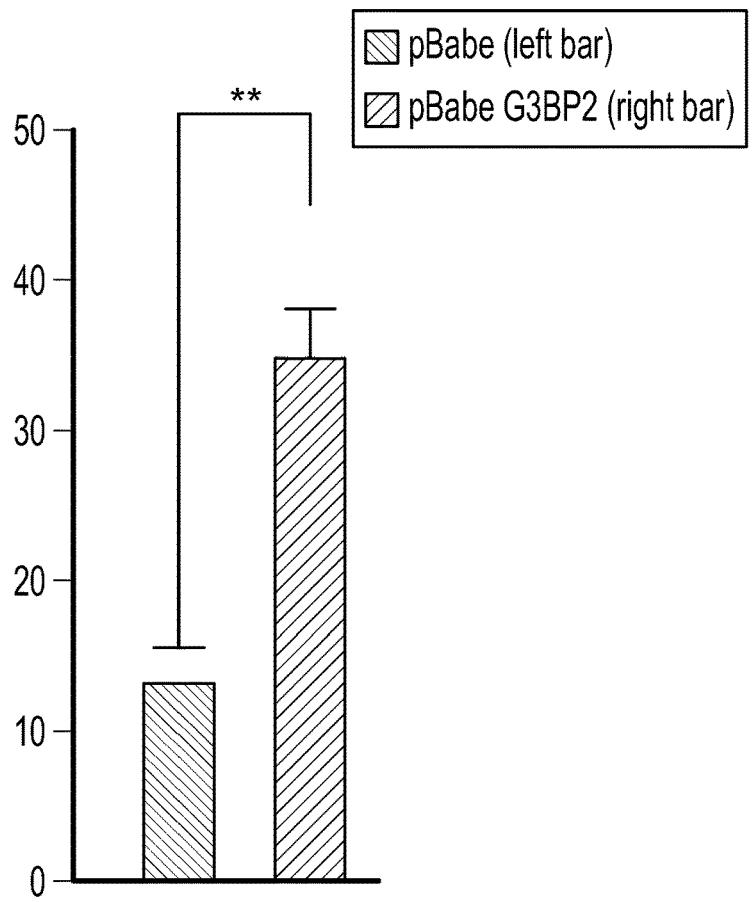
FIG. 2B shows relative fold change of ALDH$^+$ cells after G3BP2 overexpression (error bars represent SEM; t test n=3, *P<0.05). ALDH⁻ control (left bar) and ALDH⁺ cancer cells with G3BP2 overexpression (right bar).
Figure 2C:
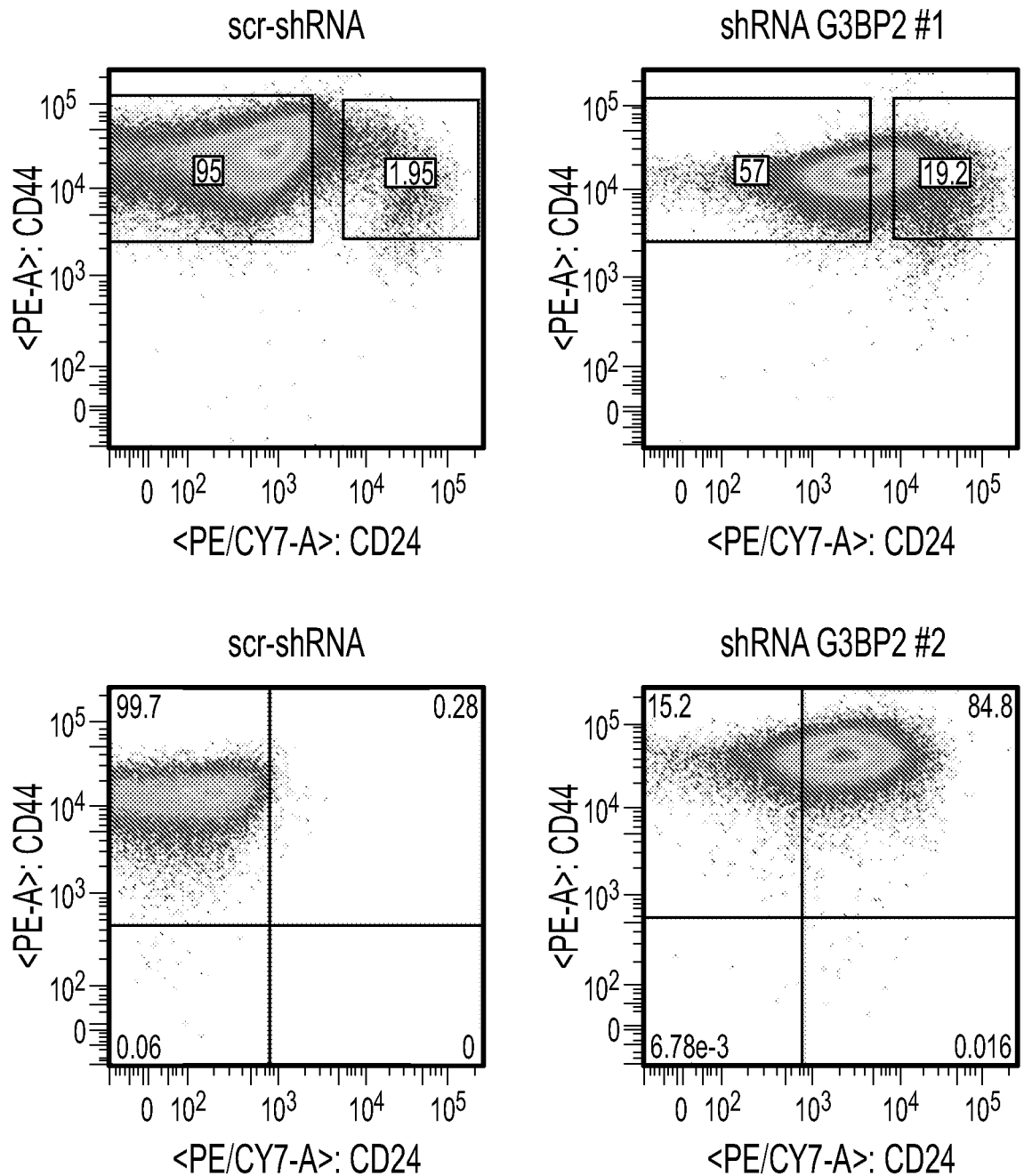
FIG. 2C shows knock down of G3BP2 increases protein level of CD24 in breast cancer cell lines. Expression of CD44 and CD24 in MDA-MB-231 control and G3BP2 knock down cells were analyzed by flowcytometry.

Since ALDH1$^+$ and/or CD44$^+$/CD24$^-$ have been reported as putative markers for CSC populations in breast cancer (see e.g., Al-Hajj et al., *Proceedings of the National Academy of Sciences of the United States of America*, 2003, 100, 3983-3988; Ginestier et al., *Cell Stem Cell*, 2007, 1, 555-567), it was next examined whether altering G3BP2 expression in MDA-MB-231 and BT-474 breast cancer cells affects the proportions of cells carrying the ALDH1$^+$ or CD44$^+$/CD24$^-$ marker profile. Flow cytometric analysis revealed that overexpression of G3BP2 in BT-474 cells resulted in an increase in ALDH1+ cells, as show n FIG. 2A-2B. In contrast, downregulation of G3BP2 expression enriched the CD24+ population in cell lines MDA-MB-231, as shown in FIG. 2C, suggesting that G3BP2 regulates the populations of non-CSC and CSC-like cells.

Example 7. Western Blot Analysis

Figure 2D:
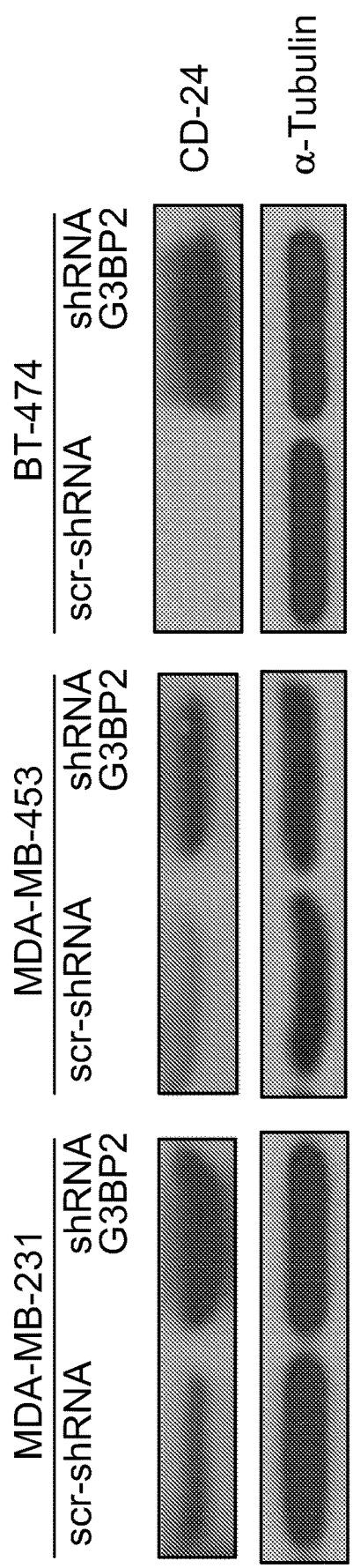
FIG. 2D shows a representative Western blot analysis of MDA-MB-231, MDA-MB-453 and BT-474 cell lysates, which shows that silencing G3BP2 results in an increased CD24 expression.
Figure 2E:
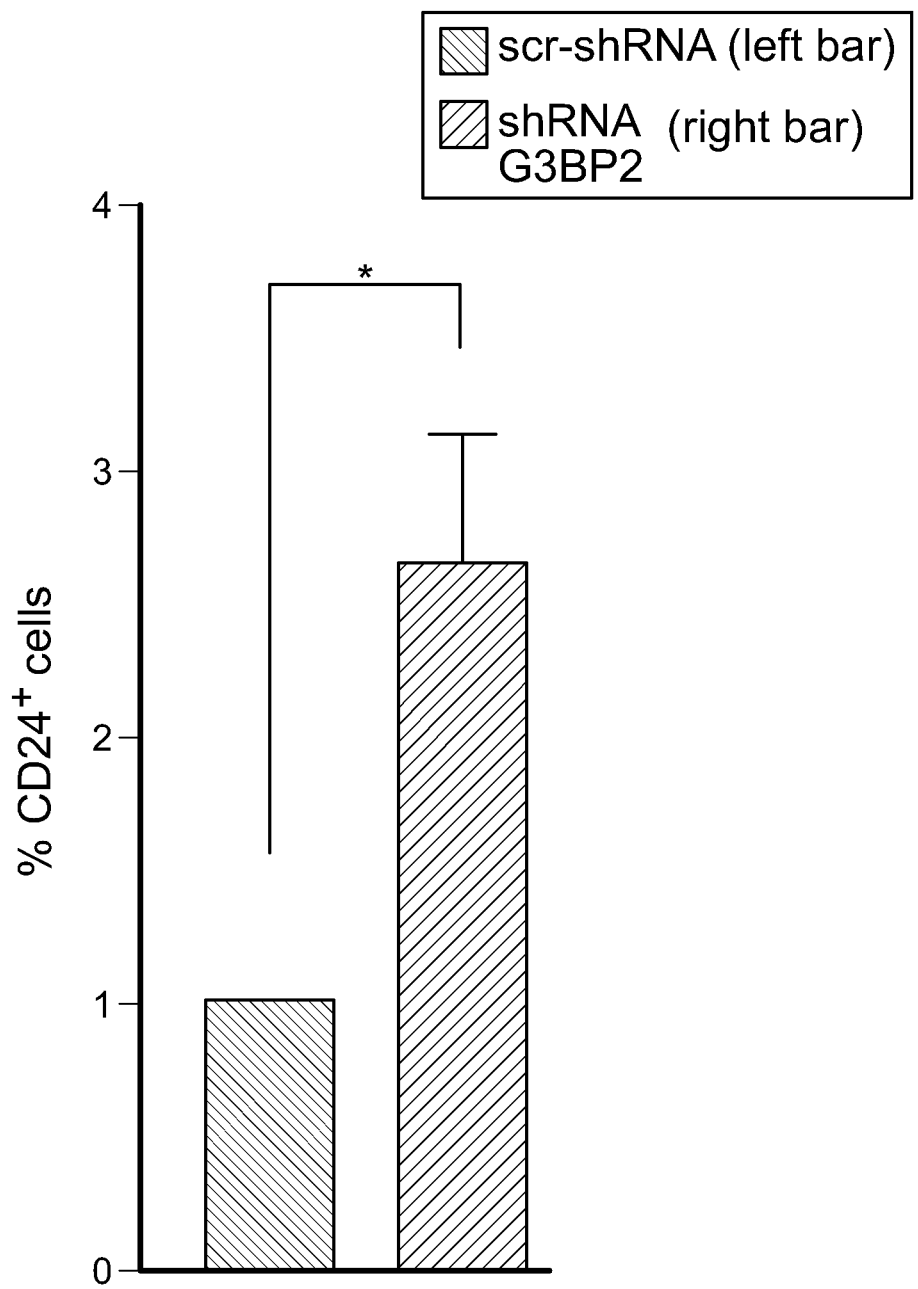
FIG. 2E shows quantitative analysis of CD24 immunofluorescence staining of scr-shRNA (left bar) and shRNA G3BP2 (right bar) MDA-MB-453 cells. Data is shown as percentage of CD24 positive cells/total cells (error bars represent SEM; t test n=3, *P<0.05).

To confirm that G3BP2 expression affects CD24+ populations, a Western blot analysis was performed with three breast cancer cell lines with or without G3BP2 silencing, as shown in FIG. 2D. These data confirmed that downregulation of G3BP2 leads to increased protein levels of CD24 in cells. To confirm that these alterations depend on G3BP2, immunofluorescence microscopy was used to assess the ratio of CD24+ cells in stable scr-shRNA and shRNA G3BP2 cell lines, as shown in FIG. 2E. In both instances, downregulation of G3BP2 resulted in a substantial increase of CD24 in cells, indicating enrichment for non-CSCs. Collectively, the results suggest that modulating G3BP2 expression in breast cancer cells affects the ratio of non-CSC and CSC-like populations.

Example 8. ZEB1 Knockdown

Figure 3B:
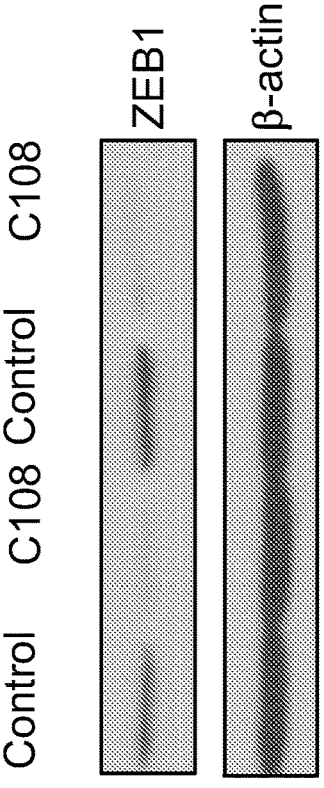
FIG. 3B shows ZEB1 protein levels evaluated via Western blot analysis with MDA-MB-453 and BT-474 cells that were treated with 2-hydroxy-N'-[1-(2-hydroxyphenyl)ethylidene]benzohydrazide for 24 h and lysed.
Figure 3D:
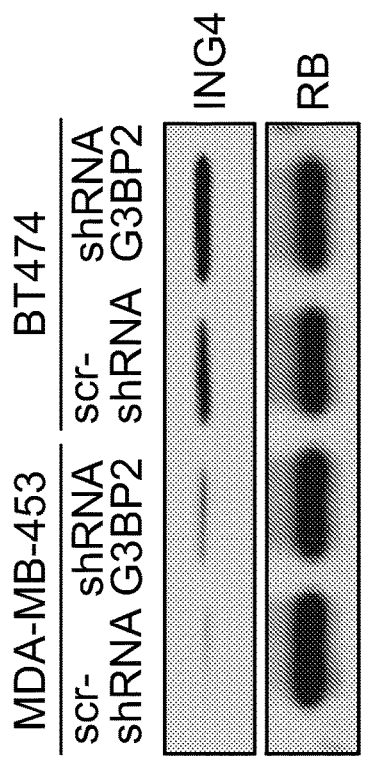
FIG. 3D shows a representative Western blot showing that nuclear fractions of ING4 are decreased by G3BP2. Rb protein was used as loading control for nuclear fraction.
Figure 3A:
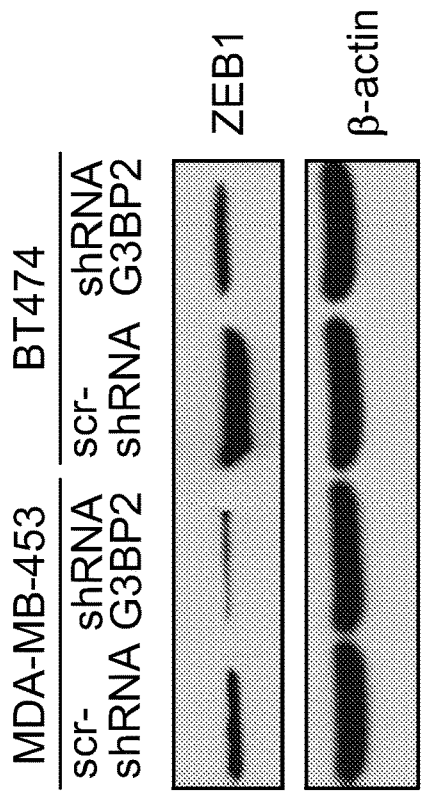
FIG. 3A shows a representative Western blot analysis for ZEB1 and proteins from the cell lysates isolated from MDA-MB-453 and BT-474 cells with scr-shRNA (control) or G3BP2 shRNA (Knock Down).

A direct molecular link between epithelial-mesenchymal transition (EMT) and CSC plasticity in breast cancer has recently been shown; EMT effectors such as ZEB1 can co-induce both EMT and stem-like properties (see e.g., Chaffer et al., Cell, 2013, 154, 61-74). To understand if the G3BP2-mediated CSC state intersects with the EMT program, we the protein level of ZEB1 in G3BP2 knockdown and overexpression breast cancer cell lines was analyzed. It was found that ZEB1 was decreased in MDA-MB-453 and BT-474 shG3BP2 cell lines, as shown in FIG. 3A. To confirm this data, the small molecule, 2-hydroxy-N'-[1-(2-hydroxyphenyl)ethylidene]benzohydrazide, that binds to protein G3BP2 was used. Treatment of these two breast cancer cell lines with 3 µM of 2-hydroxy-N'-[1-(2-hydroxyphenyl)ethylidene]benzohydrazide for 24 hours resulted in 5-7 fold ZEB1 inhibition, as shown in FIG. 3B. Together, the genetic and pharmacological data suggest that knockdown or inhibition of G3BP2 leads to reductions in ZEB1 expression.

Example 9. Regulation of ZEB1 Transcriptional Factor

Next, an examination was undertaken to determine how G3BP2, a predominantly cytoplasmic protein, can regulate the activity of the ZEB1 transcriptional factor. It has been shown, through protein pull-down and subsequent mass spectrometry analysis, that G3BP2 interacts with inhibitor of growth family, member 4 (ING4) (see e.g., Unoki et al., *The Journal of Biological Chemistry*, 2006, 281, 34677-34686). It has been hypothesized that G3BP2 regulates ZEB1 expression through the tumor suppressor ING4 (see e.g., Garkavtsev et al., *Nature*, 2004, 428, 328-332). PHD domains of ING4 are specifically (and highly robust) binding modules for the trimethylated lysine 4 of the histone H3 subunit (H3K4me3). H3K4me3 is associated with a chromatin state favoring transcriptional activity (see e.g., Bernstein et al., *Cell*, 2006, 125, 315-326). It was further hypothesized that accumulation of G3BP2 may sequester ING4 in the cytoplasm and consequently decrease the nuclear fraction of ING4 protein if the two proteins interact in the cytoplasm, and the resulting reduction in ING4 binding to H3K4me3 in the promoter region of ZEB1 may thereby increase production of this transcription factor.

Figure 3C:
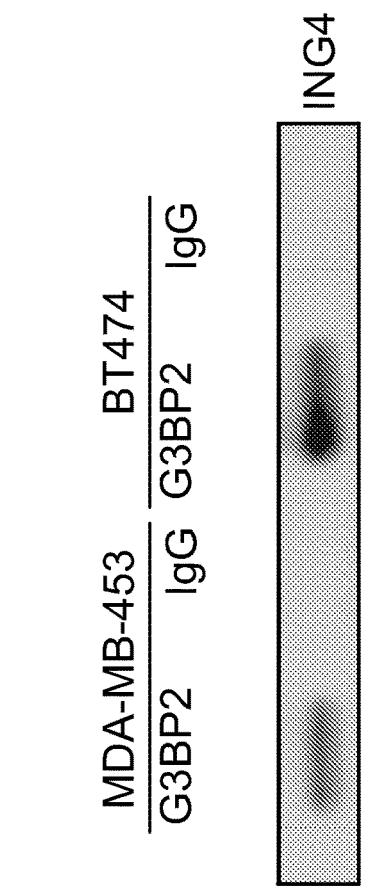
FIG. 3C shows cell extracts from two breast cancer cell lines that were immunoprecipitated with G3BP2 and IgG antibodies as a control, analyzed by Western blotting and probed for ING4, showing that G3BP2 physically interacts with ING4 and decreases nuclear fraction of ING4.
Figure 3E:
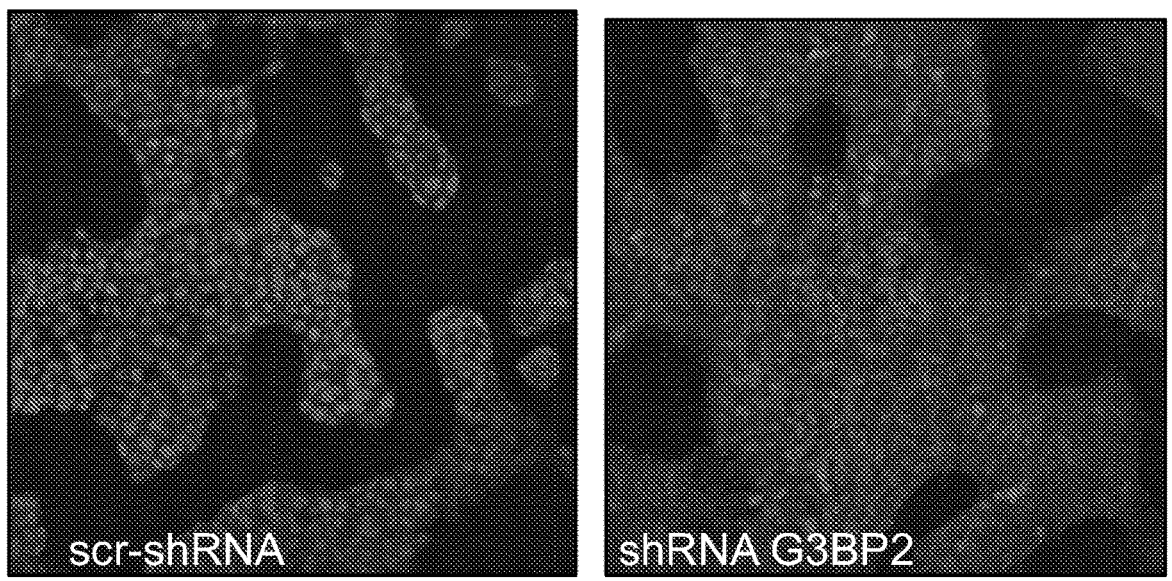
FIG. 3E shows representative pictures of immunofluorescence staining with ING4 antibodies using BT-474 scr-shRNA and G3BP2 shRNA cells grown in culture.
Figure 3F:
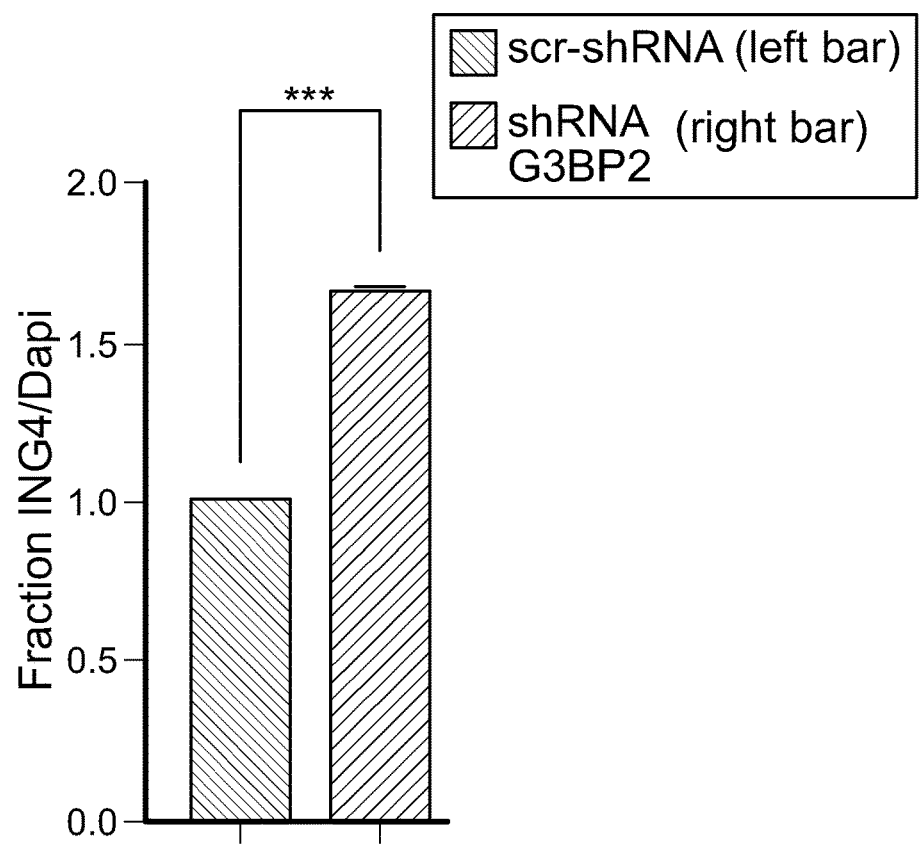
FIG. 3F shows quantification of immunofluorescence staining (error bars represent SEM; t test, n=3, ***P<0.001).

To confirm that G3BP2 binds to ING4, anti-G3BP2 antibodies were used to precipitate G3BP2 complexes from cellular extracts in cell lines MDA-MB-453 and BT-474. The presence of ING4 protein in precipitates was monitored by immunoblotting with a monoclonal antibody against ING4. ING4 co-immunoprecipitated with G3BP2, but not with control IgG, showing that ING4 and G3BP2 form a complex, as shown in FIG. 3C. To confirm this interaction and show that ING4 accumulates in the nucleus of G3BP2 silenced cells, we carried out immunoblotting with nuclear fractions and immunostaining experiments with two breast cancer cell lines, shown in FIG. 3D-3E. To confirm this data, immunofluorescence staining with ING4 antibodies were carried out and quantified, as shown in FIG. 3E-3F. The results show that knockdown of G3BP2 resulted in a substantial increase of ING4 in the nuclear fraction.

Example 10. ING4 Regulation of ZEB1

Figure 3G:
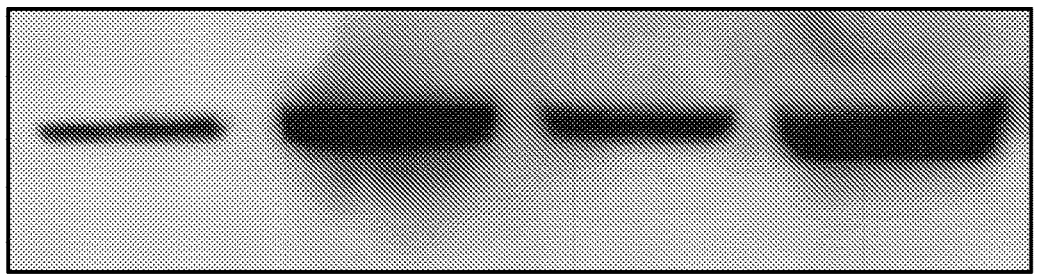
FIG. 3G shows a representative Western blot analysis performed on BT-474 and MDA-MB-453 cells with ING4 knock downs (2 different constructs; shRNA1 and shRNA2) and cells with a deletion of the PHD finger domain which shows that ING4 and its PHD domain regulate ZEB1 expression.
Figure 3G:
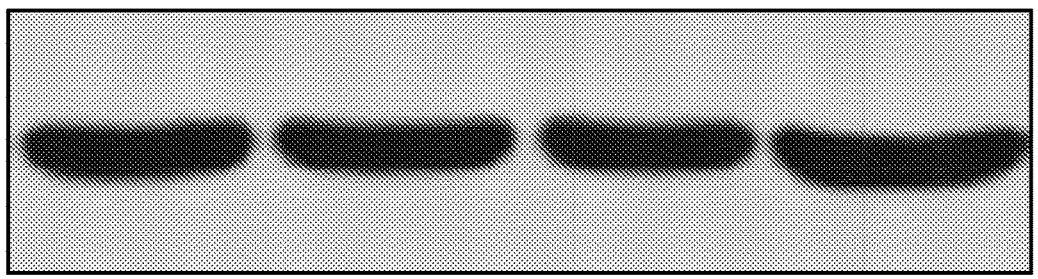
Figure 3G:
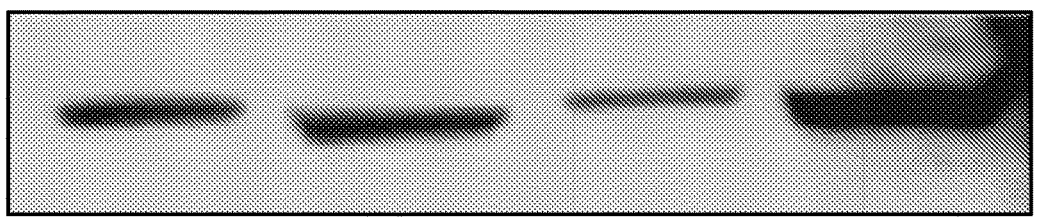
Figure 3G:
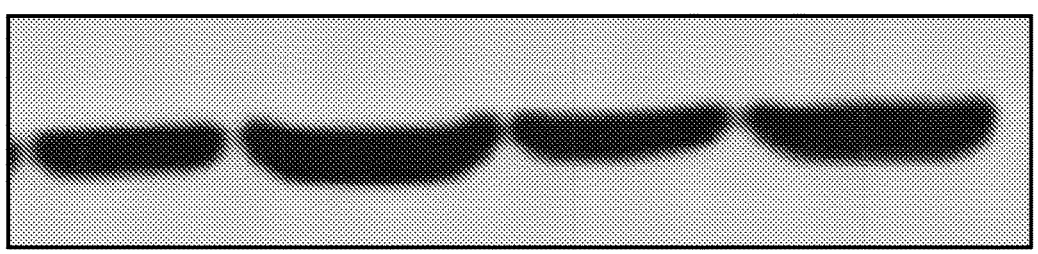

To evaluate whether ING4 also regulates the protein level of ZEB1, immunoblotting with cells containing different levels of ING4 was performed. As shown in FIG. 3G, knockdown of ING4 significantly increased ZEB1 protein levels. Since it is known that ING4 PHD finger-imbued recognition of H3K4Me3 is important in controlling transcription of target genes (see e.g., Hung et al., Molecular Cell, 2009, 33, 248-256), two cell lines were transfected with ING4 retroviruses lacking the PHI) finger (ING4-PHD). Western blot showed that the protein level of ZEB1 was not significantly changed after overexpression of ING4-PHD in two breast cancer cell lines with intact ING4 protein. The results collectively show that G3BP2 localizes the tumor suppressor ING4 to the cytoplasm, which decreases nuclear fractions of ING4 resulting in de-repression of ZEB1 transcription factor gene transcription.

Example 10. Chromatin Immunoprecipitation and ChIP Assay

It was further hypothesized that ZEB1 expression regulation by G3BP2 could be effected through chromatin reconfiguration at the ZEB1 promoter. To test this hypothesis, chromatin immunoprecipitation was used followed by quantitative real-time PCR (ChIP-qPCR) to examine the chromatin state at the ZEB1 promoter in cells with different expression levels of G3BP2. SimpleChIP Plus Enzymatic Chromatin IP Kit for chromatin purification and chromatin immunoprecipitation was used (Cell Signaling). Purified DNA was analyzed by quantitative real-time PCR. qPCR Primers for ChIP-qPCR Primer sequence (5'-3'):

```
ZEB1 (F)
                                    (SEQ ID NO: 1)
CCAGTTTGGAGAGACGTTGTAAG;

ZEB1 (R)
                                    (SEQ ID NO: 2)
CTCTCGCCACAGGAACTGTC;

K4 positive control (F)
                                    (SEQ ID NO: 3)
CTTGATTCTGAGGGTCAGGAG;

K4 positive control (R)
                                    (SEQ ID NO: 4)
GCTGATGCATAGGTCTGGAAG;

negative control (F)
                                    (SEQ ID NO: 5)
TGGATCTTGTGTCTGTCACTCC;

negative control (R)
                                    (SEQ ID NO: 6)
AAGTGGCAAGGGAGTTTAGTTG.
```

Figure 3H:
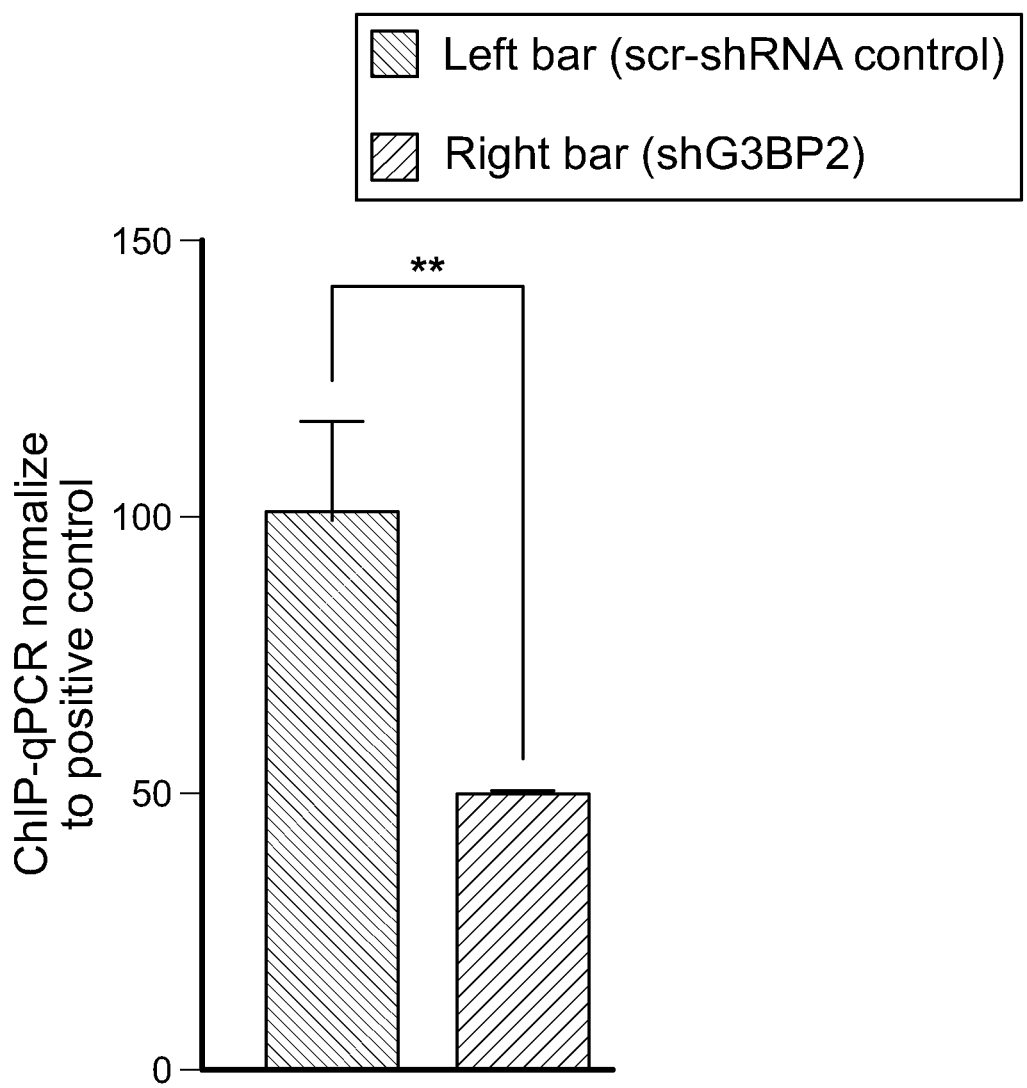
FIG. 3H shows G3BP2 changes the chromatin configuration of the ZEB1 promoter. The data shown is a result of four independent ChIP-qPCR experiments for H3K4me3 histone modification at the ZEB1 promoter with MDA-MB-453 cells. The ChIP-qPCR assay with control (blue bars) and cells with G3BP2 knock down (red bars). Error bars represent SEM.
Figure 3I:
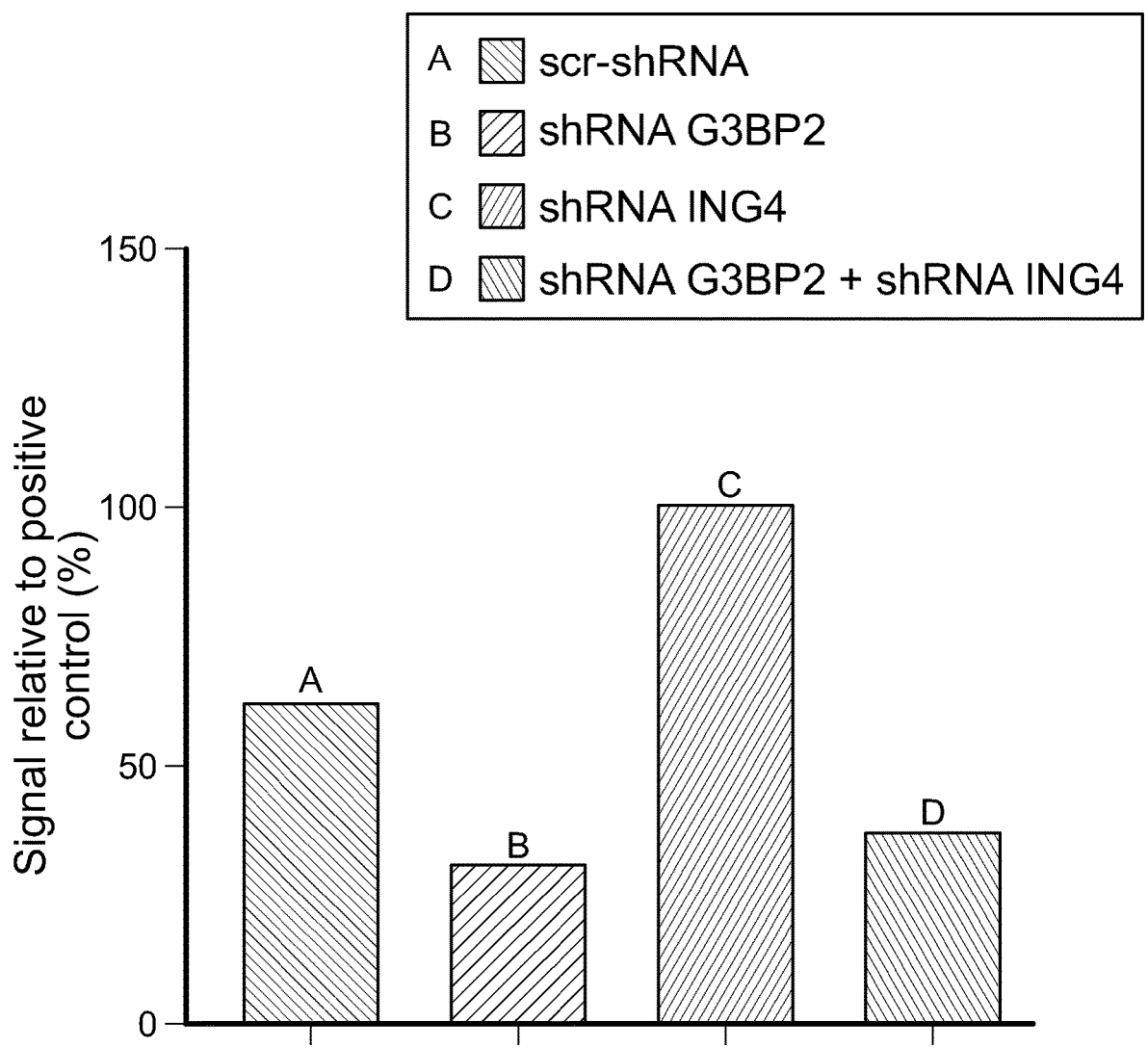
FIG. 3I shows ChIP-qPCR for H3K4me3 histone modification at the ZEB1 promoter in MDA-MB-453, MDA-MB-453 shG3BP2, MDA-MB-453 infected with shING4 lentivirus and MDA-MB-453 shG3BP2 cells infected with shING4 lentivirus.
Figure 3J:
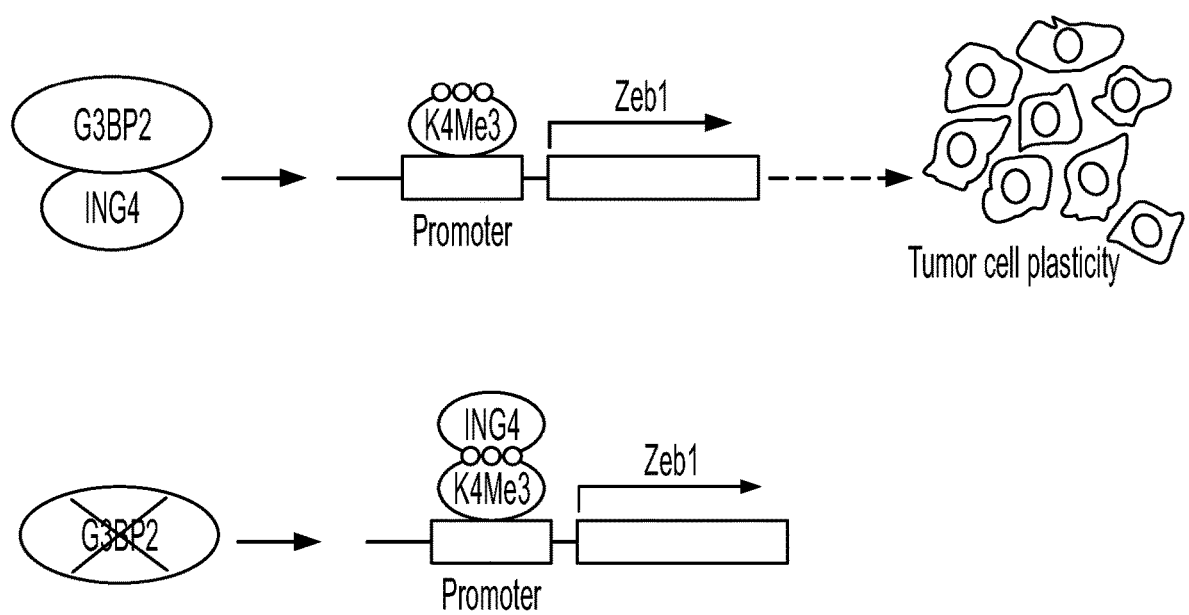
FIG. 3J show a schematic overview of ZEB1 regulation by G3BP2.

First, cells with control vector and shG3BP2 cells were analyzed, and found that changes of G3BP2 expression lead to alteration of the chromatin methylation pattern at the ZEB1 promoter. The G3BP2 shRNA cells displayed decreased levels of H3K4me3, indicating repressed transcription of ZEB1, as shown in FIG. 3H. To confirm that G3BP2 affects H3K4me3 in the ZEB1 promoter through ING4, a ChIP-qPCR assay with knock down G3BP2 and ING4 in MDA-MB-453 cells was performed, as shown in FIG. 3I (see e.g., Chaffer et al., Cell, 2013, 154, 61-74). These data indicate that G3BP2 modulations can indirectly change chromatin marks in the ZEB1 promoter. These results are in agreement with previous studies suggesting that ZEB1 transcriptional activity helps non-CSCs enter a CSC state. The consequences of G3BP2-ING4 interaction on ZEB1 activity and tumor cell plasticity are schematically illustrated in FIG. 3J. ING4 represses ZEB1 activity through binding to H3K4me3 in the ZEB1 promoter via the P1-ID finger domain and stabilizing the mSin3a-HDAC1 histone deacetylase complex at the promoter. Up-regulation of G3BP2 and accumulation of this protein in cytoplasm decreases the nuclear fraction of ING4 protein through binding to G3BP2. As a result of a G3BP2-ING4 complex, the H3K4me3 sites in the ZEB1 promoter region will be available for other interactions.

Figure 7B:
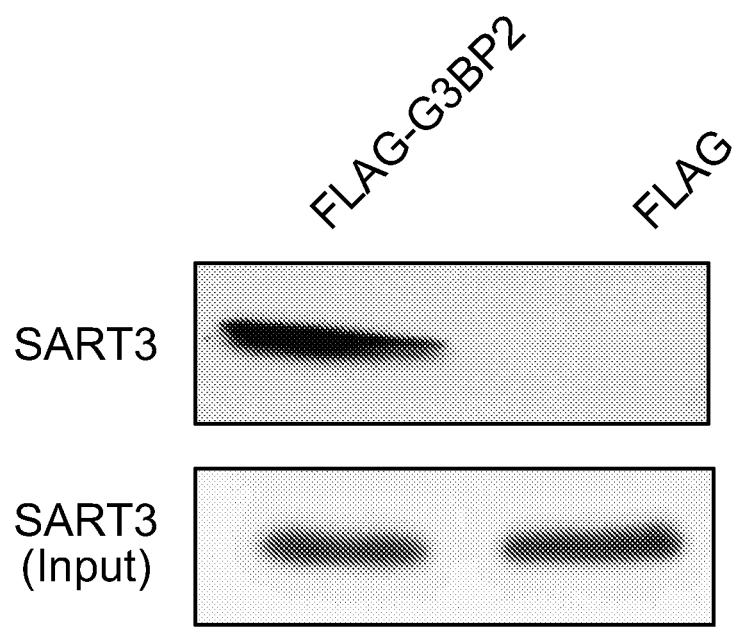
FIG. 7B shows the physical interaction between G3BP2 and SART3, confirmed by immunoprecipitation with FLAG-G3BP2 and FLAG constructs transfected to the HEK-293T cells.
Figure 7C:
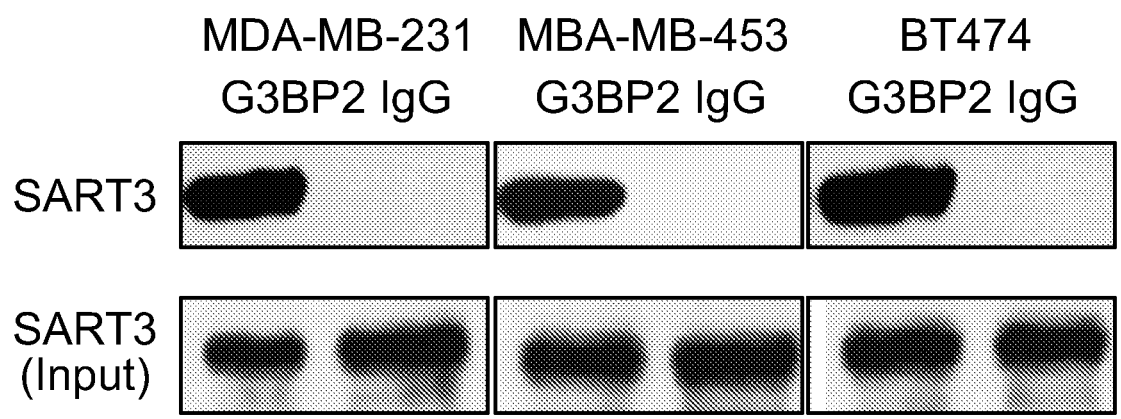
FIG. 7C shows immunoprecipitations performed with G3BP2 and IgG antibodies with protein lysates from three breast cancer cell lines and used for Western blotting with SART3 antibodies.
Figure 8A:
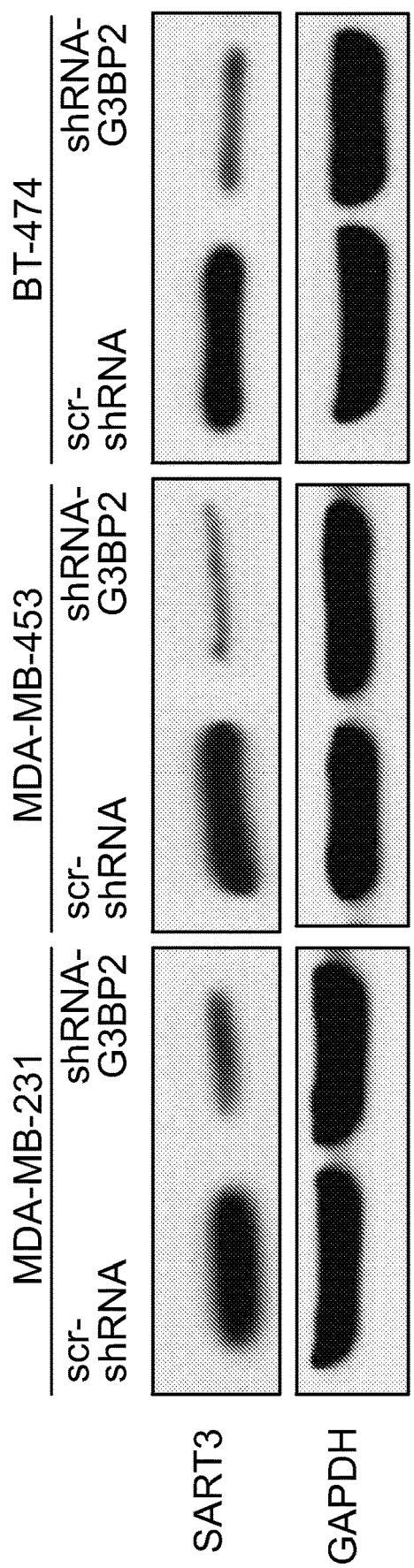
FIG. 8A shows G3BP2 depletion by shRNA leading to decreased protein level of SART3 in MDA-MB-231, MDA-MB-453 and BT474 cells.
Figure 8B:
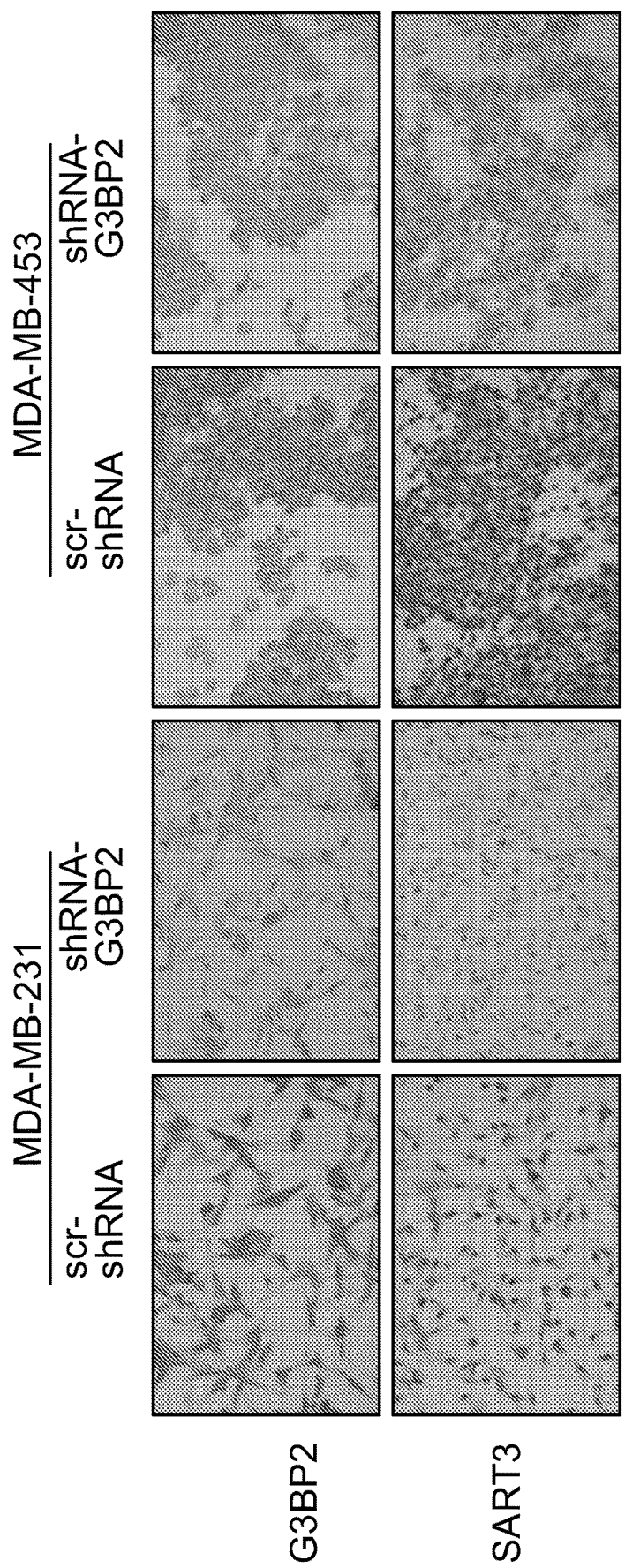
FIG. 8B-8C shows immunocytochemistry (FIG. 8B) and fluorescent immunocytochemical staining (FIG. 8C) performed to determine the expression of SART3 in G3BP2 depletion cells and control cells (magnification, ×200, scale bar=20 μm).
Figure 8C:
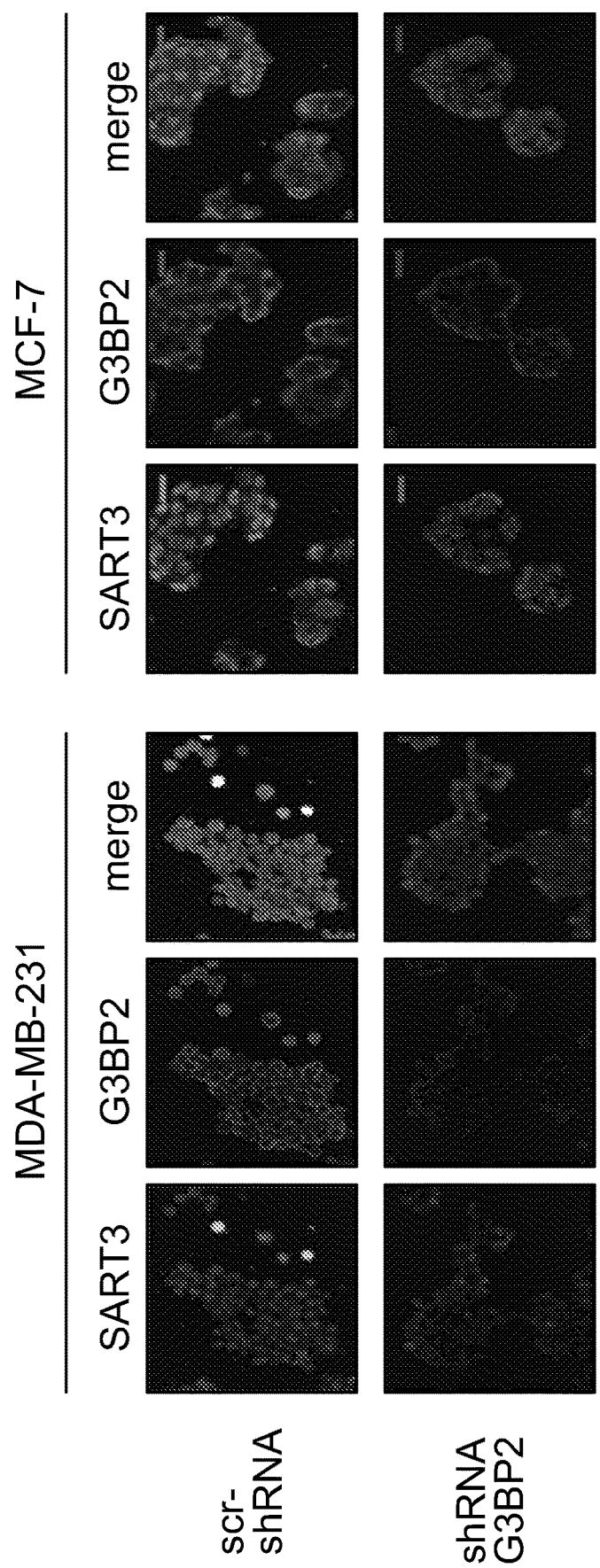

Example 11. G3BP2 Controls SART3 (Squamous Cell Carcinoma Antigen Recognized by T Cells) Expression Nanog, Oct4 and Sox2 are transcriptional factors that determine pluripotance and self-renewal of embryonic stem cells. It has previously been shown that SART3 protein is necessary for maintenance of expression of Nanog, Oct4 and Sox2 and it plays important role in preserving of embryonic stem cells pluripotancy. Analysis of whether G3BP2 protein affects SART3 expression (FIGS. 7A-7C) and subsequently expression of Nanog and Oct4 was tested. The MDA-MB231, MDA-MB-453 and BT-474 cells with downregulation of G3BP2 and cells with control scrambling shRNA were used for detection of SART3 expression. Western blotting results indicate that G3BP2 downregulation leads to repression of SART3 expression, as shown in FIG. 8A. To further confirm the effect of G3BP2 on SART3 expression, immunocytochemistry (IHC) and immunofluorescence was used. The results demonstrate that G3BP2 depletion reduce level of SART3 protein compared with the control cells, as shown in FIGS. 8B-C. Together, these findings indicate that downregulation of G3BP2 leads to repression of SART3 protein in breast cancer cells.

Example 12. G3BP2 Regulates OCT4 and Nanog Expression

Figure 9A:
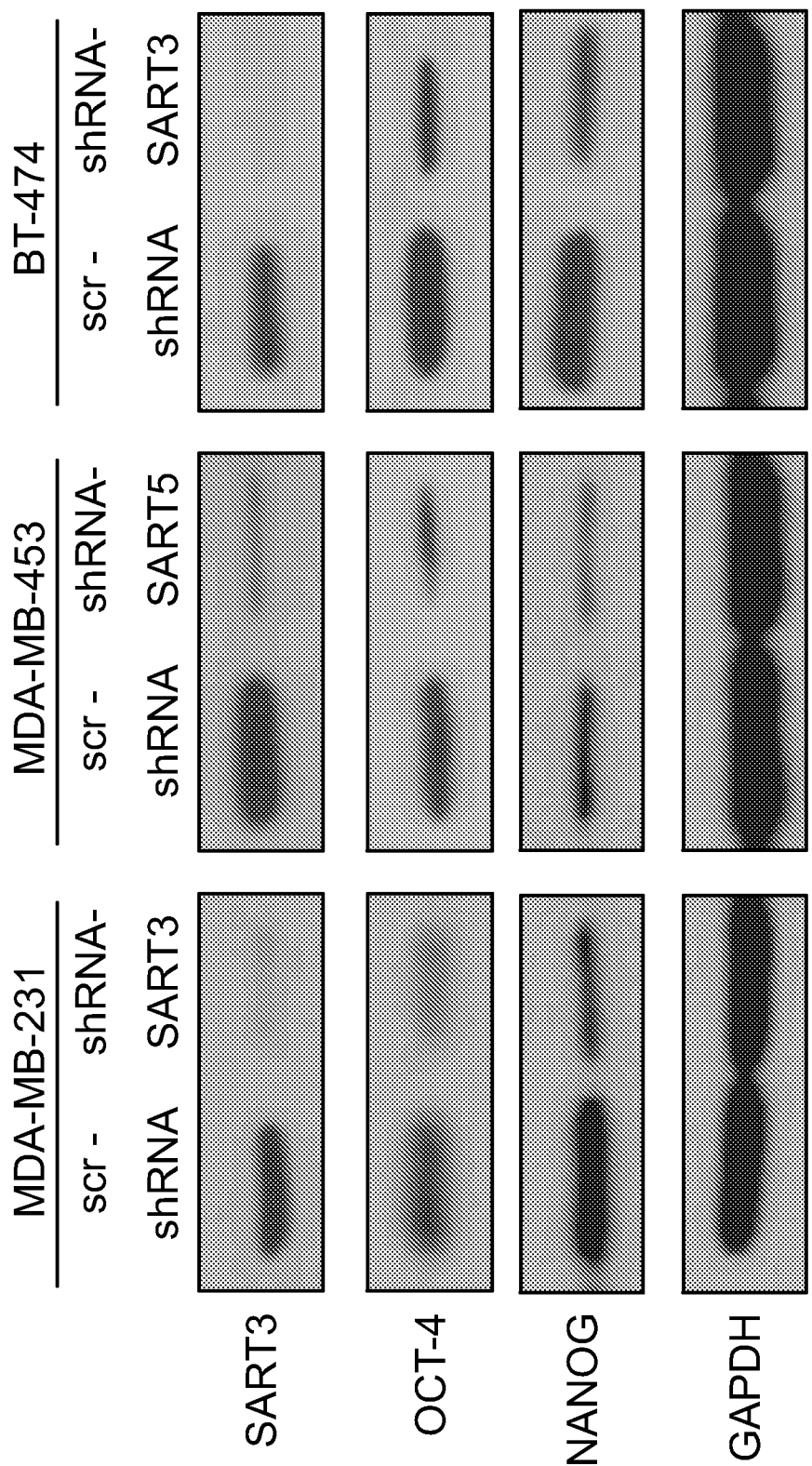
FIG. 9A shows a Western blot analysis performed to detect OCT4 and Nanog expression in SART3 depleted breast cancer cell lines.
Figure 9B:
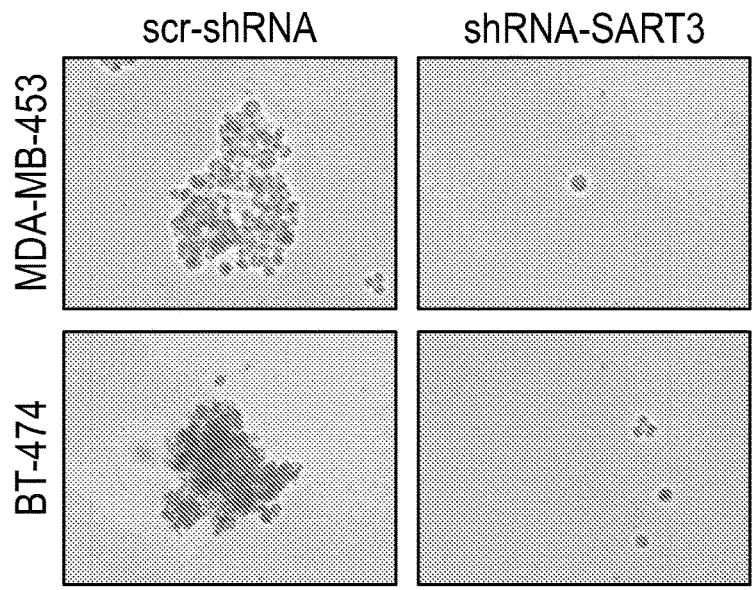
FIG. 9B-9C show representative images and data of mammosphere forming units observed in SART3 depletion BT-474 and MDA-MB-453 cells. Data are mean±SD, *p<0.05, **p<0.005. Magnification ×200.
Figure 9C:
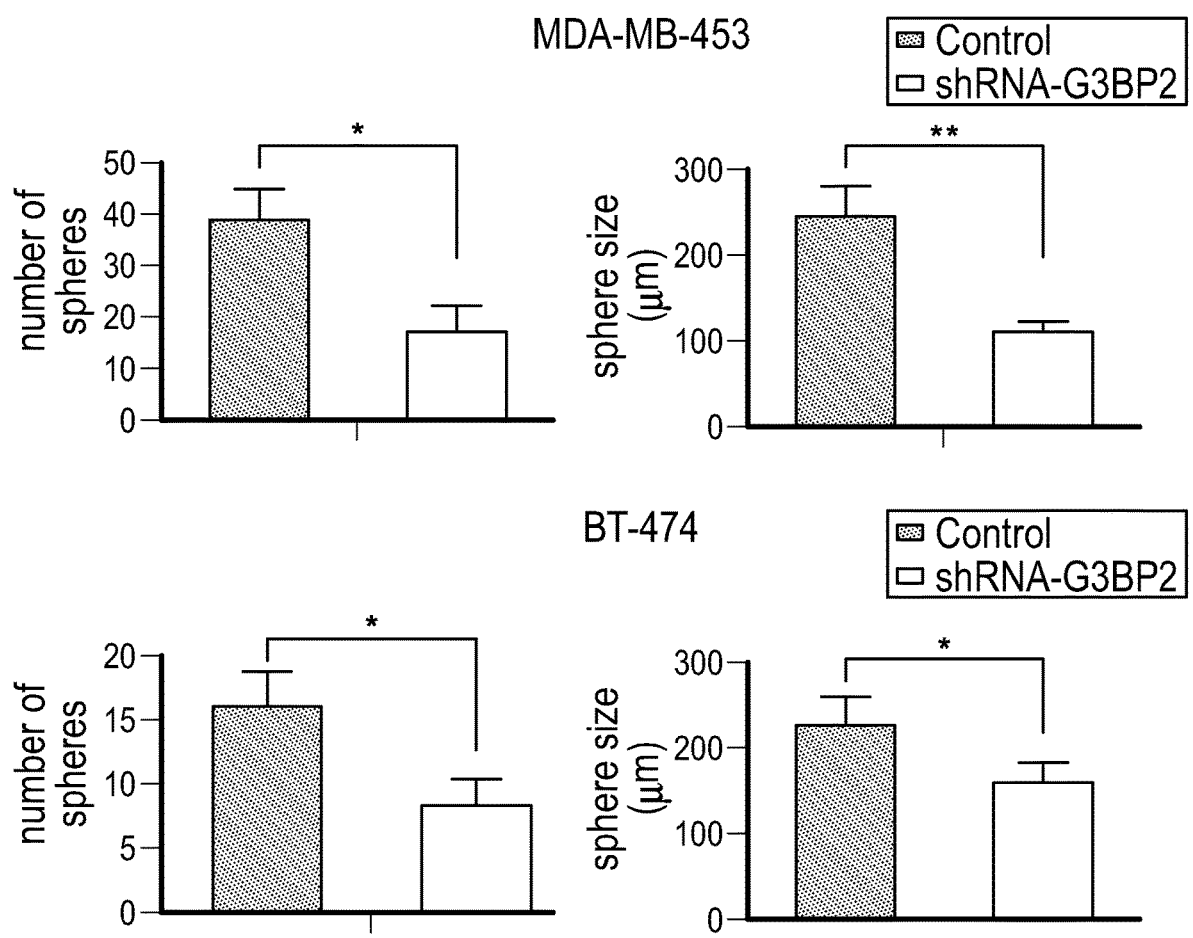
Figure 9D:
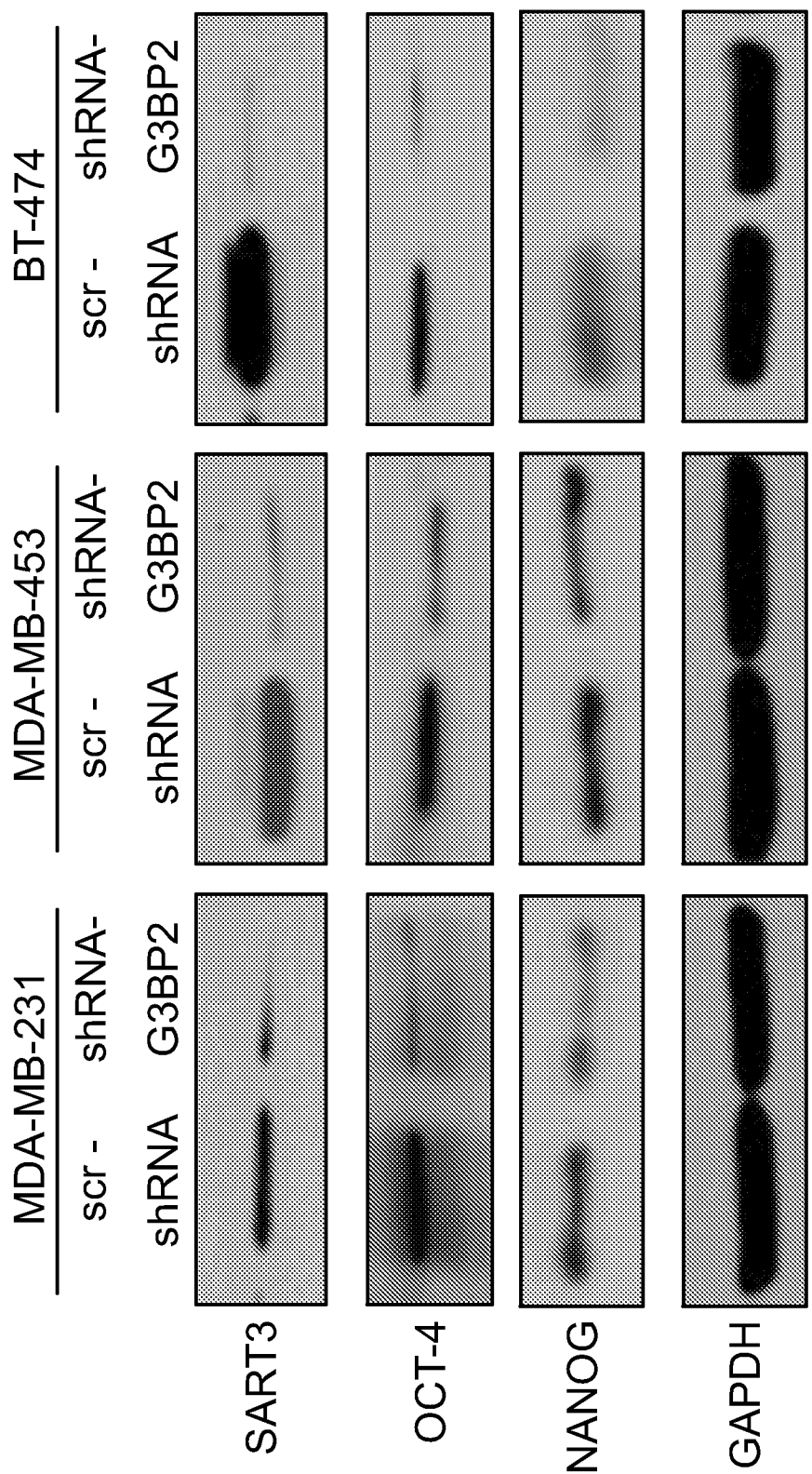
FIG. 9D shows a Western blot analysis performed to detect OCT4 and Nanog expression in SART3 depleted breast cancer cell lines.
Figure 10:
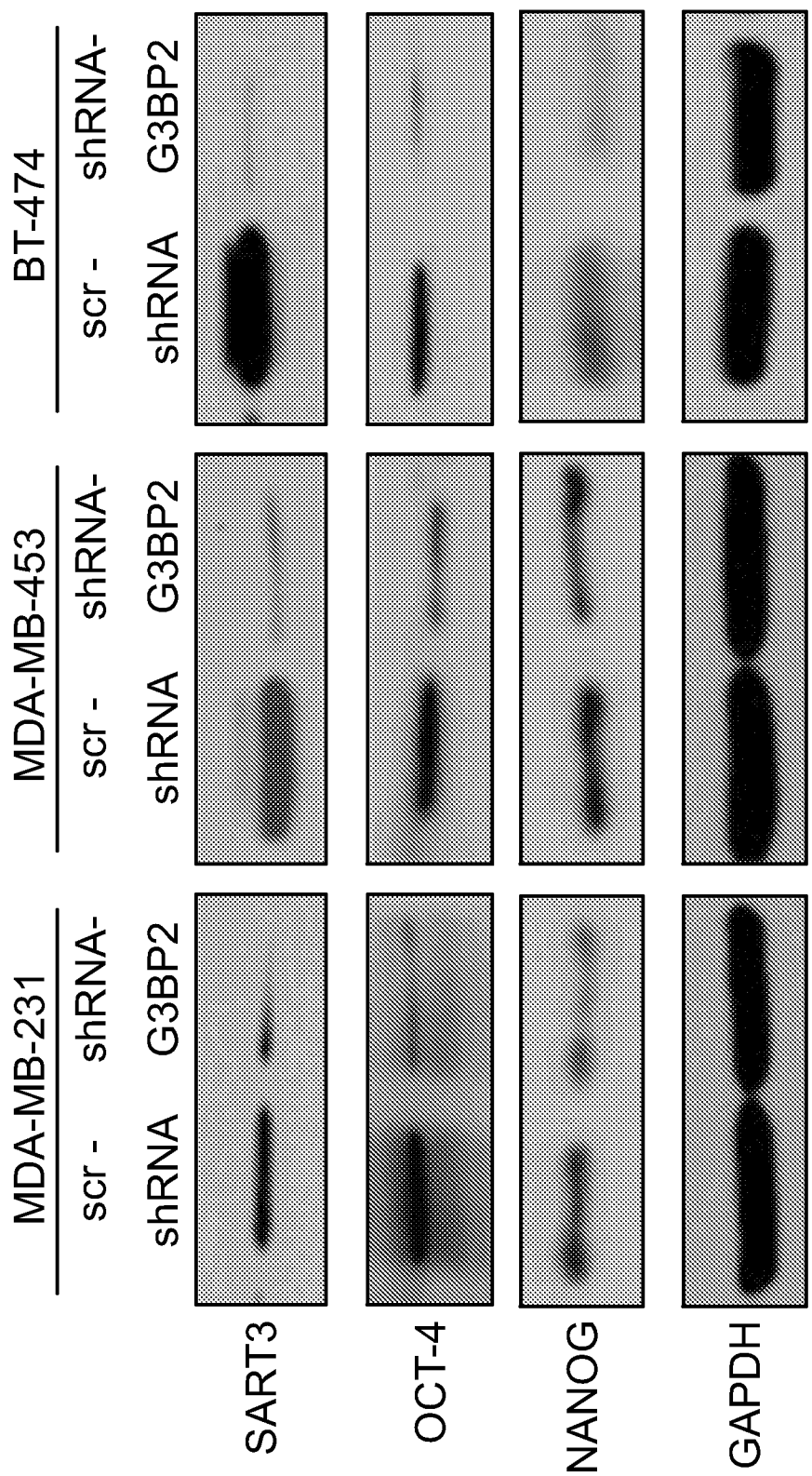
FIG. 10 shows Western blot analysis performed with OCT4 and NANOG antibodies in three breast cancer cell lines with different level of G3BP2 expression.

To confirm that alterations in SART3 expression in the in vitro models effect embryonic stem cell transcriptional factors, the expression level of Nanog and Oct4 in three breast cancer cell lines with repression of SART3 was analyzed. Cells infected with scramble shRNA retroviruses were used as control cells. The SART3 repression (shRNA-SART3) induced decreased expression levels of pluripotent transcriptional factors OCT4 and Nanog, as shown in FIG. 9A. To test whether G3BP2 protein also affected expression of Nanog and Oct4, the same breast cancer cells with down-regulation of G3BP2 and cells with control scrambling shRNA were used for detection of OCT4 and Nanog expression, as shown in FIG. 9D and FIG. 10. These data indicated that repression of G3BP2 decrease OCT4 and Nanog expression. If G3BP2 regulate OCT4 and Nanog expression through SART3 protein, it can be predicted that modulation of the SART3 expression will lead to changes of mammosphere formation. To verify, sphere formation assays with BT474 and MDA-MB-453 cells were performed and the results are shown in FIGS. 9B-9C. Repression of SART3 expression with shRNA shRNA-SART3 cells showed lower sphere forming ability in two breast cancer cell lines compare to control cells (*P<0.05 vs. wild and control).

Figure 11A:
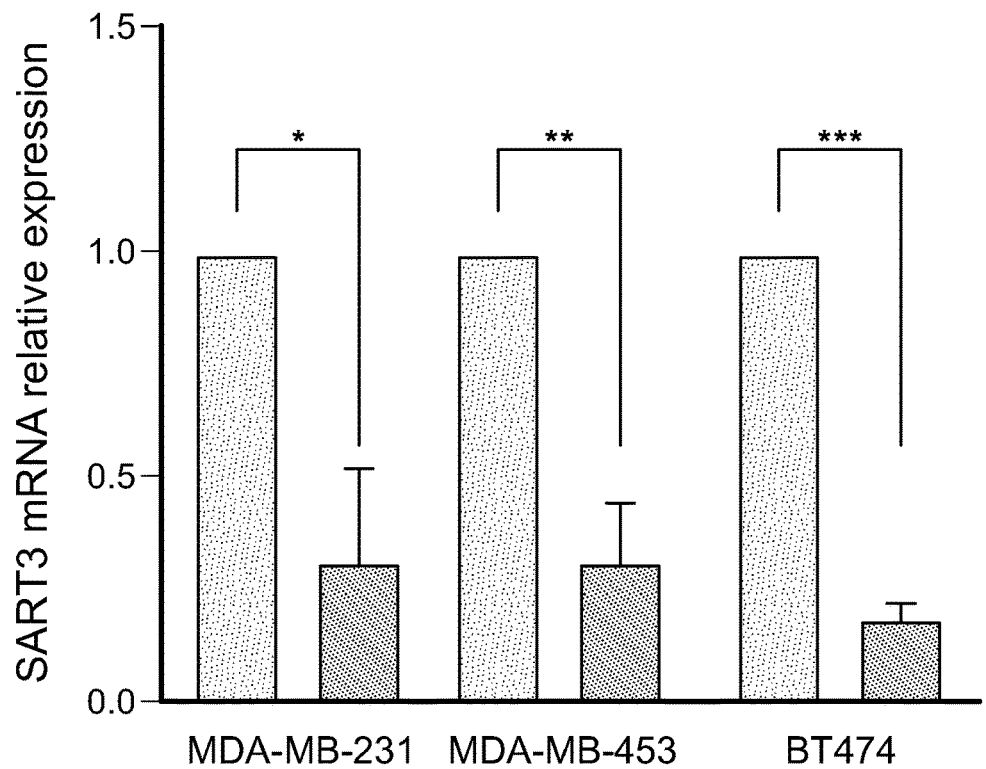
FIG. 11A shows SART3 primers used for detection of SART3 mRNA in RT-PCR reaction from cells with downregulation of G3BP2 (left bars) in three different breast cancer cell lines.
Figure 11B:
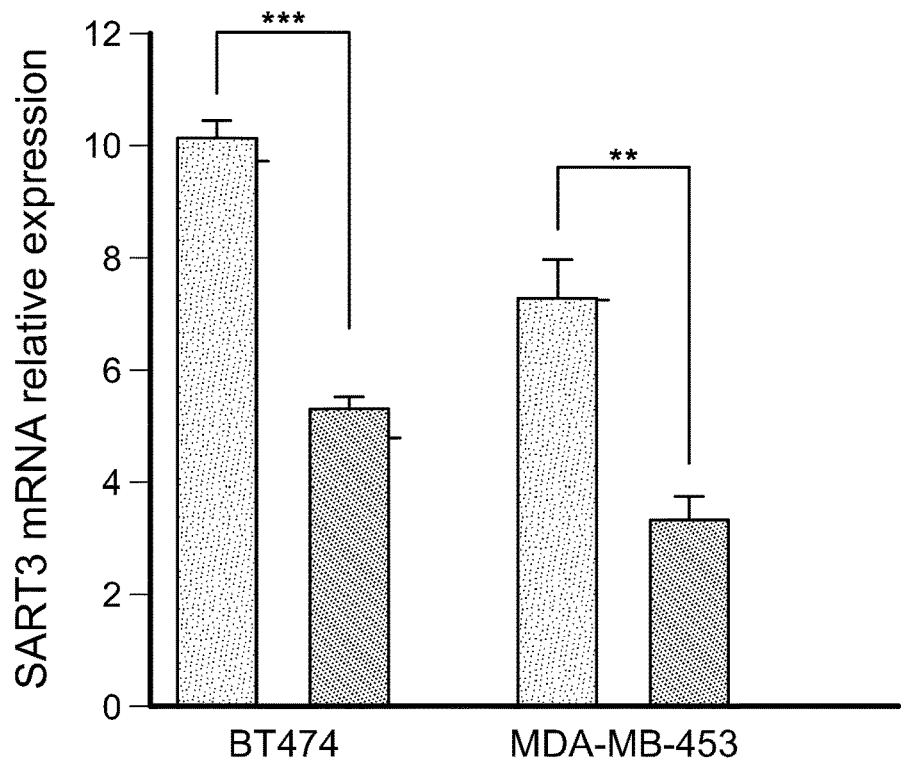
FIG. 11B shows a representative RNA immunoprecipitation (RIP) assay with BT-474 and MDA-MB-453 cell lysates with downregulation of G3BP2 (left bars). The anti-G3BP2 and anti-IgG and antibodies were used for this RIP assay. SART3 and GAPDH mRNAs were quantified using RT-PCR and were represented as fold enrichment compared with control IgG for RIP assay.

Example 13. G3BP2 Inhibits the Degradation of SART3 mRNA Through RNA Binding Motif G3BP2 is one of the RNA-binding protein with RNA recognition motif (RRM) that involved in stress granule formation. The data provided herein show that G3BP2 has effect on SART3 protein level. To test whether G3BP2 regulates SART3 through mRNA, SART3 mRNA level was analyzed using RT-PCR with primers specific for SART3 gene in cells with different expression level of G3BP2. It was found that SART3 mRNA level was decreased in cells with downregulation of G3BP2, as shown in FIG. 11A. The statistical significance of SART3 mRNA expression levels in cells with G3BP2 suppression compare to control cells was reversely correlated with efficiency of G3BP2 repression. These results suggest that G3BP2 may stabilize SART3 mRNA. To test this hypothesis, BT-474 and MDA-MB-453 parental cells were transfected with shRNA-G3BP2 and used for RNA immunoprecipitation. Total mRNAs combined with G3BP2 were pulled down and SART3 mRNA was detected by qPCR. Compared with wide-type control, SART3 mRNA level was substantially reduced which shows the potential regulation between G3BP2 and SART3 mRNA, as shown is shown in FIG. 11B. Together, these findings indicate that G3BP2 not only has effect on mRNA level of SART3 but also physically interacts with mRNA.

Figure 11C:
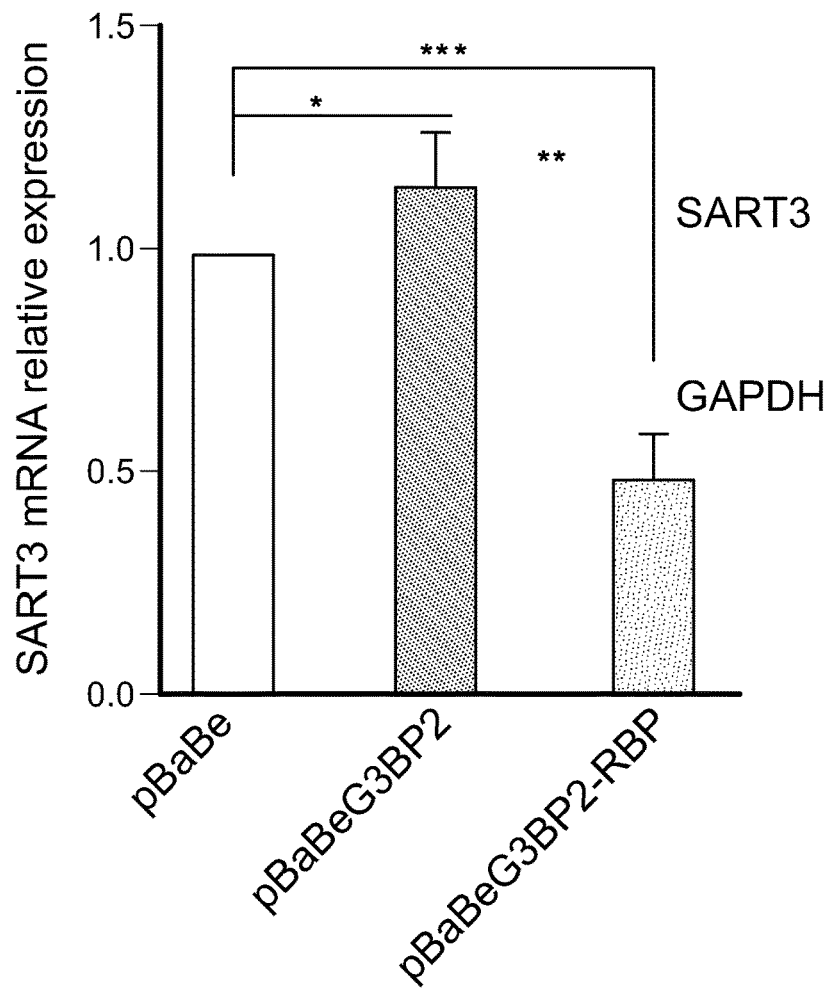
FIG. 11C shows a representative retroviral construct with full length of G3BP2 full length, retrovirus with deletion of RNA binding motif of the G3BP2 gene (Δ1) and retrovirus alone infected to MCF-7 cells. RT-PCR was performed to detect SART3 mRNA changes.
Figure 11D:
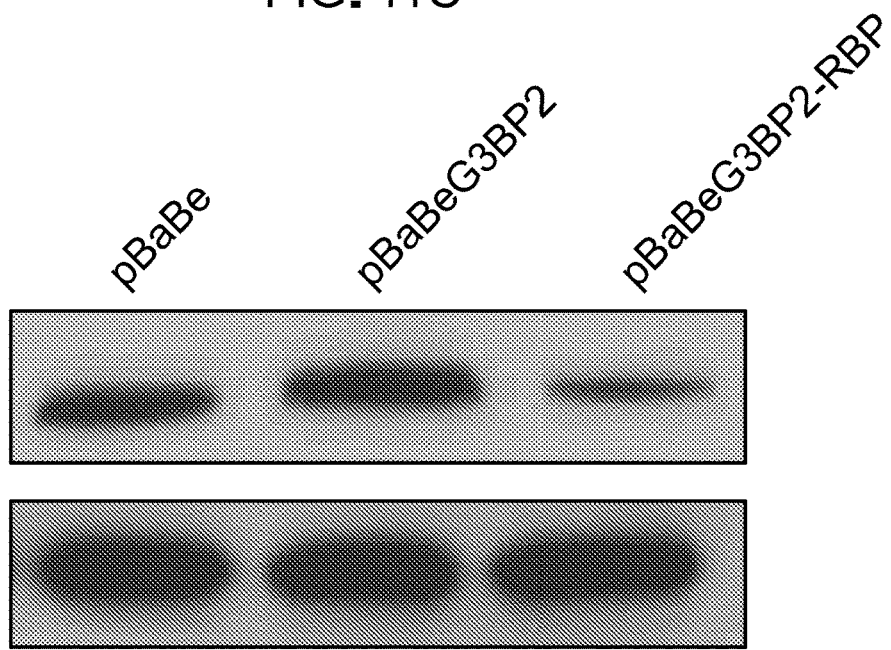
FIG. 11D shows a representative Western blot analysis of SART3 protein in MCF-7 cells with different retroviral constructs. Data are mean±SD, *p<0.01, **p<0.001.

To further determine the binding site of SART3 mRNA, G3BP2 without RRM sequence was constructed and ligated into the expression plasmid pBaBe (A1). The pBaBe-G3BP2 full-length and pBaBe-mock were also created as positive and negative control, respectively. They were stably transfected into MCF-7 cells. RT-qPCR and Western blot assays showed increased expression of SART3 in pBaBe-G3BP2 full-length group that was in accordance with the regulation of G3BP2 and SART3, as shown in FIG. 11D. Moreover, SART3 mRNA and protein were found significantly reduced in RRM deficient cells, as shown in FIG. 11C. These results demonstrate that G3BP2 stabilized SART3 mRNA from degradation through RNA binding motif.

Figure 4:
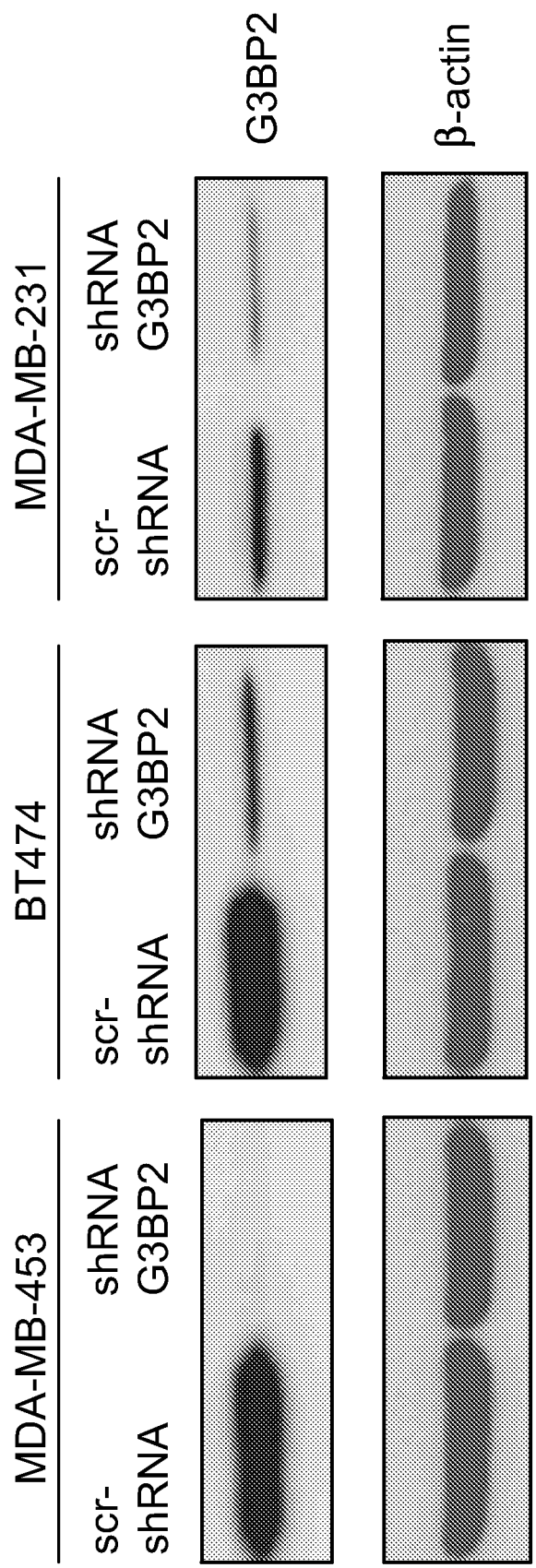
FIG. 4 shows a representative Western blot analysis with antibodies against G3BP2 protein with 20 μg of protein lysates from stable cell lines cells with G3BP2 shRNA knockdown and scr-scr-shRNA controls. β-actin was used as loading control.
Figure 13A:
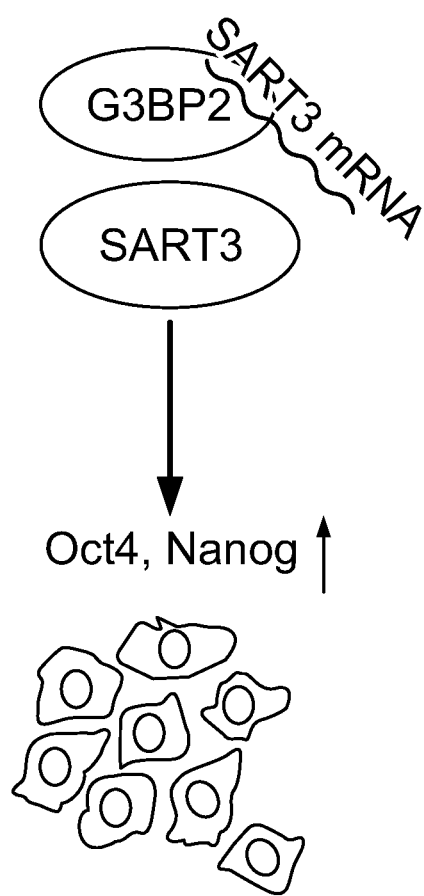
FIGS. 13A-B show a molecular model of G3BP2-SART3 regulation of cancer stem cell phenotype.
Figure 13B:
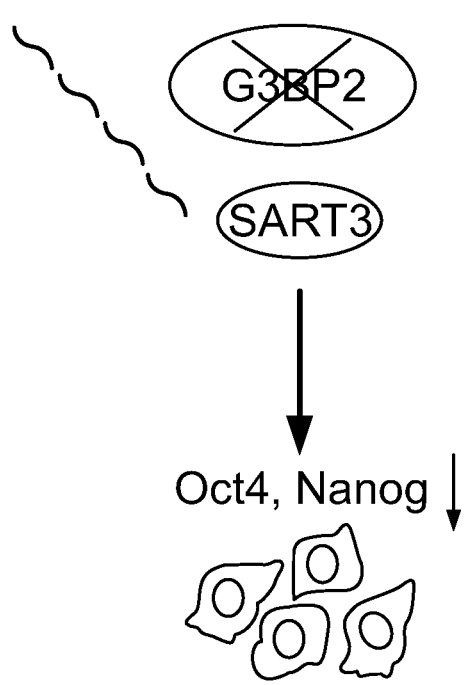

Example 14. G3BP2 and SART3 Regulate OCT4 and Nanog Expression and Mammosphere Formation The effects of G3BP2 (FIG. 4) and SART3 (FIG. 9A) knockdown in MDA-MB231, MDA-MB-453 and BT-474 breast cancer cells was studied using shRNA. Compared with scramble sequence-transfected control cells, G3BP2 or SART3 depletion (shRNA-G3BP2 and shRNA-SART3) induced decreased expression levels of pluripotent factors including OCT4 and Nanog, as shown in FIG. 9A. Accordingly, sphere formation assays were carried out to examine the sternness of breast cancer cells. shRNA-SART3 cells showed lower sphere forming ability than control cells which was in accordance with the effect of G3BP2, as shown in FIGS. 9B-9C (*P<0.05 vs. wild and control). FIG. 13A-B show a molecular model of G3BP2-SART3 regulation of cancer stem cell phenotype.

Example 15. Clinical Samples

Figure 12:
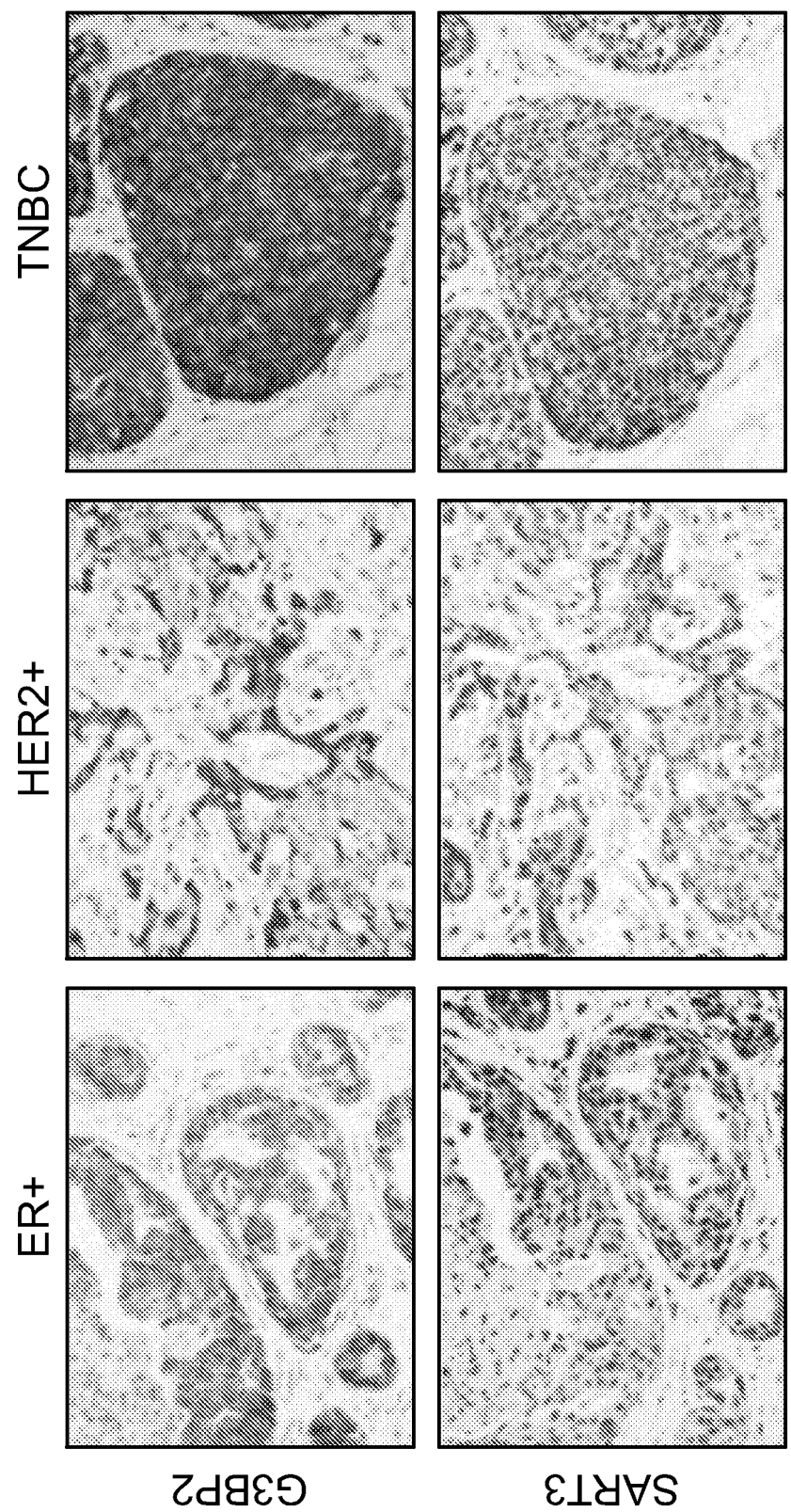
FIG. 12 shows immunohistochemistry of G3BP2 and SART3 in breast cancer tissues (magnification ×200). Correlation between G3BP2 and SART3 expression in breast cancer tissues (n=56, p<0.0001).

Accordingly, the expression of G3BP2 and SART3 in a cohort of 56 breast cancer patients by IHC staining was assessed, as is shown in FIG. 12. Prominent nuclear staining of SART3 and cytoplasmic staining of F3BP2 were observed and the expression intensity was measured by H-score. In correspondence with the in vitro data provided herein, G3BP2 expression level appears to correlate with SART3 expression, as is shown in FIG. 12 (r=0.2626, P<0.0001). There were no significant correlations between the two proteins in pathological subgroups. (The Spearman correlations and Wilcoxon rank-sum tests were used to assess the associations between H-score of SART3 and G3BP2.)

Example 16. Compressive Stress Model in Mammary Carcinoma Cells

Mechanical stress is expected to play an important role in progression of breast carcinomas, as matrix stiffness has been shown to regulate malignant transformation of mammary epithelial cells. Under different types of stress such as hypoxia, nutrient deprivation, solid stress, or chemical poisoning, cells form structures known as stress granules (SGs). SGs are dense aggregations in the cytoplasm composed of RNA and RNA-binding proteins including G3BP1 and G3BP2 and function to protect RNAs from harmful conditions. Stress granules also function as a decision point for untranslated mRNAs for further storage, translation reprogramming, or degradation. Because solid stress affects tumor growth, invasion, metastasis, a compressive stress model was performed. Stress models appear to recapitulate several features of in vivo behavior that may be lost in traditional culture methods.

Figure 15A:
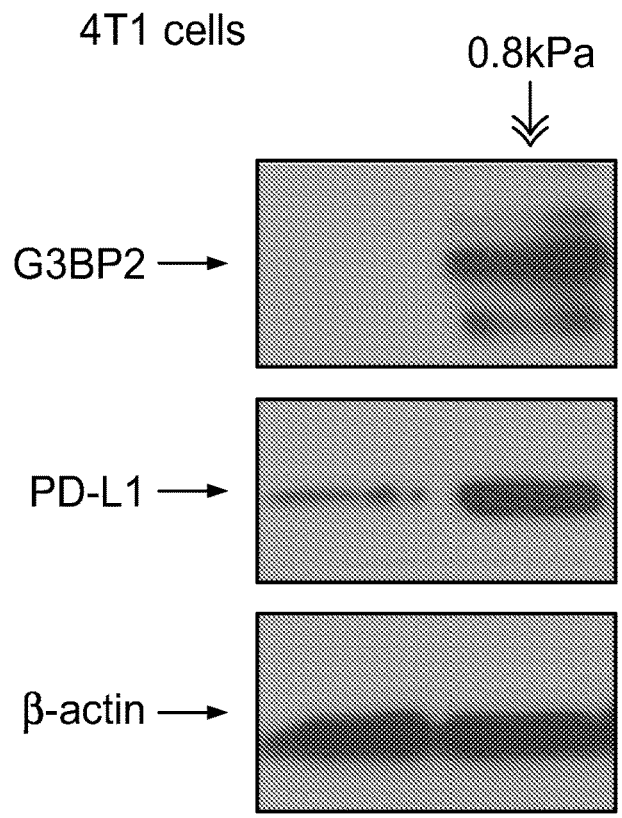
FIG. 15A shows Western blot analysis of G3BP2 and PD-L1 proteins in two different breast cancer cells with or without solid stress (4T1 and MDA-MB-231 cells). The protein lysates were resolved in a 12% gradient gel and transferred them to a PVDF membrane. Primary antibodies (anti-G3BP2, or anti-PD-L1) were added to bind to the protein overnight at 4° C., followed by incubation with HRP-conjugated secondary antibodies.
Figure 15B:
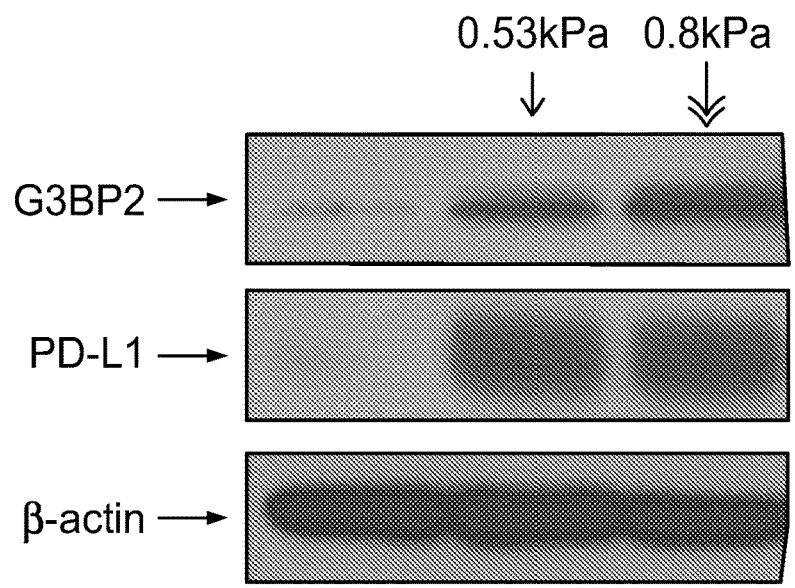
FIG. 15B shows that expression levels of G3BP2 and PD-L1 depended on compressive stress. The single arrow is 0.53 kPa and double arrow is 0.80 kPa. β-actin was used as a loading control.

To generate compressive stress, a device was used that included a piston of adjustable weights applying a constant force to cells growing on a transwell membrane with 0.8 μm-pores. This membrane permitted nutrient and oxygen diffusion but prevented cell transmigration. The connection between compressive stress and G3BP2 and PD-L1 protein levels was measured in 4T1 cells. When 80% cell confluence was reached on the membrane, the cells were compressed for 24 h using the in vitro compression device; a similar membrane containing 80% cell confluence in an uncompressed condition was used as the control. After 24-h compression, proteins were isolated from the control and compressed cells cultured in full-growth medium according to the standard protocol (see e.g., Roose et al. *Microvasc Res*, 2003, 66(3):204-12). It was found that applied compressive stress enhanced expression of G3BP2 and PD-L1 protein expression in human and mouse breast cancer cells, as shown in FIG. 15A. To confirm this finding, Western blot analysis was performed with different breast cancer cells (MDA-MB-231 cells) with different of compressive stress, as shown in FIG. 15B). Together, these observations indicated that G3BP2 and PD-L1 protein expression depended on solid stress.

Figure 15C:
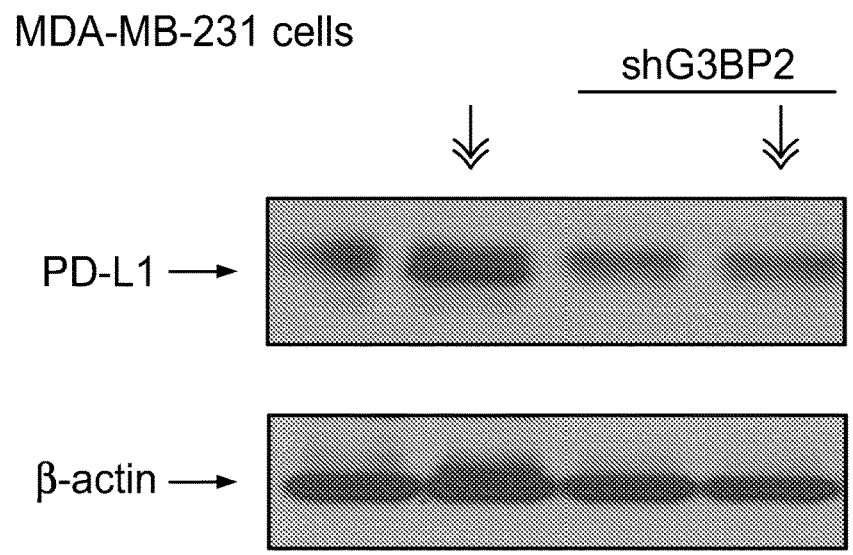
FIG. 15C shows PD-L1 protein expression depended on the level of G3BP2 protein in stressed cells. Silencing of G3BP2 resulted in unchanged protein levels of PD-L1 protein in MDA-MB-231 cells breast cancer cells under compressive stress in vitro. Knock down of G3BP2 inhibited response of PD-L1 protein in MDA-MB-231 cells to compressive stress.

To assess whether the protein level of PD-L1 depended from G3BP2 protein in stressed cells, G3BP2 was repressed with shRNA. G3BP2 diminution by shRNA in the breast cancer cell line MDA-MB-231 was significant, resulting in inhibition of PD-L1 protein response to compressive stress, as shown in FIG. 15C. Without being bound by any theory, these results suggested that modulating G3BP2 expression in stressed breast cancer cells affected the expression of PD-L1 protein.

Example 17. Inhibition of PD-L1 in Stressed Cells

Figure 16:
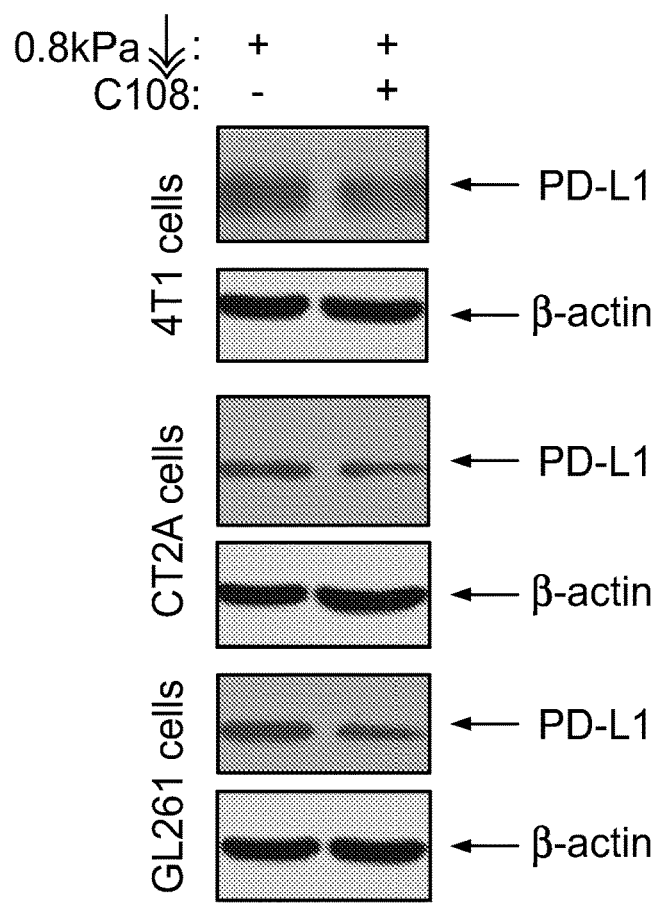
FIG. 16 shows that 2-hydroxy-N'-[1-(2-hydroxyphenyl) ethylidene]benzohydrazide (i.e., C108) repressed PD-L1 in breast cancer (4T1) and glioblastoma cells (CT2A, GL261) with solid stress (0.80 kPa). Cells were treated with 1 µM C108 for 24 hours and untreated cells were used as a control. β-actin was used as a loading control.

It was then hypothesized that compounds that bind to G3BP2 protein can repress PD-L1 in stressed cells. Breast cancer cells and glioblastoma cells in vitro were analyzed with 2-hydroxy-N'-[1-(2-hydroxyphenyl)ethylidene]benzohydrazide (i.e., $C_{108}$) for 24 hours. PD-L1 protein levels were then measured in stressed cells using Western blotting, as shown in FIG. 16. It was found that C108 diminished expression level of PD-L1, and that this effect was observed in the different type of cancers, suggesting that compounds that bind to G3BP2 protein may be useful for treatment of the tumors.

Example 18. IL-6 Concentration

Figure 14:
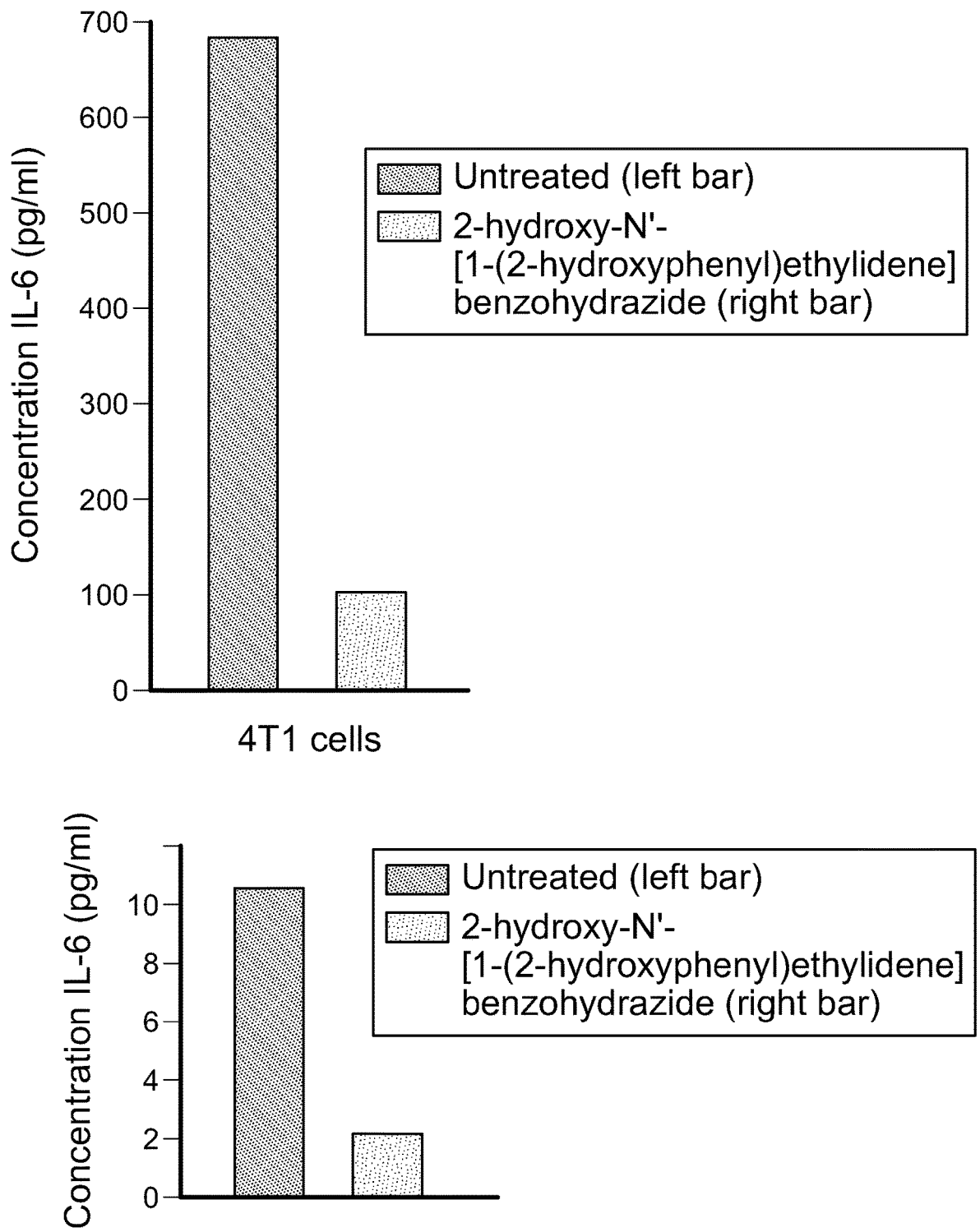
FIG. 14 shows a decrease in IL-6 concentration upon treatment of two breast cancer cell lines (4T1 and E0771) with 2-hydroxy-N'-[1-(2-hydroxyphenyl)ethylidene]benzohydrazide over 24 hours. After treatment, IL-6 concentration was decreased by about 5 to 7 fold.

4T1 and E0771 cells were grow in 96 well plate and were treated with compound for 24 hours (concentration of compound was 1 μM). Commercial ELISA kit (R&D systems) was used for measuring of IL-6 concentration. Results of the IL-6 assay are shown in FIG. 14. It was found that IL-6 concentration decreased upon treatment of the two breast cancer cell lines with 2-hydroxy-N'-[1-(2-hydroxyphenyl) ethylidene]benzohydrazide (i.e., C108) over 24 hours. After treatment, IL-6 concentration was decreased by about 5 to 7 fold.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a breast cancer, the method comprising administering to a patient in need thereof a therapeutically effective amount of a compound having the formula:

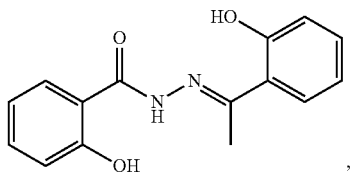 [SMILES: C/C(=N\NC(=O)c1ccccc1O)c1ccccc1O]

or a pharmaceutically acceptable salt thereof.

2. A method of reducing metastasis of a breast cancer in a patient, the method comprising administering to the patient in need thereof a therapeutically effective amount of a compound having the formula:

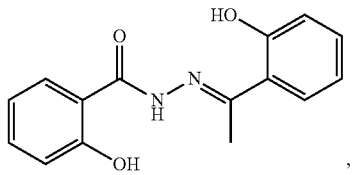 [SMILES: C/C(=N\NC(=O)c1ccccc1O)c1ccccc1O]

or a pharmaceutically acceptable salt thereof.

3. The method of claim 1, wherein the breast cancer is selected from: breast cancer associated with overexpression of G3BP2, breast cancer associated with overexpression of ZEB1, breast cancer associated with overexpression of G3BP2 and overexpression of ZEB1, breast cancer associated with overexpression of G3BP1, breast cancer associated with overexpression of G3BP1 and overexpression of G3BP2, and breast cancer associated with overexpression of G3BP1, overexpression of G3BP2, and overexpression of ZEB1.

4. A method of treating a breast cancer in a patient, the method comprising:
   i) identifying the patient as having a breast cancer selected from: breast cancer associated with overexpression of G3BP2, breast cancer associated with overexpression of ZEB1, breast cancer associated with overexpression of G3BP2 and overexpression of ZEB1, breast cancer associated with overexpression of G3BP1, breast cancer associated with overexpression of G3BP1 and overexpression of G3BP2, and breast cancer associated with overexpression of G3BP1, overexpression of G3BP2, and overexpression of ZEB1; and
   ii) administering to the patient a therapeutically effective amount of a compound having the formula:

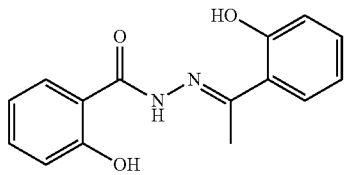

or a pharmaceutically acceptable salt thereof.

5. A method of inhibiting G3BP1, G3BP2, or ZEB1, or any combination thereof, in a breast cancer cell, the method comprising contacting the breast cancer cell with an effective amount of a compound having the formula:

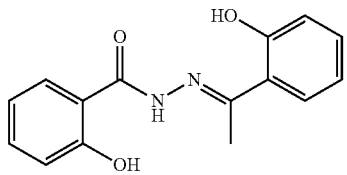

or a pharmaceutically acceptable salt thereof.

6. A method of inhibiting growth of a breast cancer stem cell, the method comprising contacting the breast cancer stem cell with an effective amount of a compound having the formula:

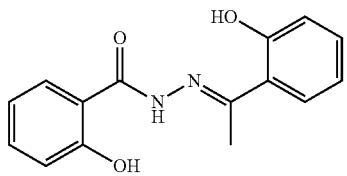

or a pharmaceutically acceptable salt thereof.

7. The method of claim 6, wherein the breast cancer stem cell is associated with an overexpression selected from: overexpression of G3BP2, overexpression of ZEB1, overexpression of G3BP2 and ZEB1, overexpression of G3BP1, overexpression of G3BP1 and G3BP2, and overexpression of G3BP1, G3BP2, and ZEB1.

8. The method of claim 6, wherein the breast cancer stem cell is resistant to treatment with a chemotherapeutic agent.

9. The method of claim 2, wherein the breast cancer is selected from: breast cancer associated with overexpression of G3BP2, breast cancer associated with overexpression of ZEB1, breast cancer associated with overexpression of G3BP2 and overexpression of ZEB1, breast cancer associated with overexpression of G3BP1, breast cancer associated with overexpression of G3BP1 and overexpression of G3BP2, and breast cancer associated with overexpression of G3BP1, overexpression of G3BP2, and overexpression of ZEB1.

* * * * *

UNITED STATES PATENT AND TRADEMARK OFFICE
CERTIFICATE OF CORRECTION

PATENT NO. : 11,427,543 B2
APPLICATION NO. : 16/318846
DATED : August 30, 2022
INVENTOR(S) : Igor Garkavtsev and Rakesh K. Jain Page 1 of 1

It is certified that error appears in the above-identified patent and that said Letters Patent is hereby corrected as shown below:

In the Specification

In Column 1, Line 17, delete "1R21CA169616" and insert -- CA169616 --

In Column 1, Lines 18-19, delete "and W81XWH-10-1-0016 awarded by the Department of Defense"

Signed and Sealed this
Eleventh Day of February, 2025

Coke Morgan Stewart
*Acting Director of the United States Patent and Trademark Office*

SEQUENCE LISTING

```
<160> NUMBER OF SEQ ID NOS: 10

<210> SEQ ID NO 1
<211> LENGTH: 23
<212> TYPE: DNA
<213> ORGANISM: Artificial Sequence
<220> FEATURE:
<223> OTHER INFORMATION: qPCR Primer for ChIP-qPCR - ZEB1 (F) (5'-3')

<400> SEQUENCE: 1
ccagtttgga gagacgttgt aag                                              23

<210> SEQ ID NO 2
<211> LENGTH: 20
<212> TYPE: DNA
<213> ORGANISM: Artificial Sequence
<220> FEATURE:
<223> OTHER INFORMATION: qPCR Primer for ChIP-qPCR - ZEB1 (R) (5'-3')

<400> SEQUENCE: 2
ctctcgccac aggaactgtc                                                  20

<210> SEQ ID NO 3
<211> LENGTH: 21
<212> TYPE: DNA
<213> ORGANISM: Artificial Sequence
<220> FEATURE:
<223> OTHER INFORMATION: qPCR Primer for ChIP-qPCR - K4 positive control
      (F) (5'-3')

<400> SEQUENCE: 3
cttgattctg agggtcagga g                                                21

<210> SEQ ID NO 4
<211> LENGTH: 21
<212> TYPE: DNA
<213> ORGANISM: Artificial Sequence
<220> FEATURE:
<223> OTHER INFORMATION: qPCR Primer for ChIP-qPCR - K4 positive control
      (R) (5'-3')

<400> SEQUENCE: 4
gctgatgcat aggtctggaa g                                                21

<210> SEQ ID NO 5
<211> LENGTH: 22
<212> TYPE: DNA
<213> ORGANISM: Artificial Sequence
<220> FEATURE:
<223> OTHER INFORMATION: qPCR Primer for ChIP-qPCR - Negative control
      (F) (5'-3')

<400> SEQUENCE: 5
tggatcttgt gtctgtcact cc                                               22

<210> SEQ ID NO 6
<211> LENGTH: 22
<212> TYPE: DNA
<213> ORGANISM: Artificial Sequence
<220> FEATURE:
<223> OTHER INFORMATION: qPCR Primer for ChIP-qPCR - Negative control
      (R) (5'-3')

<400> SEQUENCE: 6
aagtggcaag ggagtttagt tg                                               22
```

<210> SEQ ID NO 7
<211> LENGTH: 963
<212> TYPE: PRT
<213> ORGANISM: Homo sapiens

<400> SEQUENCE: 7

```
Met Ala Thr Ala Ala Glu Thr Ser Ala Ser Glu Pro Glu Ala Glu Ser
1               5                   10                  15

Lys Ala Gly Pro Lys Ala Asp Gly Glu Glu Asp Glu Val Lys Ala Ala
            20                  25                  30

Arg Thr Arg Arg Lys Val Leu Ser Arg Ala Val Ala Ala Ala Thr Tyr
        35                  40                  45

Lys Thr Met Gly Pro Ala Trp Asp Gln Gln Glu Gly Val Ser Glu
    50                  55                  60

Ser Asp Gly Asp Glu Tyr Ala Met Ala Ser Ser Ala Glu Ser Ser Pro
65                  70                  75                  80

Gly Glu Tyr Glu Trp Glu Tyr Asp Glu Glu Glu Lys Asn Gln Leu
                85                  90                  95

Glu Ile Glu Arg Leu Glu Glu Gln Leu Ser Ile Asn Val Tyr Asp Tyr
            100                 105                 110

Asn Cys His Val Asp Leu Ile Arg Leu Arg Leu Glu Gly Glu Leu
                115                 120                 125

Thr Lys Val Arg Met Ala Arg Gln Lys Met Ser Glu Ile Phe Pro Leu
130                 135                 140

Thr Glu Glu Leu Trp Leu Glu Trp Leu His Asp Ile Ser Met Ala
145                 150                 155                 160

Gln Asp Gly Leu Asp Arg Glu His Val Tyr Asp Leu Phe Glu Lys Ala
                165                 170                 175

Val Lys Asp Tyr Ile Cys Pro Asn Ile Trp Leu Glu Tyr Gly Gln Tyr
            180                 185                 190

Ser Val Gly Gly Ile Gly Gln Lys Gly Gly Leu Glu Lys Val Arg Ser
        195                 200                 205

Val Phe Glu Arg Ala Leu Ser Ser Val Gly Leu His Met Thr Lys Gly
    210                 215                 220

Leu Ala Leu Trp Glu Ala Tyr Arg Glu Phe Glu Ser Ala Ile Val Glu
225                 230                 235                 240

Ala Ala Arg Leu Glu Lys Val His Ser Leu Phe Arg Arg Gln Leu Ala
                245                 250                 255

Ile Pro Leu Tyr Asp Met Glu Ala Thr Phe Ala Glu Tyr Glu Glu Trp
            260                 265                 270

Ser Glu Asp Pro Ile Pro Glu Ser Val Ile Gln Asn Tyr Asn Lys Ala
        275                 280                 285

Leu Gln Gln Leu Glu Lys Tyr Lys Pro Tyr Glu Glu Ala Leu Leu Gln
    290                 295                 300

Ala Glu Ala Pro Arg Leu Ala Glu Tyr Gln Ala Tyr Ile Asp Phe Glu
305                 310                 315                 320

Met Lys Ile Gly Asp Pro Ala Arg Ile Gln Leu Ile Phe Glu Arg Ala
                325                 330                 335

Leu Val Glu Asn Cys Leu Val Pro Asp Leu Trp Ile Arg Tyr Ser Gln
            340                 345                 350

Tyr Leu Asp Arg Gln Leu Lys Val Lys Asp Leu Val Leu Ser Val His
        355                 360                 365

Asn Arg Ala Ile Arg Asn Cys Pro Trp Thr Val Ala Leu Trp Ser Arg
    370                 375                 380
```

```
Tyr Leu Leu Ala Met Glu Arg His Gly Val Asp His Gln Val Ile Ser
385                 390                 395                 400

Val Thr Phe Glu Lys Ala Leu Asn Ala Gly Phe Ile Gln Ala Thr Asp
            405                 410                 415

Tyr Val Glu Ile Trp Gln Ala Tyr Leu Asp Tyr Leu Arg Arg Arg Val
        420                 425                 430

Asp Phe Lys Gln Asp Ser Ser Lys Glu Leu Glu Leu Arg Ala Ala
    435                 440                 445

Phe Thr Arg Ala Leu Glu Tyr Leu Lys Gln Glu Val Glu Glu Arg Phe
    450                 455                 460

Asn Glu Ser Gly Asp Pro Ser Cys Val Ile Met Gln Asn Trp Ala Arg
465                 470                 475                 480

Ile Glu Ala Arg Leu Cys Asn Asn Met Gln Lys Ala Arg Glu Leu Trp
            485                 490                 495

Asp Ser Ile Met Thr Arg Gly Asn Ala Lys Tyr Ala Asn Met Trp Leu
            500                 505                 510

Glu Tyr Tyr Asn Leu Glu Arg Ala His Gly Asp Thr Gln His Cys Arg
        515                 520                 525

Lys Ala Leu His Arg Ala Val Gln Cys Thr Ser Asp Tyr Pro Glu His
530                 535                 540

Val Cys Glu Val Leu Leu Thr Met Glu Arg Thr Gly Ser Leu Glu
545                 550                 555                 560

Asp Trp Asp Ile Ala Val Gln Lys Thr Glu Thr Arg Leu Ala Arg Val
            565                 570                 575

Asn Glu Gln Arg Met Lys Ala Ala Glu Lys Glu Ala Ala Leu Val Gln
                580                 585                 590

Gln Glu Glu Glu Lys Ala Glu Gln Arg Lys Arg Ala Arg Ala Glu Lys
        595                 600                 605

Lys Ala Leu Lys Lys Lys Lys Ile Arg Gly Pro Glu Lys Arg Gly
        610                 615                 620

Ala Asp Glu Asp Glu Lys Glu Trp Gly Asp Asp Glu Glu Glu Gln
625                 630                 635                 640

Pro Ser Lys Arg Arg Arg Val Glu Asn Ser Ile Pro Ala Ala Gly Glu
                645                 650                 655

Thr Gln Asn Val Glu Val Ala Ala Gly Pro Ala Gly Lys Cys Ala Ala
                660                 665                 670

Val Asp Val Glu Pro Pro Ser Lys Gln Lys Glu Lys Ala Ala Ser Leu
        675                 680                 685

Lys Arg Asp Met Pro Lys Val Leu His Asp Ser Ser Lys Asp Ser Ile
        690                 695                 700

Thr Val Phe Val Ser Asn Leu Pro Tyr Ser Met Gln Glu Pro Asp Thr
705                 710                 715                 720

Lys Leu Arg Pro Leu Phe Glu Ala Cys Gly Glu Val Val Gln Ile Arg
                725                 730                 735

Pro Ile Phe Ser Asn Arg Gly Asp Phe Arg Gly Tyr Cys Tyr Val Glu
            740                 745                 750

Phe Lys Glu Glu Lys Ser Ala Leu Gln Ala Leu Glu Met Asp Arg Lys
        755                 760                 765

Ser Val Glu Gly Arg Pro Met Phe Val Ser Pro Cys Val Asp Lys Ser
        770                 775                 780

Lys Asn Pro Asp Phe Lys Val Phe Arg Tyr Ser Thr Ser Leu Glu Lys
785                 790                 795                 800

His Lys Leu Phe Ile Ser Gly Leu Pro Phe Ser Cys Thr Lys Glu Glu
```

-continued

```
                    805                 810                 815
Leu Glu Glu Ile Cys Lys Ala His Gly Thr Val Lys Asp Leu Arg Val
            820                 825                 830

Leu Thr Asn Arg Ala Gly Lys Pro Lys Gly Leu Ala Tyr Val Glu Tyr
            835                 840                 845

Glu Asn Glu Ser Gln Ala Ser Gln Ala Val Met Lys Met Asp Gly Met
        850                 855                 860

Thr Ile Lys Glu Asn Ile Ile Lys Val Ala Ile Ser Asn Pro Pro Gln
865                 870                 875                 880

Arg Lys Val Pro Glu Lys Pro Glu Thr Arg Lys Ala Pro Gly Gly Pro
                885                 890                 895

Met Leu Leu Pro Gln Thr Tyr Gly Ala Arg Gly Lys Gly Arg Thr Gln
            900                 905                 910

Leu Ser Leu Leu Pro Arg Ala Leu Gln Arg Pro Ser Ala Ala Ala Pro
        915                 920                 925

Gln Ala Glu Asn Gly Pro Ala Ala Pro Ala Val Ala Ala Pro Ala
    930                 935                 940

Ala Thr Glu Ala Pro Lys Met Ser Asn Ala Asp Phe Ala Lys Leu Phe
945                 950                 955                 960

Leu Arg Lys
```

<210> SEQ ID NO 8
<211> LENGTH: 21
<212> TYPE: DNA
<213> ORGANISM: Artificial Sequence
<220> FEATURE:
<223> OTHER INFORMATION: shRNA for G3BP2, cloned in pLKO_TRC005
      lentiviral vector

<400> SEQUENCE: 8
cgggagtttg tgaggcaata t                                         21

<210> SEQ ID NO 9
<211> LENGTH: 21
<212> TYPE: DNA
<213> ORGANISM: Artificial Sequence
<220> FEATURE:
<223> OTHER INFORMATION: shRNA for G3BP2, cloned in pLKO_TRC005
      lentiviral vector

<400> SEQUENCE: 9
gactctgaca accgtagaat a                                         21

<210> SEQ ID NO 10
<211> LENGTH: 21
<212> TYPE: DNA
<213> ORGANISM: Artificial Sequence
<220> FEATURE:
<223> OTHER INFORMATION: ING4 shRNA insert, cloned in pLKO_TRC005
      lentiviral vector

<400> SEQUENCE: 10
ccgggaaccc acctattgcc t                                         21